(12) United States Patent
Oron et al.

(10) Patent No.: US 10,004,896 B2
(45) Date of Patent: Jun. 26, 2018

(54) ANCHORS AND IMPLANT DEVICES

(71) Applicant: BlueWind Medical Ltd., Herzliya (IL)

(72) Inventors: Guri Oron, Tel Aviv (IL); Yossi Gross, Moshav Mazor (IL); Bar Eytan, Gedera (IL); Eran Benjamin, Tel Aviv (IL); Anton Plotkin, Tel Aviv (IL)

(73) Assignee: BLUEWIND MEDICAL LTD., Herzeliya (IL)

( * ) Notice: Subject to any disclaimer, the term of this patent is extended or adjusted under 35 U.S.C. 154(b) by 354 days.

(21) Appl. No.: 14/601,604

(22) Filed: Jan. 21, 2015

(65) Prior Publication Data

US 2016/0206882 A1 Jul. 21, 2016

(51) Int. Cl.
*A61N 1/36* (2006.01)
*A61N 1/05* (2006.01)
*A61B 17/34* (2006.01)
*A61N 1/372* (2006.01)
*A61N 1/375* (2006.01)

(52) U.S. Cl.
CPC ........ *A61N 1/0558* (2013.01); *A61B 17/3403* (2013.01); *A61B 17/3468* (2013.01); *A61N 1/37205* (2013.01); *A61B 2017/3407* (2013.01); *A61B 2017/3413* (2013.01); *A61N 1/36017* (2013.01); *A61N 1/3756* (2013.01)

(58) Field of Classification Search
CPC . A61N 1/0558; A61N 1/37205; A61N 1/3756
See application file for complete search history.

(56) References Cited

U.S. PATENT DOCUMENTS

| | | |
|---|---|---|
| 3,411,507 A | 4/1964 | Wingrove |
| 3,693,625 A | 9/1972 | Auphan |
| 4,019,518 A | 4/1977 | Maurer et al. |
| 4,338,945 A | 7/1982 | Kosugi et al. |
| 4,392,496 A | 7/1983 | Stanton |
| 4,535,785 A | 8/1985 | Van Den Honert |
| 4,559,948 A | 12/1985 | Liss et al. |
| 4,573,481 A | 3/1986 | Bullara |
| 4,585,005 A | 4/1986 | Lue et al. |

(Continued)

FOREIGN PATENT DOCUMENTS

| | | |
|---|---|---|
| DE | 102008054403 | 6/2010 |
| EP | 0 688 577 | 12/1995 |

(Continued)

OTHER PUBLICATIONS

An Office Action dated Dec. 12, 2016, which issued during the prosecution of U.S. Appl. No. 14/939,418.

(Continued)

*Primary Examiner* — George Evanisko
(74) *Attorney, Agent, or Firm* — Sughrue Mion, PLLC

(57) ABSTRACT

Apparatus including an implant is provided, the implant including: a rod-shaped housing, having a distal half and a proximal half, and configured to be injected distally into tissue of a subject; a cathode on the distal half of the housing; an anchor configured to protrude from the proximal half of the housing, no anchor being configured to protrude from the distal half of the housing; an anode; and circuitry disposed within the housing, configured to drive a current between the cathode and the anode. Other embodiments are also described.

14 Claims, 29 Drawing Sheets

(56) References Cited

U.S. PATENT DOCUMENTS

| | | |
|---|---|---|
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,739,764 A | 4/1988 | Lau |
| 4,808,157 A | 2/1989 | Coombs |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,069,680 A | 12/1991 | Grandjean |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,263,480 A | 11/1993 | Wernicke |
| 5,282,468 A | 2/1994 | Klepinski |
| 5,284,479 A | 2/1994 | De Jong |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,335,657 A | 8/1994 | Terry, Jr. |
| 5,411,535 A | 5/1995 | Fujii et al. |
| 5,423,872 A | 6/1995 | Cigaina |
| 5,439,938 A | 8/1995 | Synder et al. |
| 5,454,840 A | 10/1995 | Krakovsky et al. |
| 5,487,760 A | 1/1996 | Villafana |
| 5,505,201 A | 4/1996 | Grill, Jr. |
| 5,540,730 A | 7/1996 | Terry, Jr. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,755,750 A | 5/1998 | Petruska |
| 5,776,170 A | 7/1998 | Macdonald et al. |
| 5,776,171 A | 7/1998 | Peckham |
| 5,814,089 A | 9/1998 | Stokes |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,861,019 A | 1/1999 | Sun et al. |
| 5,916,239 A | 6/1999 | Geddes et al. |
| 5,938,584 A | 8/1999 | Ardito et al. |
| 5,944,680 A | 8/1999 | Christopherson |
| 5,954,758 A | 9/1999 | Peckham |
| 5,991,664 A | 11/1999 | Seligman |
| 6,002,964 A | 12/1999 | Feler et al. |
| 6,026,326 A | 2/2000 | Bardy |
| 6,026,328 A | 2/2000 | Peckham |
| 6,032,076 A | 2/2000 | Melvin et al. |
| 6,058,331 A | 5/2000 | King et al. |
| 6,066,163 A | 5/2000 | John |
| 6,071,274 A | 6/2000 | Thompson et al. |
| 6,091,992 A | 6/2000 | Bourgeois |
| 6,083,249 A | 7/2000 | Familoni |
| 6,086,525 A | 7/2000 | Davey et al. |
| 6,091,977 A | 7/2000 | Tarjan et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,161,048 A | 12/2000 | Sluijter et al. |
| 6,169,924 B1 | 1/2001 | Meloy et al. |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,240,316 B1 | 5/2001 | Richmond |
| 6,246,912 B1 | 6/2001 | Sluijter et al. |
| 6,266,564 B1 | 7/2001 | Schwartz |
| 6,272,383 B1 | 8/2001 | Grey |
| 6,292,703 B1 | 9/2001 | Meier et al. |
| 6,319,241 B1 | 11/2001 | King |
| 6,332,089 B1 | 12/2001 | Acker |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | Dilorenzo |
| 6,405,079 B1 | 6/2002 | Ansarinia |
| 6,442,432 B2 | 8/2002 | Lee |
| 6,445,953 B1 | 9/2002 | Bulkes et al. |
| 6,449,507 B1 | 9/2002 | Hill et al. |
| 6,456,878 B1 | 9/2002 | Yerich et al. |
| 6,463,328 B1 | 10/2002 | John |
| 6,473,644 B1 | 10/2002 | Terry, Jr. et al. |
| 6,496,729 B2 | 12/2002 | Thompson |
| 6,496,730 B1 | 12/2002 | Kleckner et al. |
| 6,582,441 B1 | 6/2003 | He et al. |
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,618,627 B2 | 9/2003 | Lattner et al. |
| 6,641,542 B2 | 11/2003 | Cho et al. |
| 6,682,480 B1 | 1/2004 | Habib et al. |
| 6,735,474 B1 | 5/2004 | Loeb et al. |
| 6,770,022 B2 | 8/2004 | Mechlenburg |
| 6,829,508 B2 | 12/2004 | Schulman |
| 6,839,594 B2 | 1/2005 | Cohen |
| 6,892,098 B2 | 5/2005 | Ayal |
| 6,907,295 B2 | 6/2005 | Gross et al. |
| 6,909,917 B2 | 6/2005 | Woods et al. |
| 7,025,730 B2 | 4/2006 | Cho et al. |
| 7,027,860 B2 | 4/2006 | Bruninga et al. |
| 7,047,076 B1 | 5/2006 | Li et al. |
| 7,054,692 B1 * | 5/2006 | Whitehurst ............ A61N 1/375 600/386 |
| 7,149,575 B2 | 12/2006 | Ostroff et al. |
| 7,177,698 B2 | 2/2007 | Klosterman et al. |
| 7,212,867 B2 | 5/2007 | Venrooij et al. |
| 7,228,178 B2 | 6/2007 | Carroll |
| 7,277,749 B2 | 10/2007 | Gordon et al. |
| 7,289,853 B1 | 10/2007 | Campbell et al. |
| 7,324,852 B2 | 1/2008 | Barolat et al. |
| 7,324,853 B2 | 1/2008 | Ayal |
| 7,389,145 B2 | 6/2008 | Kilgore et al. |
| 7,483,752 B2 | 1/2009 | Von arx et al. |
| 7,502,652 B2 | 3/2009 | Gaunt et al. |
| 7,532,932 B2 | 5/2009 | Denker et al. |
| 7,536,226 B2 | 5/2009 | Williams |
| 7,628,750 B2 | 12/2009 | Cohen |
| 7,630,771 B2 | 12/2009 | Cauller |
| 7,634,313 B1 | 12/2009 | Kroll et al. |
| 7,655,014 B2 | 2/2010 | Ko et al. |
| 7,657,311 B2 | 2/2010 | Bardy et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,711,434 B2 | 5/2010 | Denker et al. |
| 7,736,379 B2 | 6/2010 | Ewers et al. |
| 7,780,625 B2 | 8/2010 | Bardy |
| 7,797,050 B2 | 9/2010 | Libbus et al. |
| 7,848,818 B2 | 12/2010 | Barolat et al. |
| 7,917,226 B2 | 5/2011 | Nghiem |
| 7,937,148 B2 | 5/2011 | Jacobson |

(56) References Cited

U.S. PATENT DOCUMENTS

| | | |
|---|---|---|
| 7,941,218 B2 | 5/2011 | Sambelashvili et al. |
| 7,974,706 B2 | 7/2011 | Moffitt et al. |
| 7,991,467 B2 | 8/2011 | Markowitz et al. |
| 7,996,089 B2 | 8/2011 | Haugland et al. |
| 7,996,092 B2 | 8/2011 | Mrva et al. |
| 8,019,443 B2 | 9/2011 | Scheicher et al. |
| 8,055,350 B2 | 11/2011 | Roberts |
| 8,075,556 B2 | 12/2011 | Betts |
| 8,090,438 B2 | 1/2012 | Bardy et al. |
| 8,115,448 B2 | 2/2012 | John |
| 8,131,377 B2 | 3/2012 | Shhi et al. |
| 8,170,675 B2 | 5/2012 | Alataris et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,224,453 B2 | 7/2012 | De Ridder |
| 8,255,057 B2 | 8/2012 | Fang et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,396,559 B2 | 3/2013 | Alataris et al. |
| 8,428,748 B2 | 4/2013 | Alataris et al. |
| 8,463,404 B2 | 6/2013 | Levi et al. |
| 8,509,905 B2 | 8/2013 | Alataris et al. |
| 8,509,906 B2 | 8/2013 | Walker et al. |
| 8,554,326 B2 | 10/2013 | Alataris et al. |
| 8,634,927 B2 | 1/2014 | Olson et al. |
| 8,649,874 B2 | 2/2014 | Alataris et al. |
| 8,694,108 B2 | 4/2014 | Alataris et al. |
| 8,694,109 B2 | 4/2014 | Alataris et al. |
| 8,712,533 B2 | 4/2014 | Alataris et al. |
| 8,718,781 B2 | 5/2014 | Alataris et al. |
| 8,718,782 B2 | 5/2014 | Alataris et al. |
| 8,755,893 B2 | 6/2014 | Gross et al. |
| 8,768,472 B2 | 7/2014 | Fang et al. |
| 8,774,926 B2 | 7/2014 | Alataris et al. |
| 8,788,045 B2 | 7/2014 | Gross et al. |
| 8,792,988 B2 | 7/2014 | Alataris et al. |
| 8,849,410 B2 | 9/2014 | Walker et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 9,248,279 B2 | 2/2016 | Chen et al. |
| 2002/0077554 A1 | 6/2002 | Schwartz et al. |
| 2002/0099419 A1 | 7/2002 | Cohen et al. |
| 2002/0124848 A1 | 9/2002 | Sullivan et al. |
| 2002/0183805 A1 | 12/2002 | Fang et al. |
| 2002/0183817 A1 | 12/2002 | Van Venrooij et al. |
| 2003/0040774 A1 | 2/2003 | Terry et al. |
| 2003/0060858 A1 | 3/2003 | Kieval et al. |
| 2003/0100933 A1 | 5/2003 | Ayal |
| 2003/0114905 A1* | 6/2003 | Kuzma ............... A61N 1/0551 607/116 |
| 2003/0176898 A1 | 9/2003 | Gross et al. |
| 2003/0236557 A1* | 12/2003 | Whitehurst .......... A61N 1/0556 607/39 |
| 2003/0236558 A1 | 12/2003 | Whitehurst et al. |
| 2004/0015205 A1 | 1/2004 | Whitehurst et al. |
| 2004/0019368 A1 | 1/2004 | Lattner et al. |
| 2004/0048795 A1 | 3/2004 | Ivanova et al. |
| 2004/0073270 A1 | 4/2004 | Firlik et al. |
| 2004/0254624 A1 | 6/2004 | Johnson |
| 2004/0167584 A1 | 8/2004 | Carroll et al. |
| 2004/0249431 A1 | 12/2004 | Ransbury et al. |
| 2004/0254612 A1 | 12/2004 | Ezra et al. |
| 2005/0113894 A1* | 5/2005 | Zilberman ............... A61N 1/05 607/116 |
| 2005/0131495 A1 | 6/2005 | Parramon et al. |
| 2005/0143789 A1 | 6/2005 | Whitehurst |
| 2005/0165457 A1 | 7/2005 | Benser et al. |
| 2006/0085039 A1 | 4/2006 | Hastings et al. |
| 2006/0100668 A1 | 5/2006 | Ben-David et al. |
| 2006/0155345 A1 | 7/2006 | Williams et al. |
| 2006/0271137 A1 | 11/2006 | Stanton-Hicks |
| 2007/0032827 A1 | 2/2007 | Katims |
| 2007/0067000 A1 | 3/2007 | Strother et al. |
| 2007/0067007 A1 | 3/2007 | Schulman |
| 2007/0073354 A1 | 3/2007 | Knudson et al. |
| 2007/0083240 A1 | 4/2007 | Peterson et al. |
| 2007/0173893 A1 | 7/2007 | Pitts |
| 2007/0208392 A1 | 9/2007 | Kuschner et al. |
| 2007/0255369 A1 | 11/2007 | Bonde et al. |
| 2007/0293912 A1 | 12/2007 | Cowan et al. |
| 2008/0009914 A1 | 1/2008 | Buysman et al. |
| 2008/0021336 A1 | 1/2008 | Dobak |
| 2008/0027513 A1 | 1/2008 | Carbunaru |
| 2008/0039915 A1 | 2/2008 | Van Den Biggelaar |
| 2008/0091255 A1* | 4/2008 | Caparso ............ A61N 1/36114 607/116 |
| 2008/0103407 A1 | 5/2008 | Bolea et al. |
| 2008/0103572 A1 | 5/2008 | Gerber |
| 2008/0119911 A1 | 5/2008 | Rosero |
| 2008/0132964 A1 | 6/2008 | Cohen et al. |
| 2008/0269740 A1 | 10/2008 | Bonde et al. |
| 2009/0012590 A1 | 1/2009 | Inman et al. |
| 2009/0036975 A1 | 2/2009 | Ward et al. |
| 2009/0048642 A1 | 2/2009 | Goroszeniuk |
| 2009/0149912 A1 | 6/2009 | Dacey et al. |
| 2009/0152954 A1 | 6/2009 | Le et al. |
| 2009/0204170 A1 | 8/2009 | Hastings et al. |
| 2009/0204173 A1 | 8/2009 | Fang et al. |
| 2009/0270951 A1 | 10/2009 | Kallmyer |
| 2009/0281594 A1 | 11/2009 | King et al. |
| 2009/0326602 A1 | 12/2009 | Glukhovsky et al. |
| 2010/0016911 A1* | 1/2010 | Willis .................... A61N 1/056 607/9 |
| 2010/0094367 A1 | 4/2010 | Sen |
| 2010/0121405 A1 | 5/2010 | Ternes et al. |
| 2010/0125310 A1 | 5/2010 | Wilson et al. |
| 2010/0125313 A1 | 5/2010 | Lee et al. |
| 2010/0198298 A1 | 8/2010 | Glukovsky et al. |
| 2010/0211131 A1 | 8/2010 | Williams et al. |
| 2010/0241195 A1 | 9/2010 | Meadows et al. |
| 2010/0249875 A1 | 9/2010 | Kishawi et al. |
| 2010/0312320 A1 | 9/2010 | Faltys et al. |
| 2010/0280568 A1 | 11/2010 | Bulkes et al. |
| 2010/0305392 A1 | 12/2010 | Gross et al. |
| 2010/0324630 A1 | 12/2010 | Lee et al. |
| 2011/0034782 A1 | 2/2011 | Sugimachi et al. |
| 2011/0046696 A1 | 2/2011 | Barolat et al. |
| 2011/0087337 A1 | 4/2011 | Forsell |
| 2011/0093036 A1 | 4/2011 | Mashiach |
| 2011/0137365 A1 | 6/2011 | Ben-Erza et al. |
| 2011/0152965 A1 | 6/2011 | Mashiach |
| 2011/0160792 A1 | 6/2011 | Fishel |
| 2011/0160793 A1 | 6/2011 | Gindele |
| 2011/0160798 A1 | 6/2011 | Ackermann et al. |
| 2011/0208260 A1 | 8/2011 | Jacobson |
| 2011/0208271 A1 | 8/2011 | Dobak |
| 2011/0224744 A1 | 9/2011 | Moffitt et al. |
| 2011/0230922 A1 | 9/2011 | Fishel |
| 2011/0251660 A1 | 10/2011 | Griswold |
| 2011/0270339 A1 | 11/2011 | Murray et al. |
| 2011/0282412 A1 | 11/2011 | Glukhovsky et al. |
| 2011/0301670 A1 | 12/2011 | Gross |
| 2012/0010694 A1 | 1/2012 | Lutter et al. |
| 2012/0035679 A1 | 2/2012 | Dagan et al. |
| 2012/0041511 A1 | 2/2012 | Lee |
| 2012/0041514 A1 | 2/2012 | Gross et al. |
| 2012/0065701 A1 | 3/2012 | Cauller |
| 2012/0083857 A1 | 4/2012 | Bradley et al. |
| 2012/0101326 A1 | 4/2012 | Simon et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2012/0158081 A1 | 6/2012 | Gross et al. |
| 2012/0296389 A1 | 11/2012 | Fang et al. |

(56) References Cited

U.S. PATENT DOCUMENTS

| | | | |
|---|---|---|---|
| 2013/0006326 A1 | 1/2013 | Ackermann et al. | |
| 2013/0066393 A1 | 3/2013 | Gross et al. | |
| 2013/0325081 A1* | 12/2013 | Karst | A61N 1/36592 607/25 |
| 2013/0325084 A1 | 12/2013 | Lee | |
| 2014/0214134 A1 | 7/2014 | Peterson | |
| 2014/0296940 A1 | 10/2014 | Gross | |
| 2015/0004709 A1 | 1/2015 | Nazarpoor | |
| 2015/0018728 A1 | 1/2015 | Gross et al. | |
| 2015/0080979 A1 | 3/2015 | Lasko et al. | |
| 2015/0100109 A1 | 4/2015 | Feldman et al. | |
| 2015/0258339 A1 | 9/2015 | Burchiel et al. | |
| 2015/0335882 A1 | 11/2015 | Gross et al. | |
| 2017/0119435 A1 | 5/2017 | Gross et al. | |

FOREIGN PATENT DOCUMENTS

| | | |
|---|---|---|
| EP | 1533000 | 5/2005 |
| WO | 1998/010832 | 3/1998 |
| WO | 1999/026530 | 6/1999 |
| WO | 01/10432 | 2/2001 |
| WO | 2001/010375 | 2/2001 |
| WO | 01/26729 | 4/2001 |
| WO | 02/09808 | 2/2002 |
| WO | 2004/064729 | 8/2004 |
| WO | 2006/102626 | 9/2006 |
| WO | 2007/019491 | 2/2007 |
| WO | 2009/055574 | 4/2009 |
| WO | 2009/110935 | 9/2009 |
| WO | 2011/154937 | 12/2011 |
| WO | 2012/012591 | 1/2012 |
| WO | 2013/035092 | 3/2013 |
| WO | 2013/106884 | 7/2013 |
| WO | 2013/111137 | 8/2013 |
| WO | 2013/156038 | 10/2013 |
| WO | 2013/164829 | 11/2013 |
| WO | 2014081978 | 5/2014 |
| WO | 2014/087337 | 6/2014 |
| WO | 2014167568 | 10/2014 |
| WO | 2015004673 | 1/2015 |
| WO | 2016/172109 | 10/2016 |

OTHER PUBLICATIONS

An Office Action dated Nov. 21, 2016, which issued during the prosecution of U.S. Appl. No. 14/601,626.
Kucklick, Theodore R., ed. The medical device R&D handbook. Chapter 3—Intro to needles and cannulae. CRC Press, 2012.
An Office Action dated Aug. 8, 2016, which issued during the prosecution of U.S. Appl. No. 14/735,741.
Brindley (1983) A technique for anodally blocking large nerve fibers.
U.S. Appl. No. 60/985,353, filed Nov. 5, 2007.
Lind (2012) Advances in spinal cord stimulation.
Shealy (1967) Electrical inhibition of pain by stimulation of the dorsal columns.
Nov. 30, 2015 massdevice.com—St. Jude Medical's Proclaim Elite debuts in Europe.
Kaplan HM, Loeb GE. Design and fabrication of an injection tool for neuromuscular microstimulators. Ann Biomed Eng. Epub Jun. 24, 2009.
Supplementary European Search Report dated Dec. 22, 2014, which issued during the prosecution of Applicant's European App No. 11792044.7.
An Office Action dated Oct. 30, 2015, which issued during the prosecution of U.S. Appl. No. 14/226,723.
Reggiani et al. "Biophysical effects of high frequency electrical field on muscle fibers in culture." (2009) pp. 49-56.
C. de Balthasar, G. Cosendai, M. Hansen, D. Canfield, L. Chu, R. Davis, and J. Schulman, "Attachment of leads to RF-BION® microstimulators."Jul. 2005.

D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.
G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.
G.E. Loeb, F.J. Richmond, and L.L. Baker, "The BION devices: injectable interfaces with peripheral nerves and muscles," Neurosurgical focus, vol. 20, 2006, pp. 1-9.
E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.
A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.
A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.
A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.
A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.
W.H. Tran, G.E. Loeb, F.J.R. Richmond, A.G. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.
W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.
P.R. Troyk, "Injectable electronic identification, monitoring, and stimulation systems," Biomedical Engineering, vol. 1, 1999, p. 177.
T.K. Whitehurst, J.H. Schulman, K.N. Jaax, and R. Carbunaru, "The Bion® Microstimulator and its Clinical Applications," Implantable Neural Prostheses 1, 2009, pp. 253-273.
D.J. Young, "Wireless powering and data telemetry for biomedical implants," Engineering in Medicine and Biology Society, 2009. EMBC 2009. Annual International Conference of the IEEE, 2009, pp. 3221-3224.
Reid R. Harrison, et al., "Wireless Neural Recording with Single Low-Power Integrated Circuit", IEEE Trans Neural Syst Rehabil Eng. Aug. 2009; 17(4): 322-329.
An International Search Report and a Written Opinion both dated Apr. 17, 2012 which issued during the prosecution of Applicant's PCT/IL11/00870.
Patents Galore: Implantable Neurostimulators Fight Snoring and Corpse Eye-Proof Scanners. Printout from http://medgadget.com/ 2006/03/patents_galore.html (Downloaded Jan. 2012).
Chris Seper, "Neuros Medical Launches to Develop New Device to Block Amputee, Chronic Pain", Mar. 16, 2009.
Urgent® PC, Simple. Safe. Effective. Neuromodulation System, Uroplasty, Mar. 2009.
"JumpStart and Case Technology Ventures Invest in Neuros Medical", CTV Case Technology Ventures, Mar. 17, 2009.
"Responses to median and tibial nerve stimulation in patients with chronic neuropathic pain", by Theuvenet, Brain Topography, vol. 11, No. 4, 1999, pp. 305-313(9)—an abstract.

(56) References Cited

OTHER PUBLICATIONS

Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.
An Office Action dated Feb. 13, 2004, which issued during the prosecution of U.S. Appl. No. 10/254,024.
Bathien et al., Inhibition and synchronisation of tremor induced by a muscle twitch. J. Neurol, Neurosurg. and Psych. 1980, 43, 713-718.
Jobges et al., Vibratory proprioceptive stimulation affects Parkinsonian tremor. Parkinsonism & Related Disorders, 8(3), 171-176, Jan. 2002.
Mones and Weiss, The response of the tremor of patients with Parkinsonism to peripheral nerve stimulation. J. Neurol. Neurosurg. Psychiat. 1969, 32. 512-519.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
Cerebral Palsy, Barry S. Russman MD, CCurrent Science Inc. 2000.
A Notice of Allowance dated Mar. 7, 2005, which issued during the prosecution of U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.
Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013 which issued during the prosecution of Applicant's PCT/IL2013/005069.
Naples GG et al., "A spiral nerve cuff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).

Baratta R et al., "Orderly stimulation of skeletal muscle motor units with tripolar nerve cuff electrode," IEEE Transactions on Biomedical Engineering, 36(8):836-43 (1989).
Van den Honert C et al., "Generation of unidirectionally propagated action potentials in a peripheral nerve by brief stimuli," Science, 206:1311-1312 (1979).
M. Devor, "Pain Networks", Handbook of Brand Theory and Neural Networks, Ed M.A. Arbib MIT Press pp. 696-701, 1998.
Epilepsy center. http://www.bcm.tmc.edu/neural/struct/epilep/epilpsy_vagus.html. May 31, 2011 (2 Versions).
J.F. Cortese, "Vagus Nerve Stimulation for Control of Intractable Epileptic Seizures", May 31, 2001.
Evetovich T.K. et al., Gender comparisons of the mechanomyographic responses to minimal concentric and eccentric isokinetic muscle actions, Medicine & Science in Sports & Exercise, 1998 pp. 1697-1702. Abstract.
An Office Action dated Dec. 5, 2013, which issued during the prosecution of U.S. Appl. No. 13/528,433.
An Office Action dated Sep. 30, 2013, which issued during the prosecution of U.S. Appl. No. 12/796,102.
Chow et al., Evaluation of Cardiovascular Stents as Antennas for Implantable Wireless Applications, IEEE Transactions on Microwave Theory and Techniques, vol. 57, No. 10, Oct. 2009.
Dean, J. et al., "Motor Pattern Generation", Handbook of Brain Theory and Neural Networks, pp. 696-701.
Hu et al., Percutaneous Biphasic Electrical Stimulation for Treatment of Obstructive Sleep Apnea Syndrome, IEEE Transactions on Biomedical Engineering, Jan. 2008 vol. 55 Issue:1 p. 181-187—an abstract.
A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009:148(5):315-9, 350, 349—an abstract.
Mortimer et al., Peripheral Nerve and Muscle Stimulation, Neuroprosthetics Theory and Practice, Chapter 4.2, 2004, P632-638.
Zabara J., Inhibition of experimental seizures in canines by repetitive vagal stimulation, Epilepsia. Nov.-Dec. 1992;33 (6):1005-12, http://www.ncbi.nlm.nih.gov/pubmed/1464256—an abstract.
A Notice of Allowance dated Jun. 9, 2014, which issued during the prosecution of U.S. Appl. No. 12/796,102.
An Office Action dated Sep. 26, 2013, which issued during the prosecution of U.S. Appl. No. 13/528,433.
An International Search Report and a Written Opinion both dated Jul. 11, 2013, which issued during the prosecution of Applicant's PCT/IL2013/050069.
An International Search Report and a Written Opinion both dated Apr. 29, 2014, which issued during the prosecution of Applicant's PCT/IB2013/060607.
An International Preliminary Report on Patentability dated Jul. 29, 2014, which issued during the prosecution of Applicant's PCT/IL2013/050069.
An International Preliminary Report on Patentability dated Jun. 9, 2015, which issued during the prosecution of Applicant's PCT/IB2013/060607.
A Notice of Allowance dated Apr. 25, 2014, which issued during the prosecution of U.S. Appl. No. 13/528,433.
Robert Szmurlo, Jacek Starzynski, Stanislaw Wincenciak, Andrzej Rysz, (2009) "Numerical model of vagus nerve electrical stimulation", COMPEL—The international journal for computation and mathematics in electrical and electronic engineering, vol. 28 Iss: 1, pp. 211-220.
Filiz, Sinan, et al. "Micromilling of microbarbs for medical implants."International Journal of Machine Tools and Manufacture 48.3 (2008): 459-472.
UCLA Team Reports Initial Success with Trigeminal Nerve Stimulation epilepsy. https://web.archive.org/web/20121020145122/https://www.epilepsy.com/epilepsy/newsletter/apr09_STIM.
An Office Action dated May 19, 2017, which issued during the prosecution of U.S. Appl. No. 14/935,941.
Notice of Allowance dated Sep. 1, 2017, which issued during the prosecution of U.S. Appl. No. 14/649,873.

(56) References Cited

OTHER PUBLICATIONS

An Office Action dated Feb. 27, 2017, which issued during the prosecution of U.S. Appl. No. 14/649,873.
An Office Action dated Apr. 5, 2017, which issued during the prosecution of U.S. Appl. No. 14/374,375.
European Search Report dated Feb. 3, 2017, which issued during the prosecution of Applicant's European App No. 16196878.9.

* cited by examiner

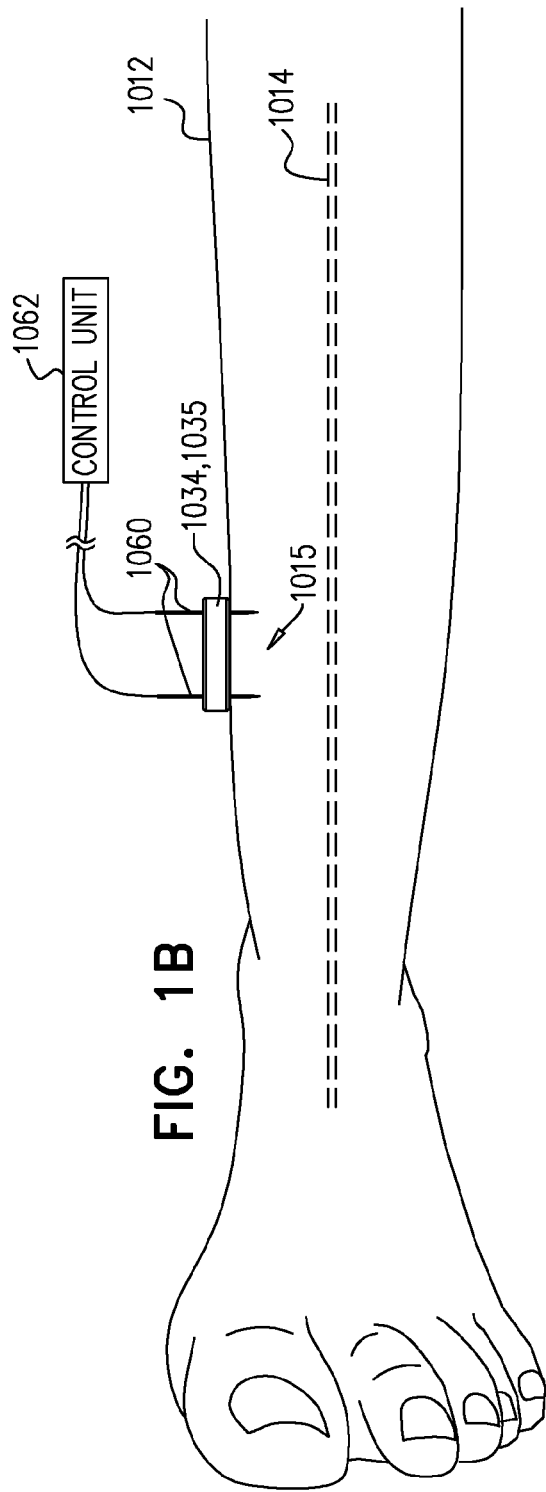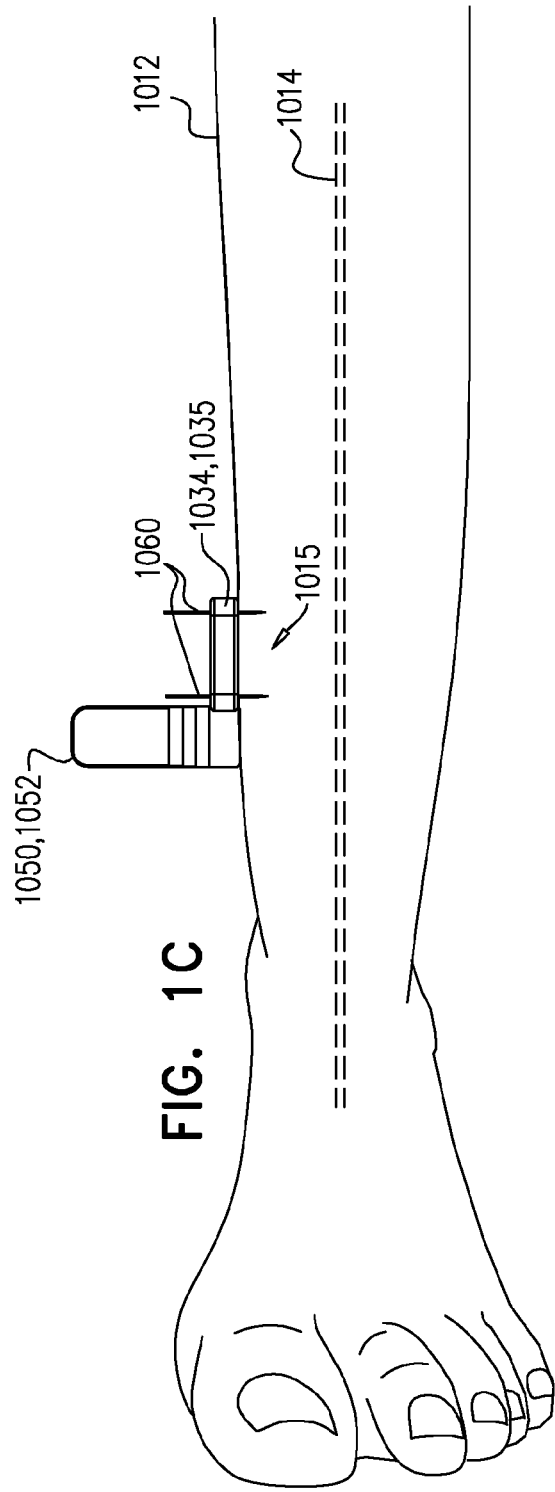

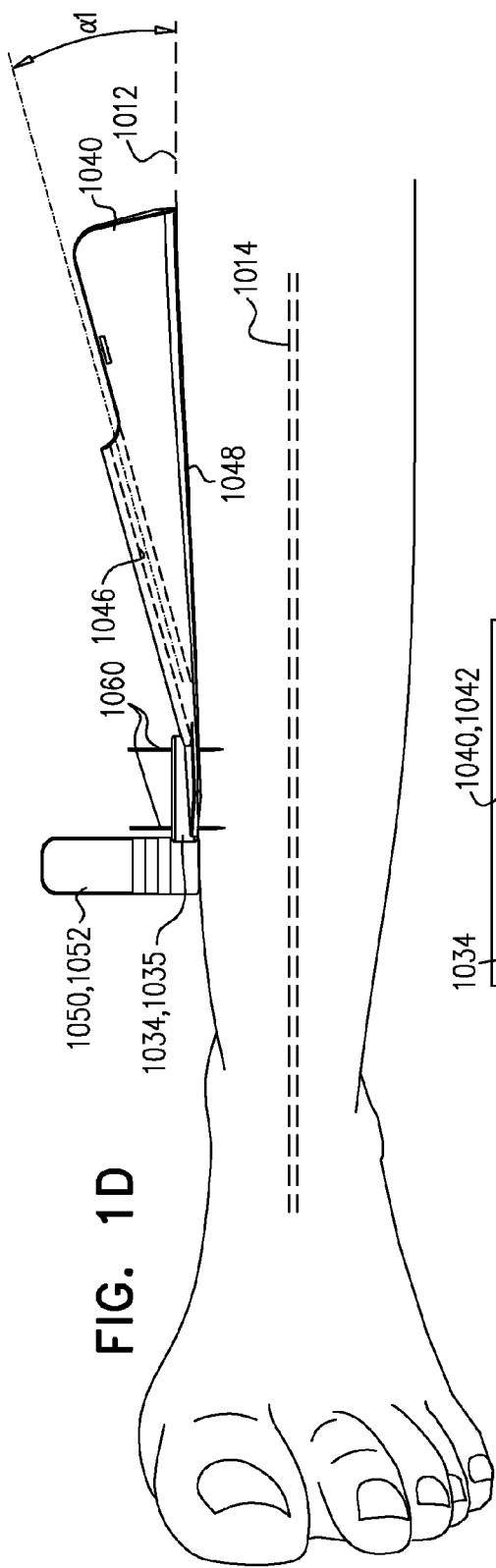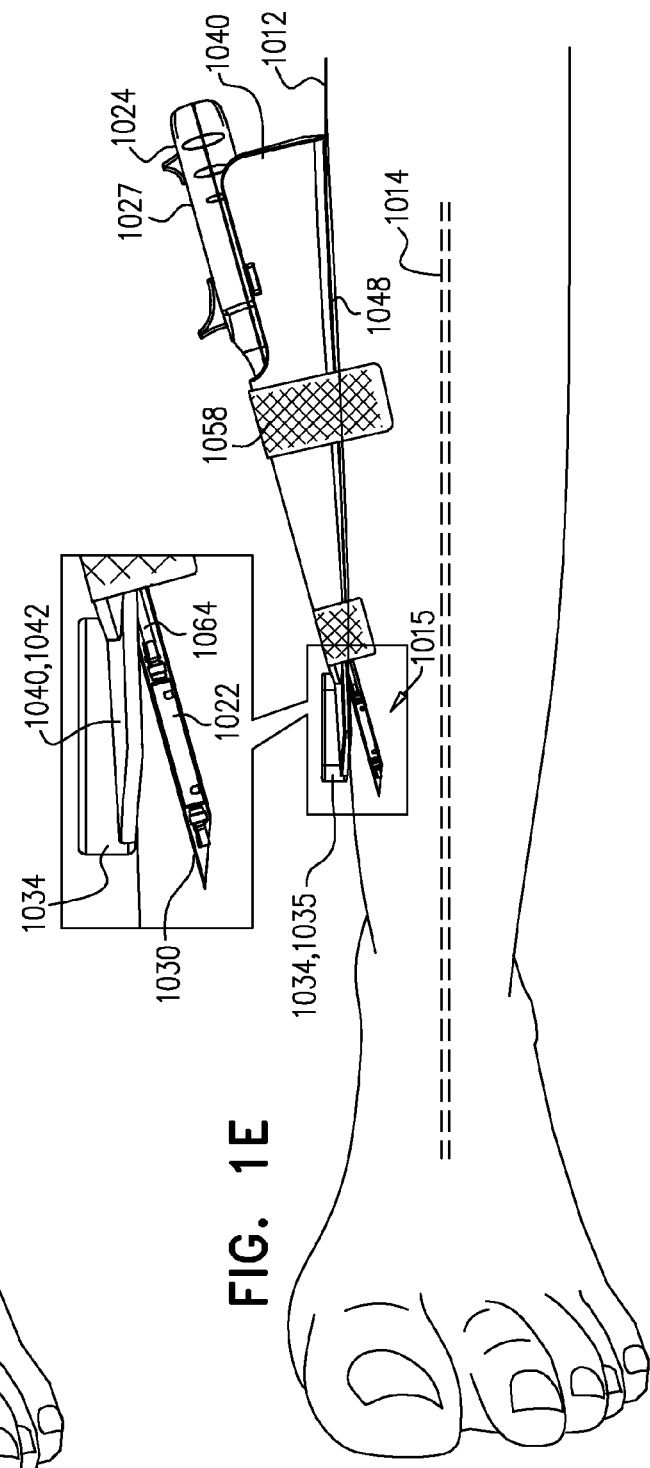

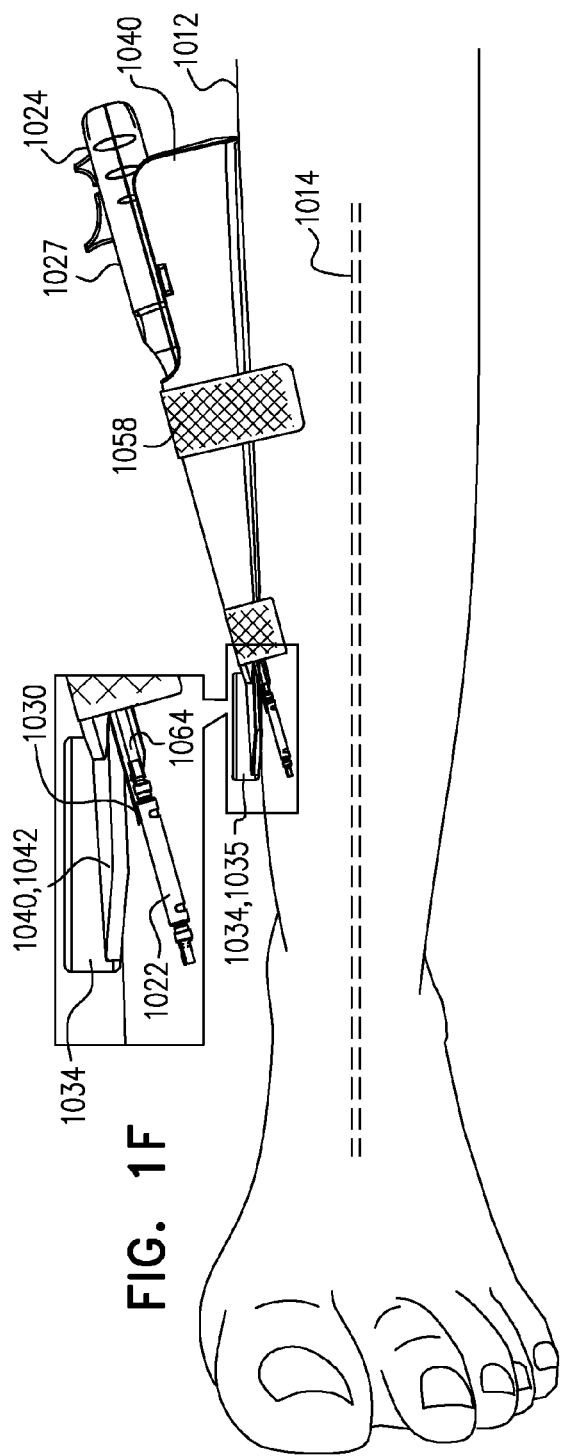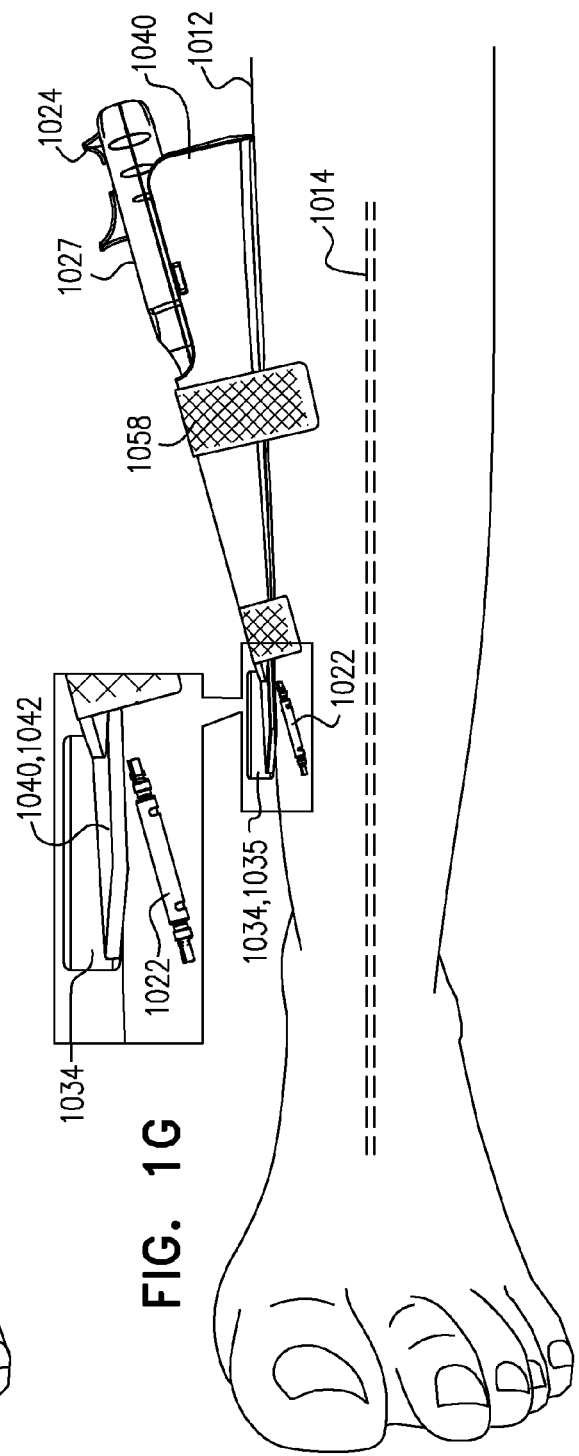

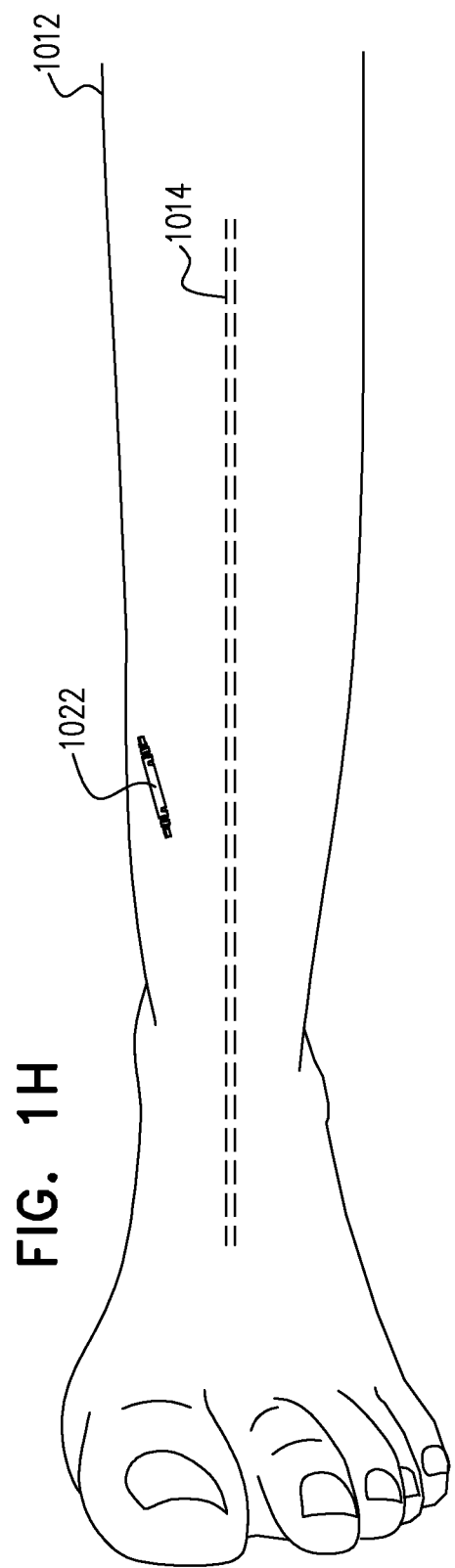

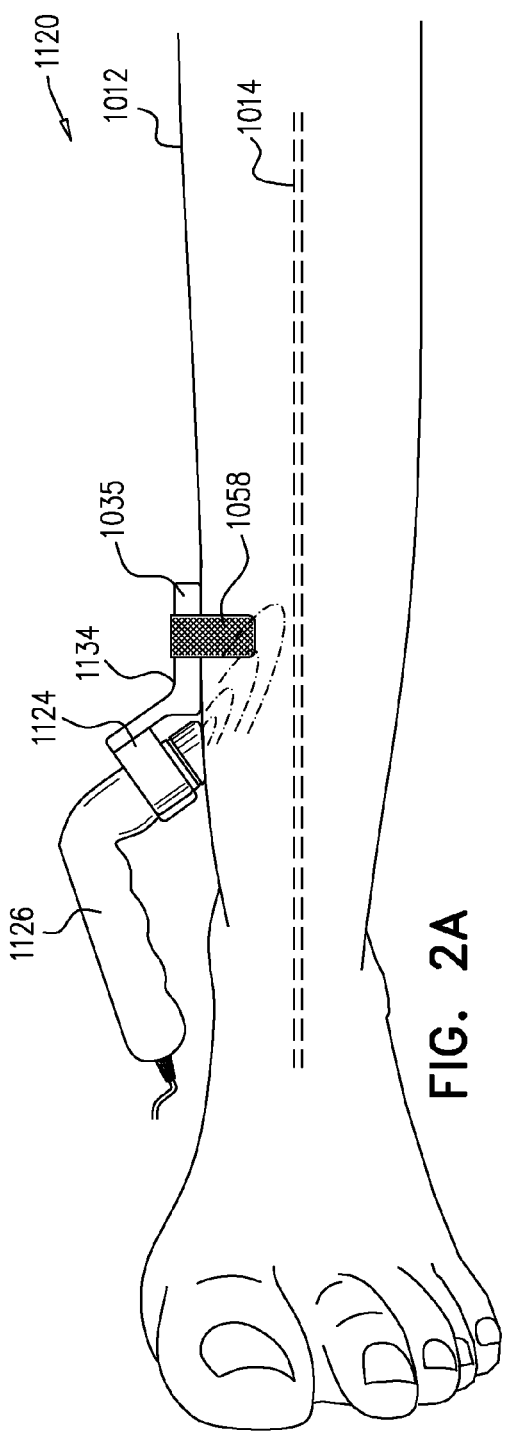
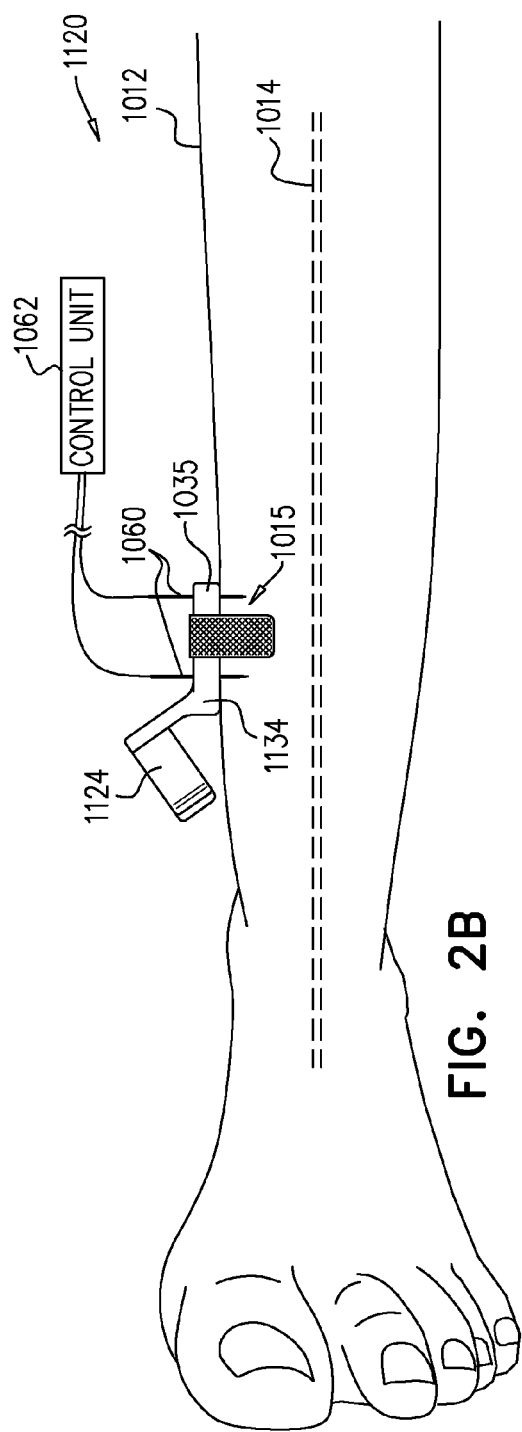

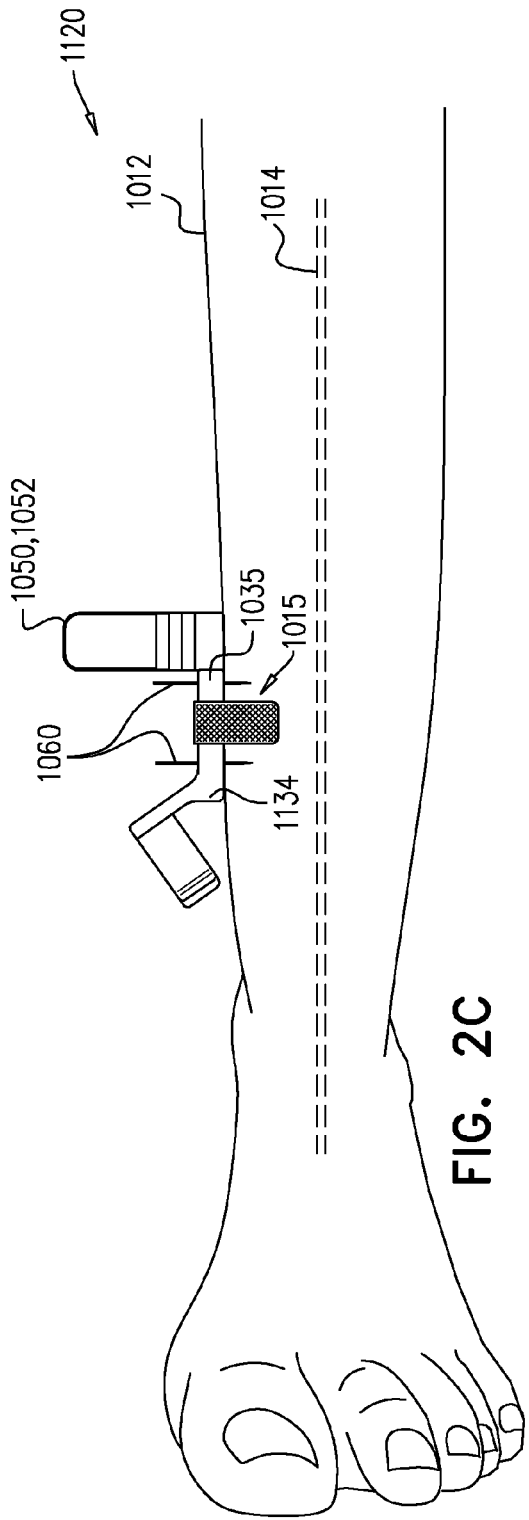
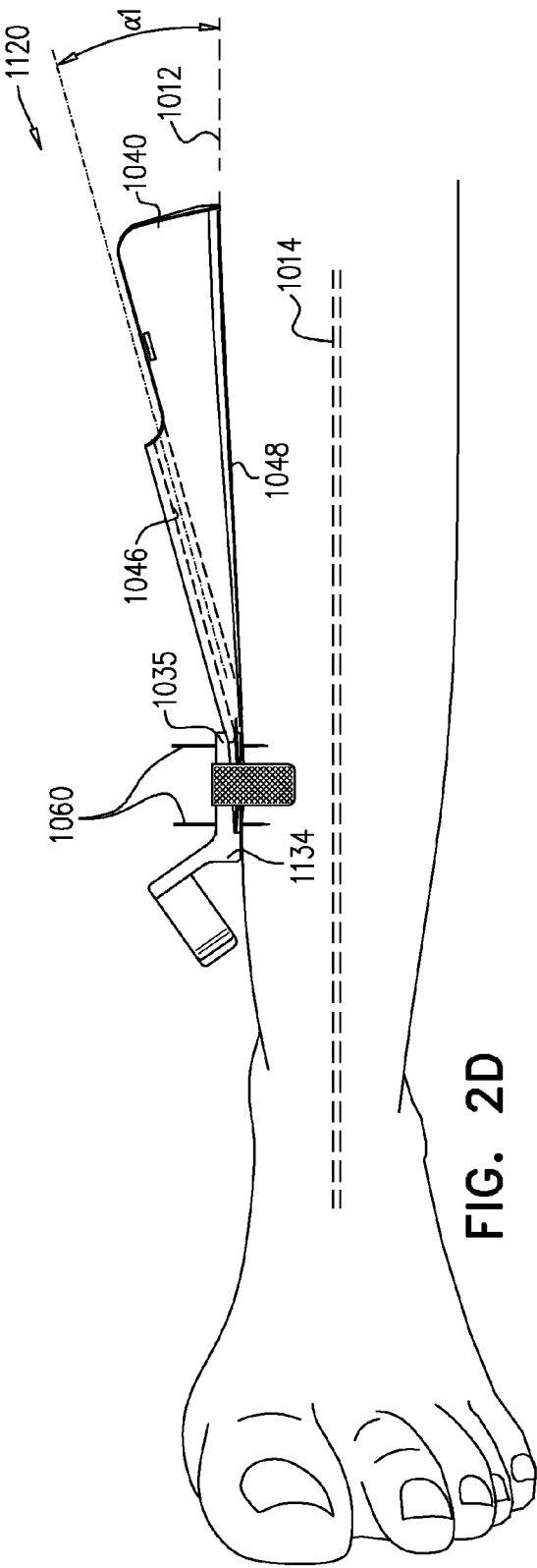

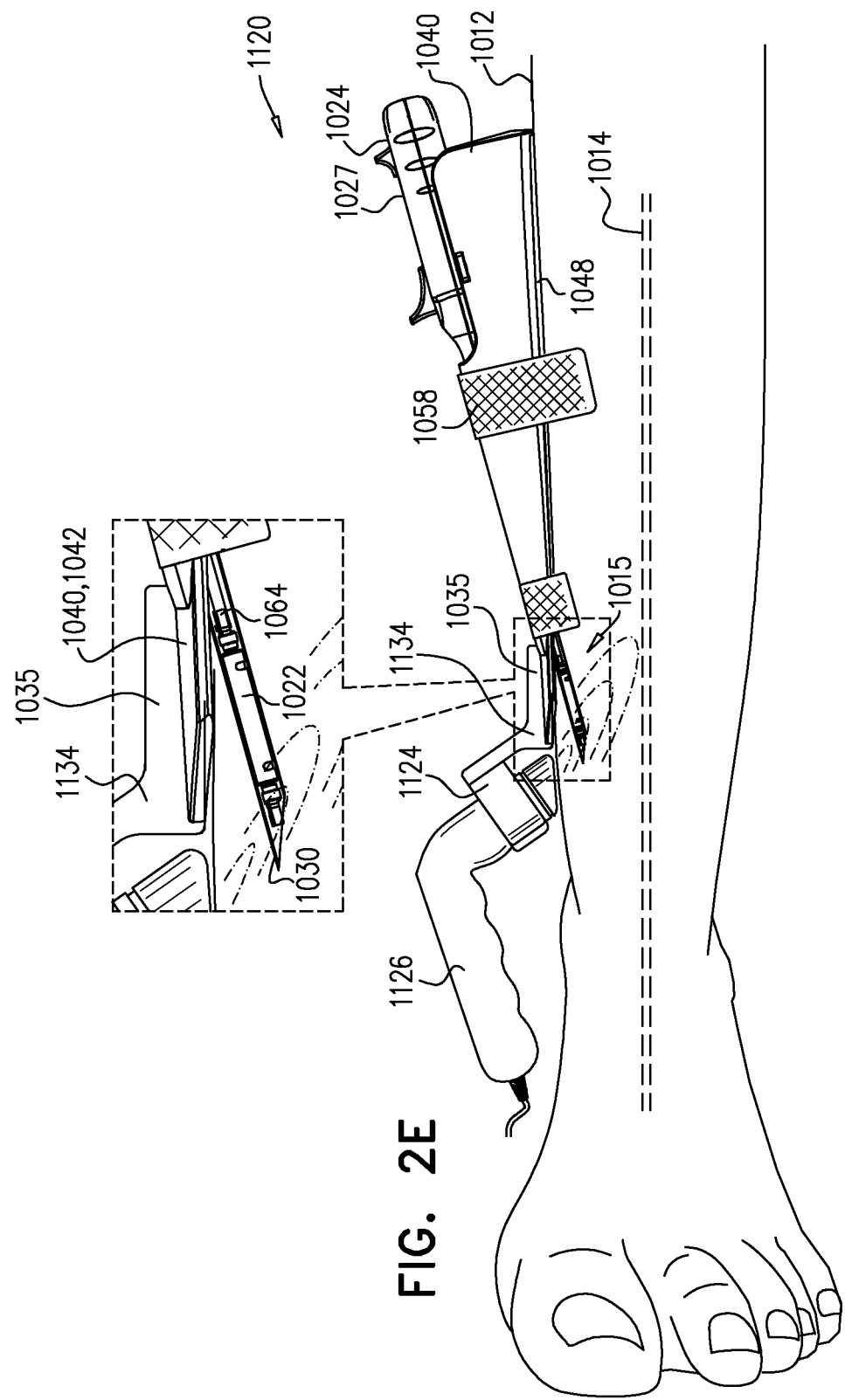

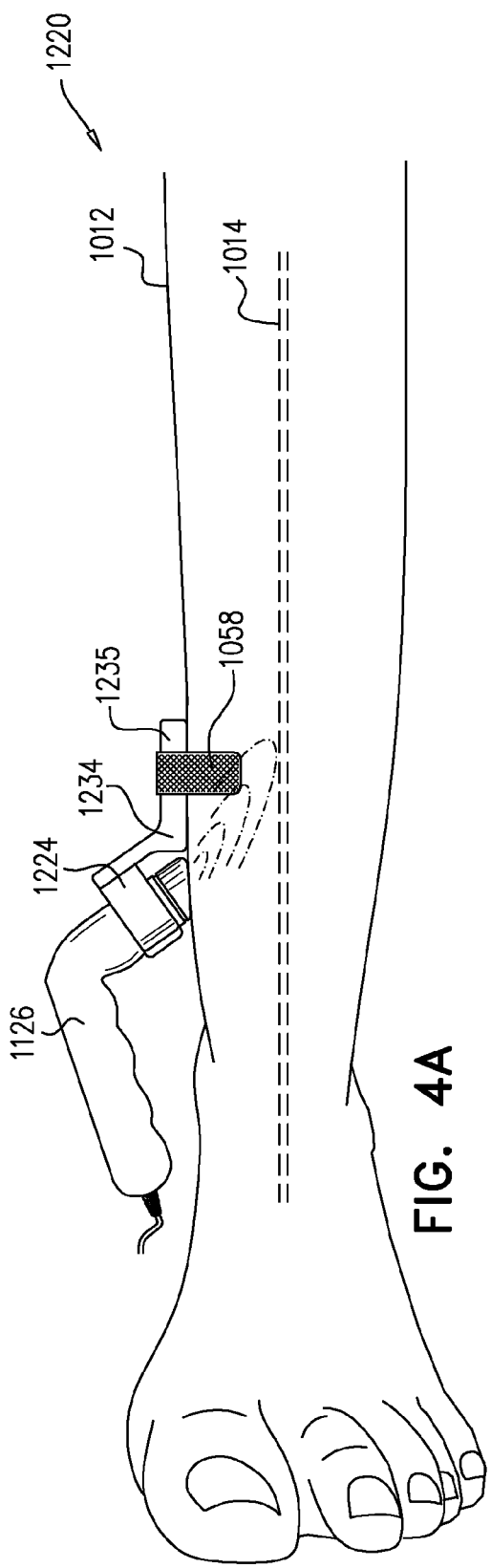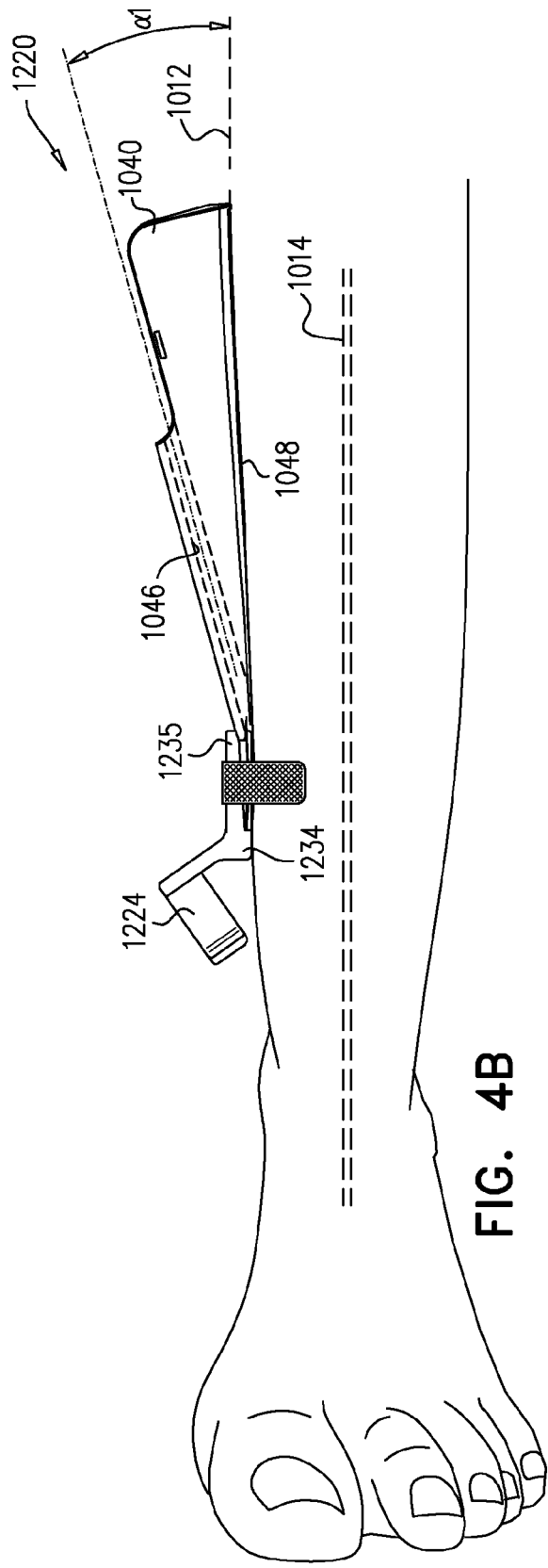
FIG. 4A
FIG. 4B

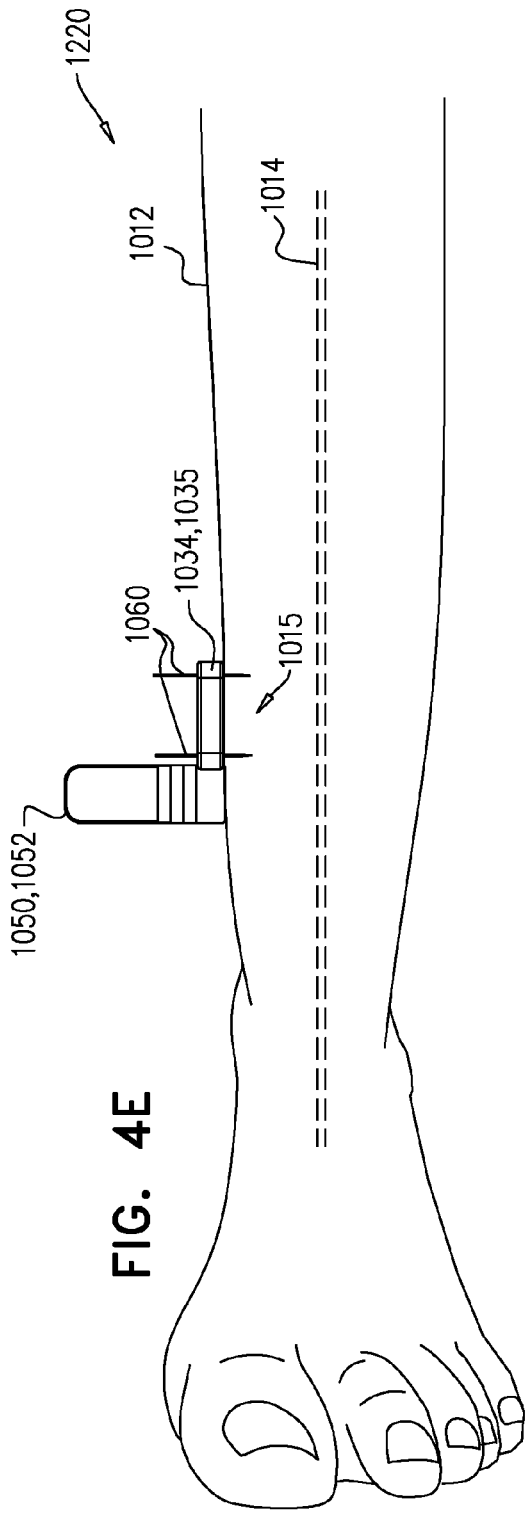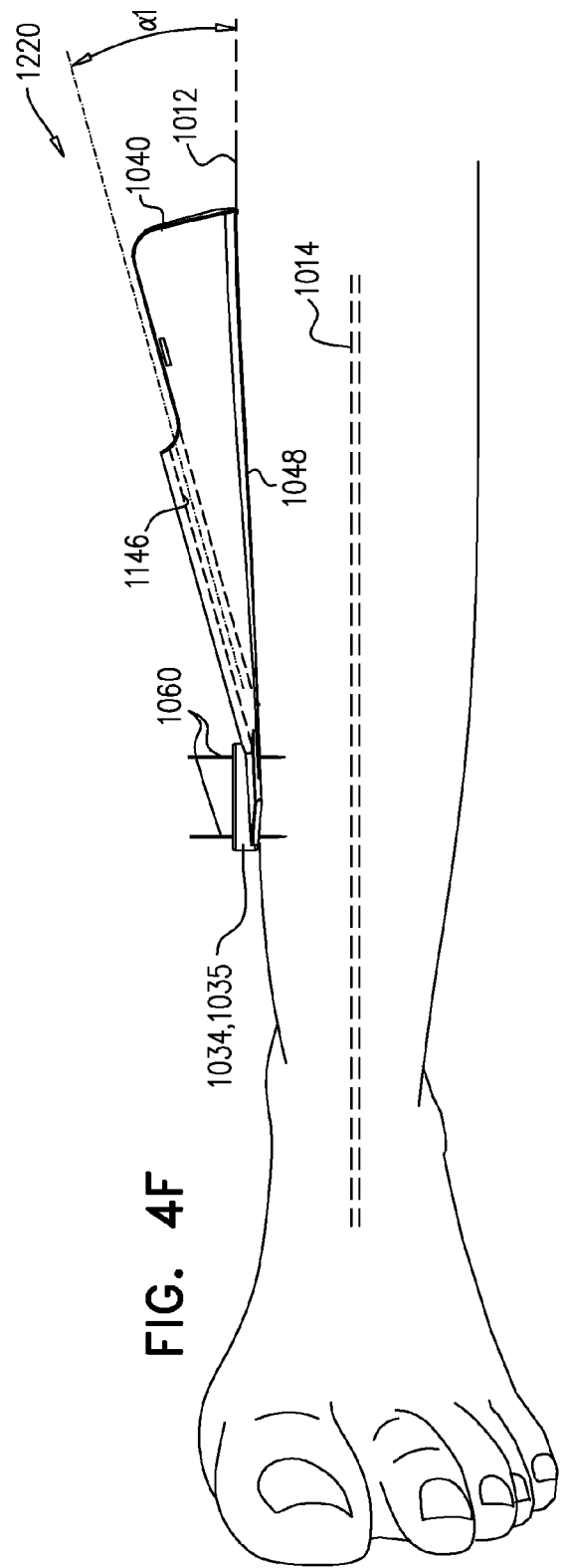

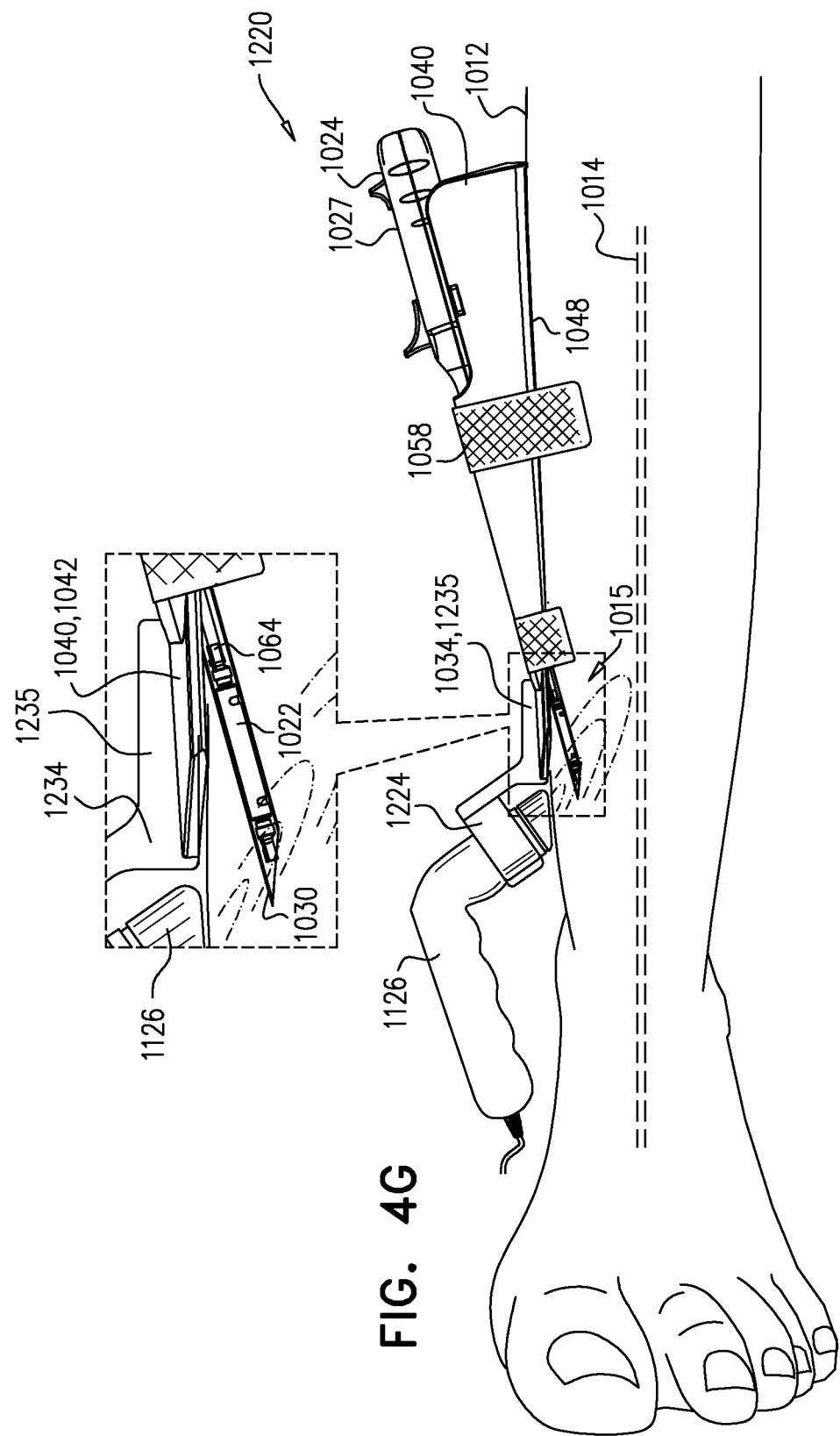

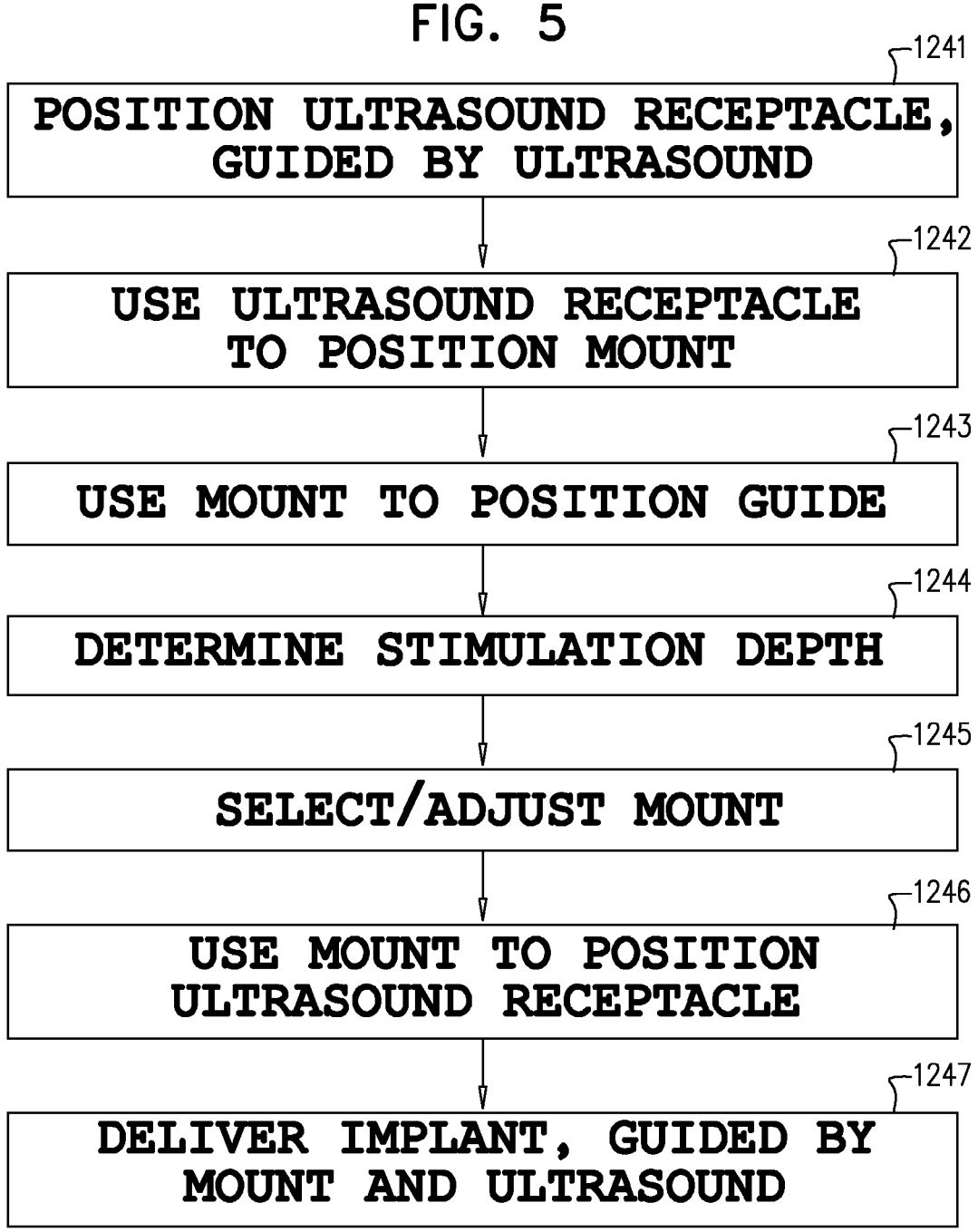

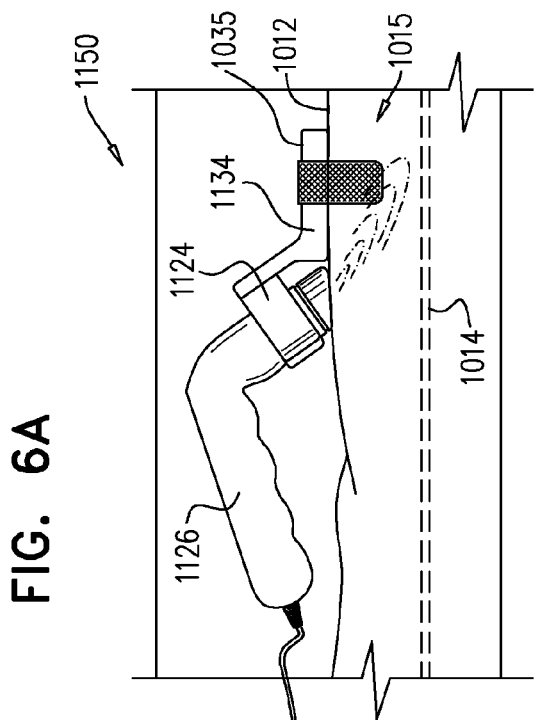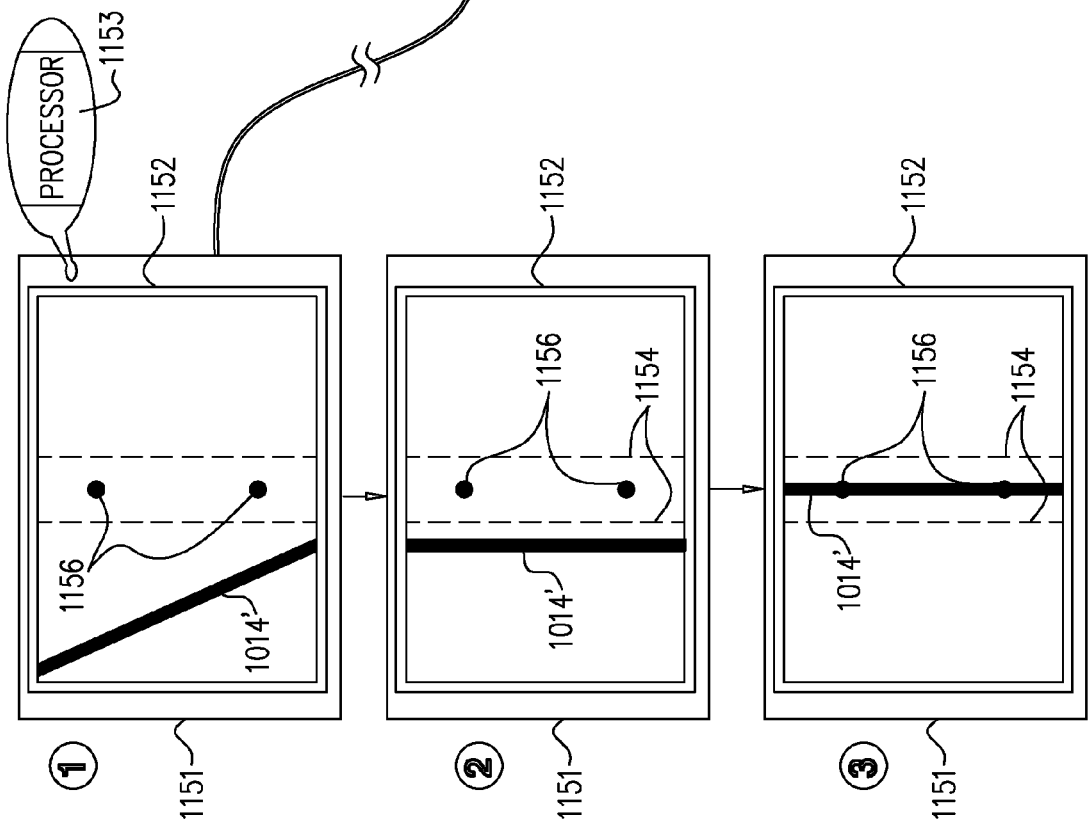
FIG. 6A

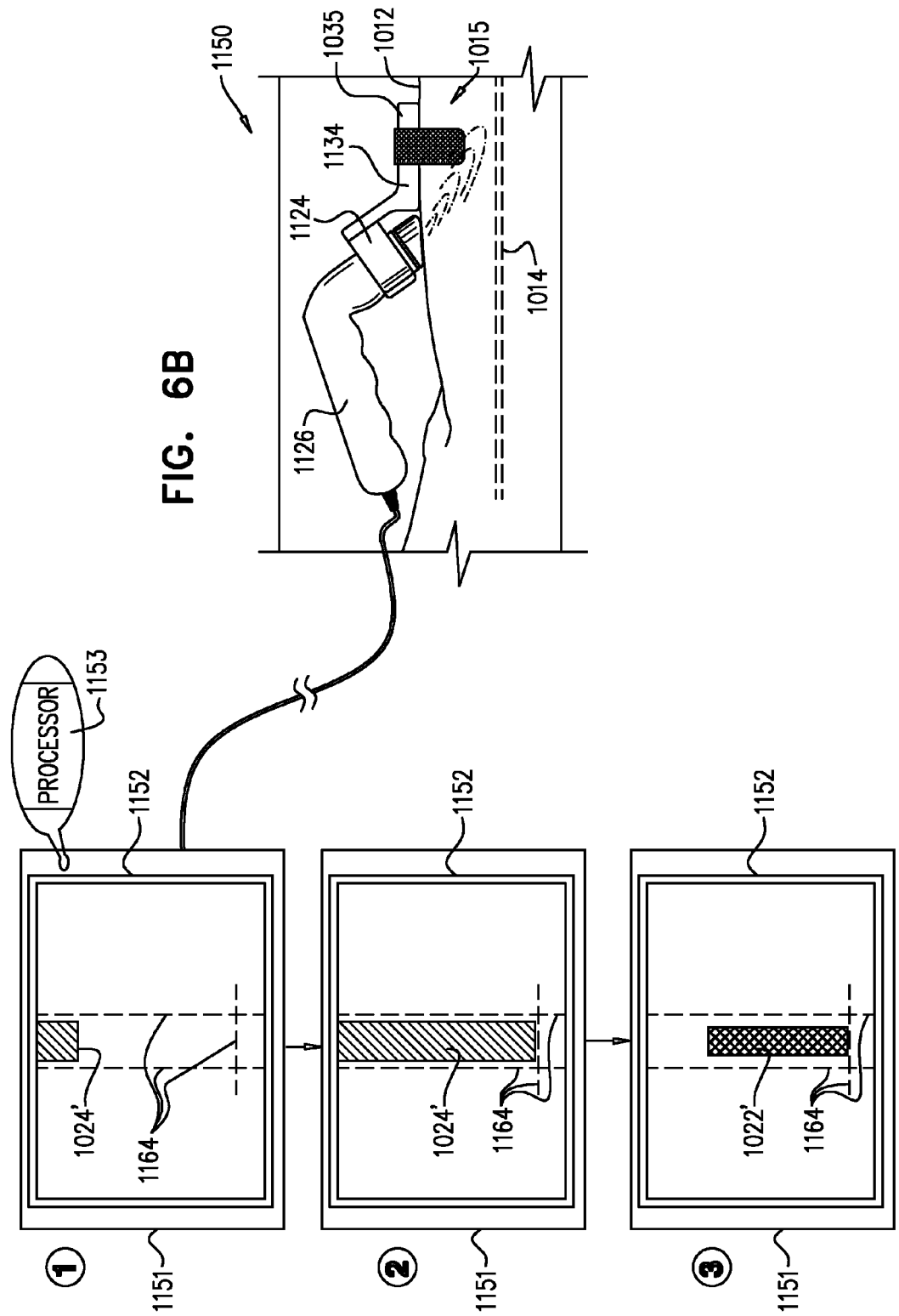

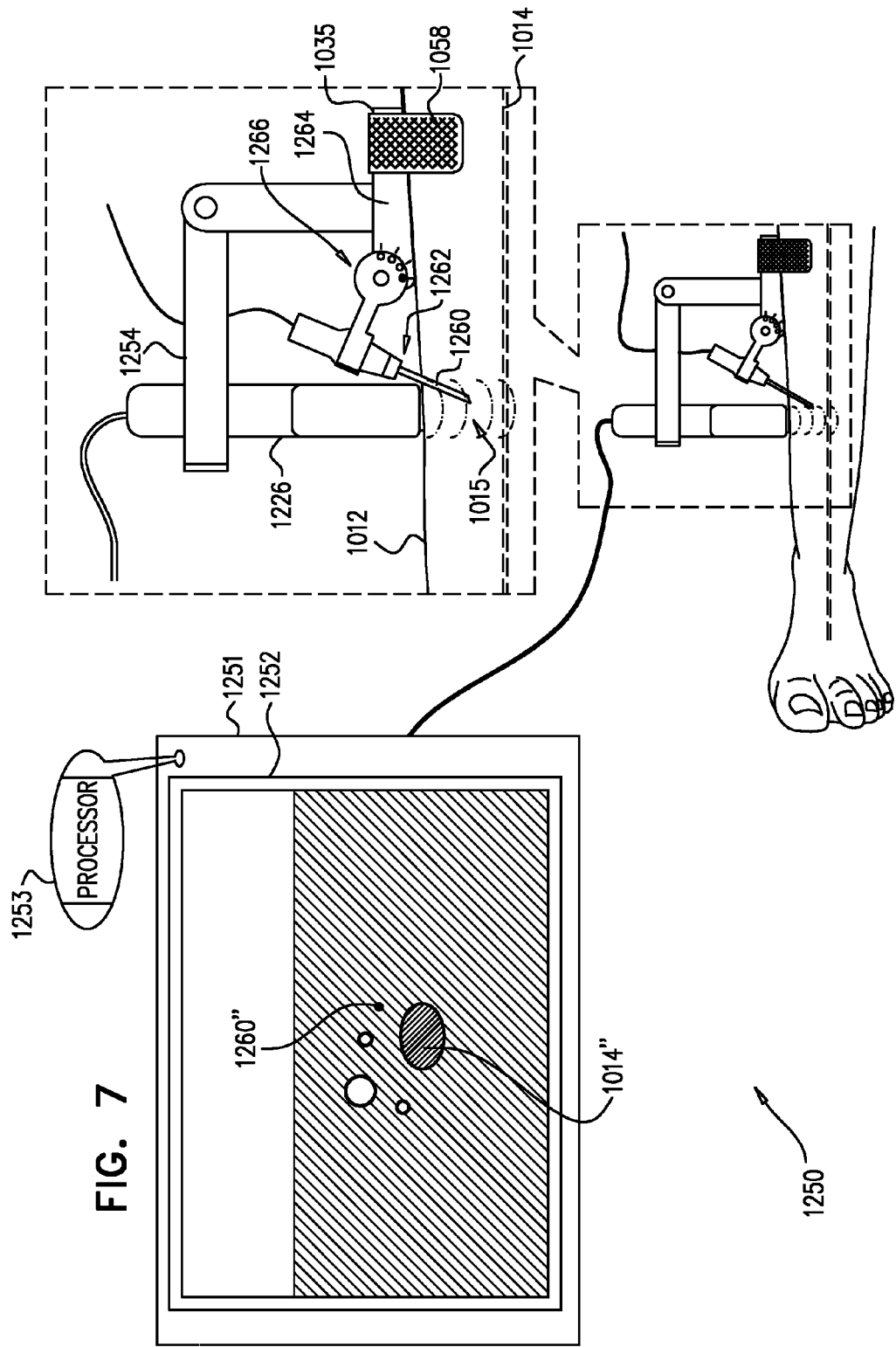

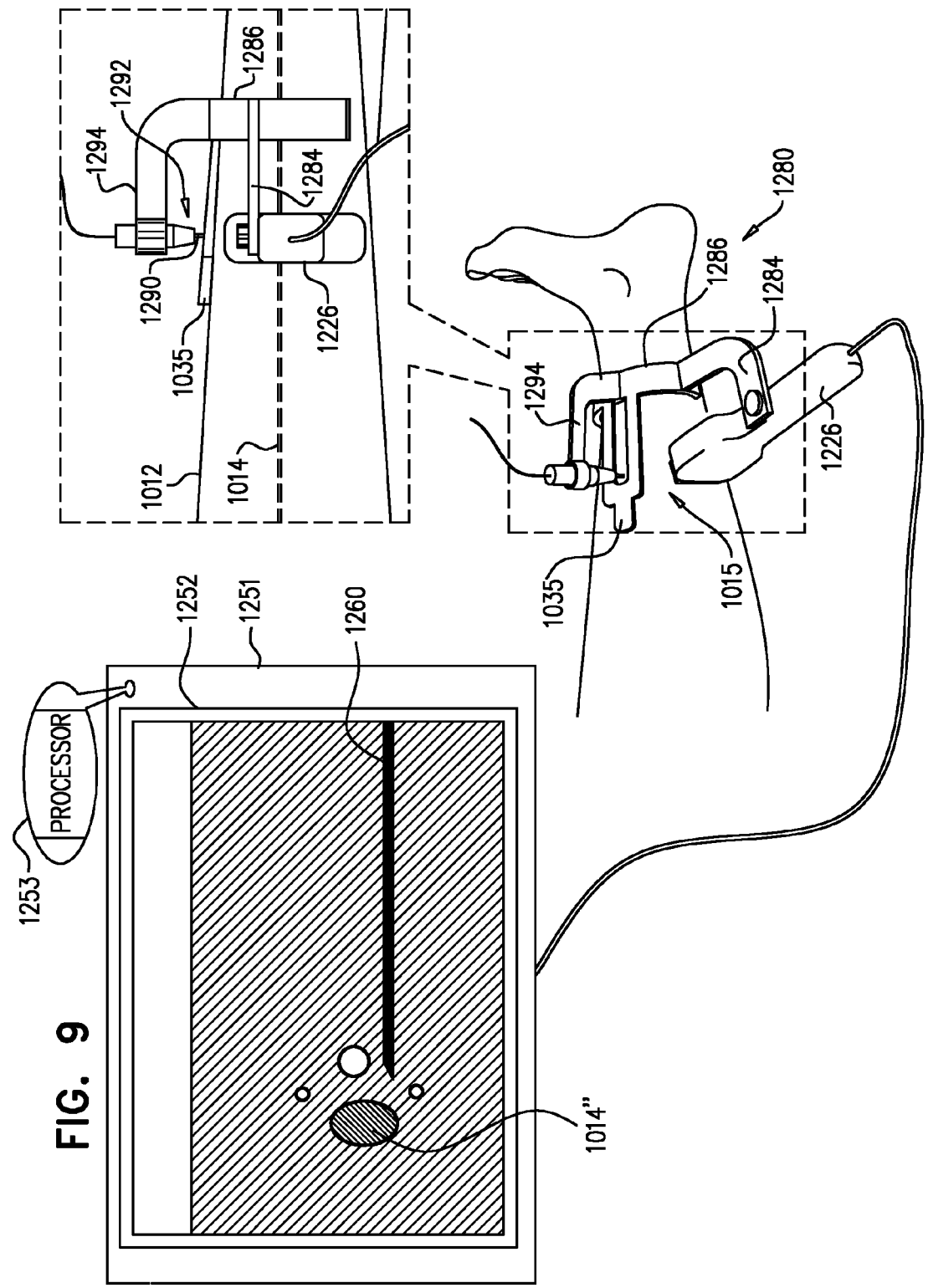

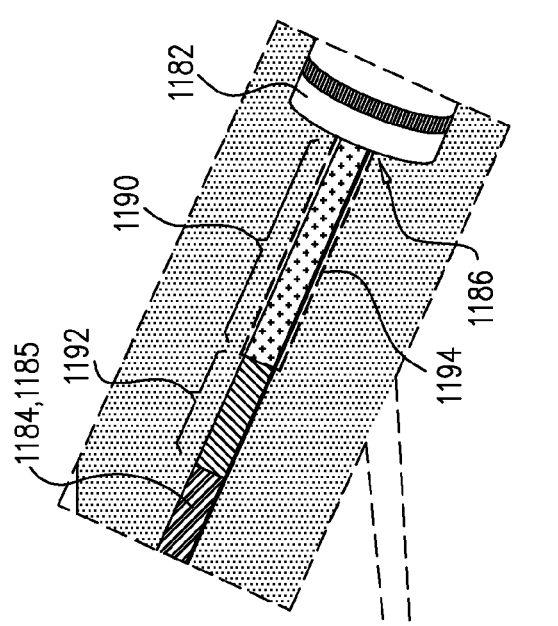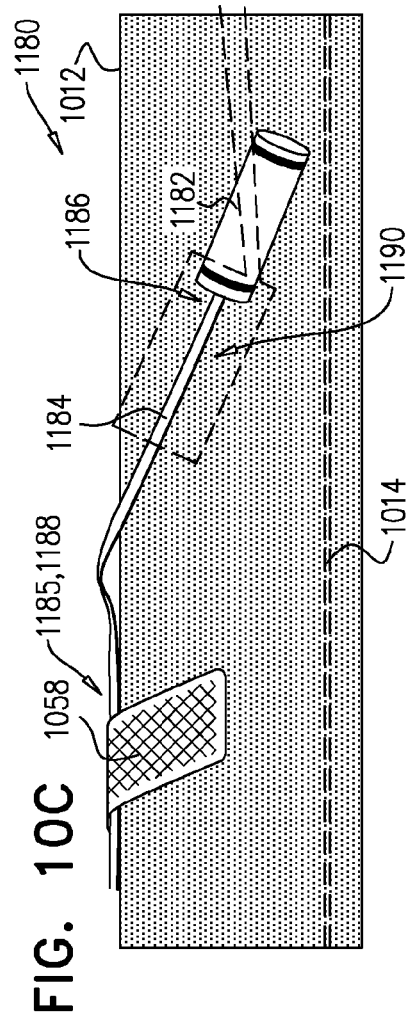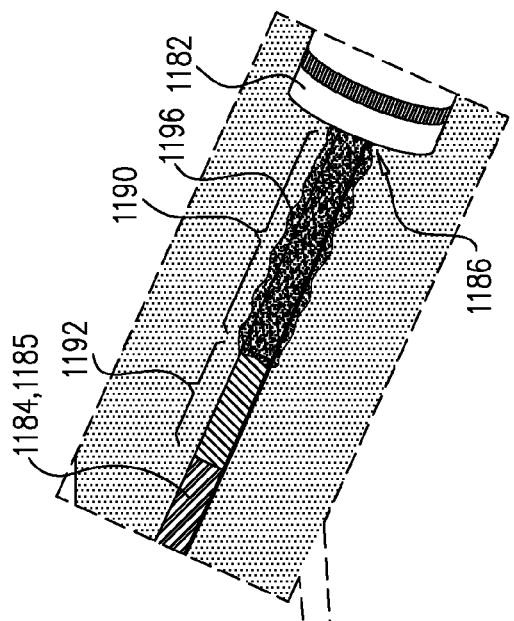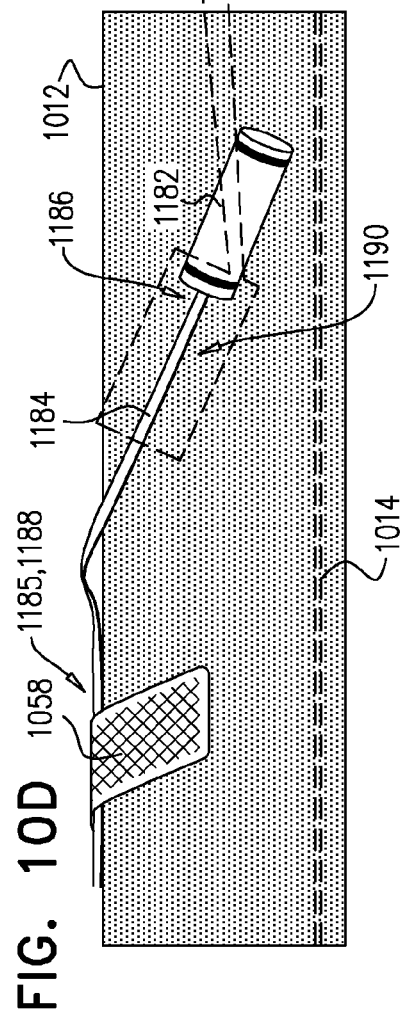

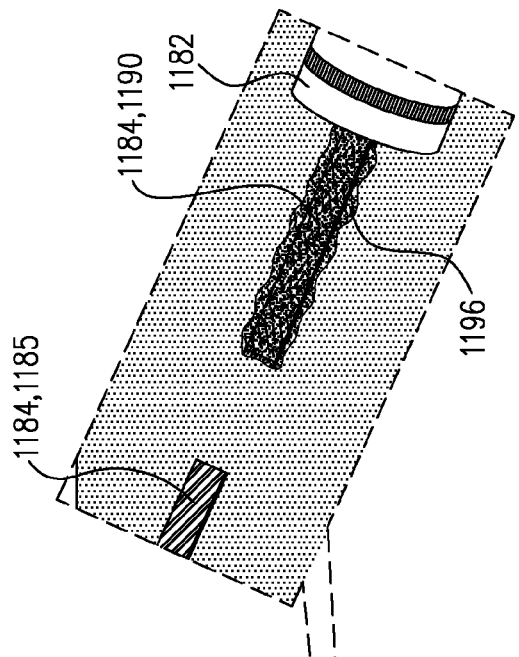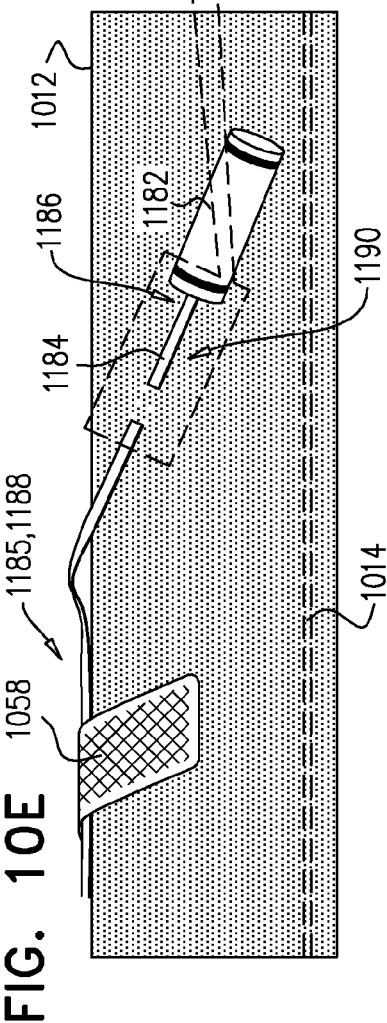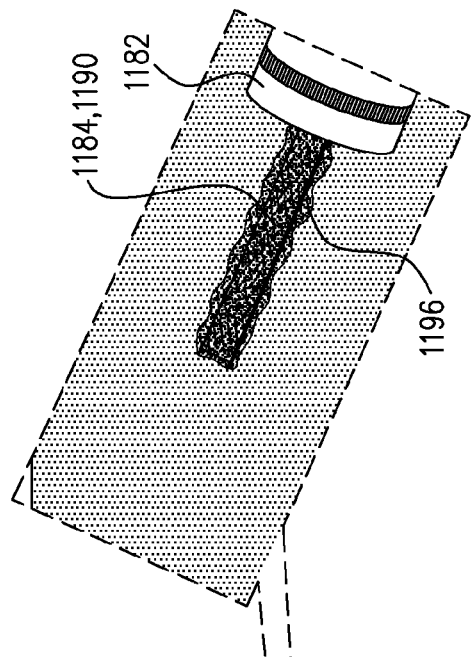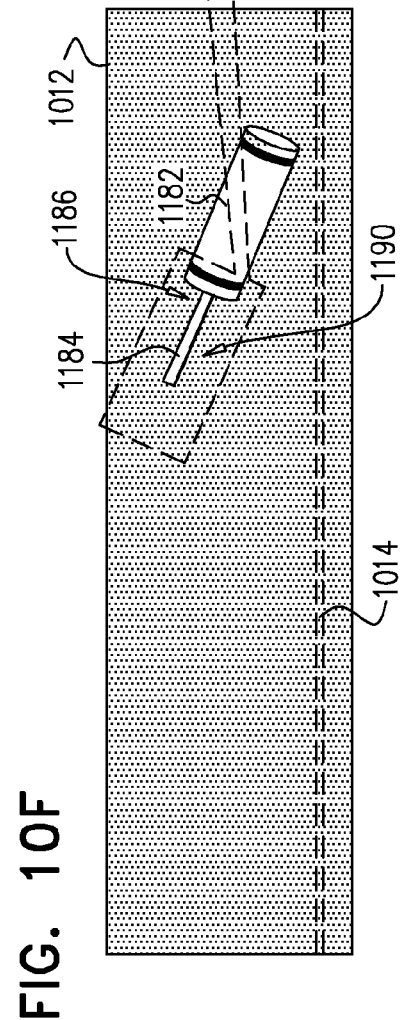
FIG. 10E
FIG. 10F

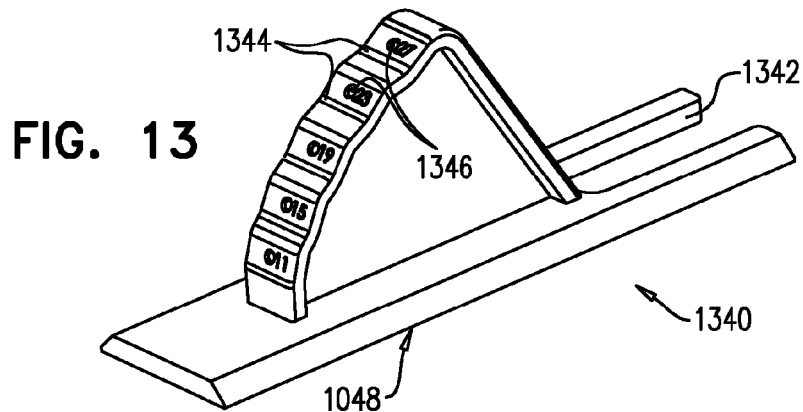
FIG. 13
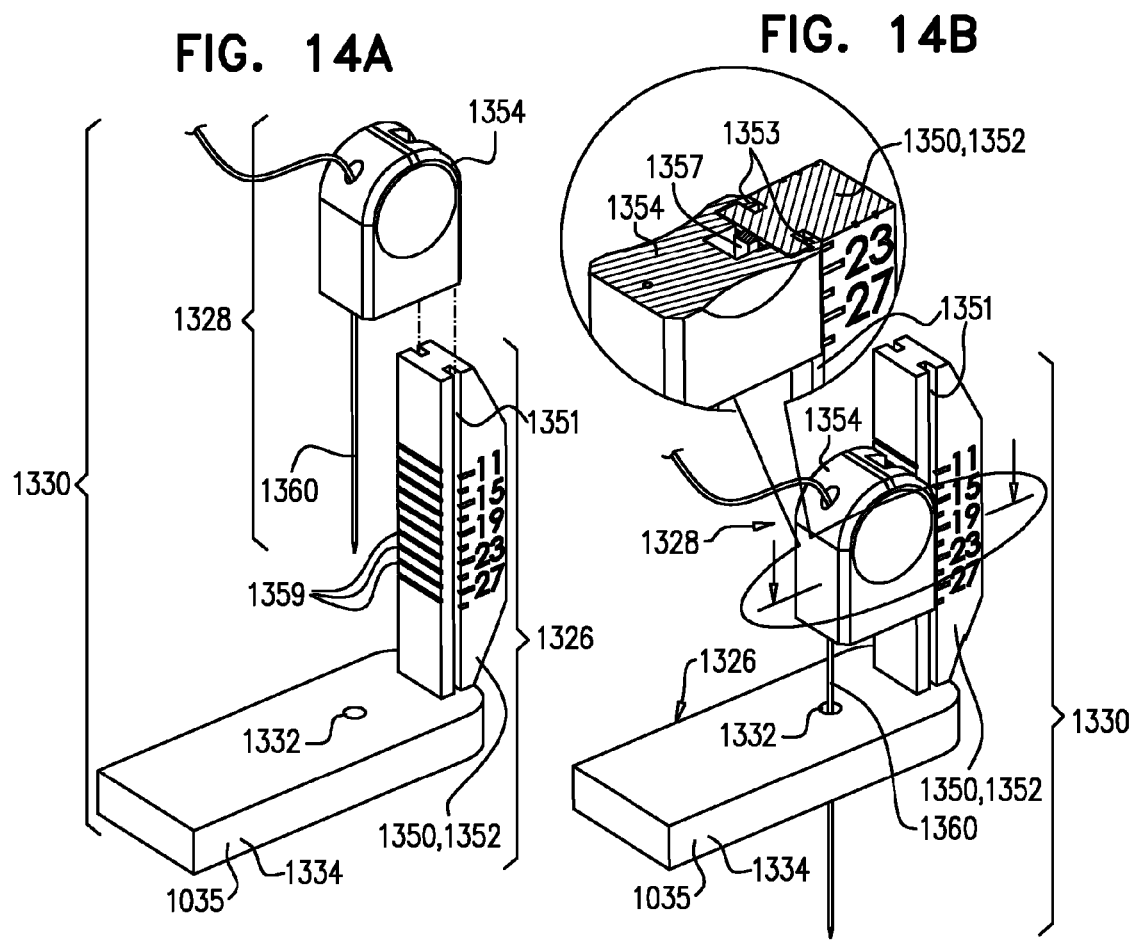
FIG. 14A
FIG. 14B

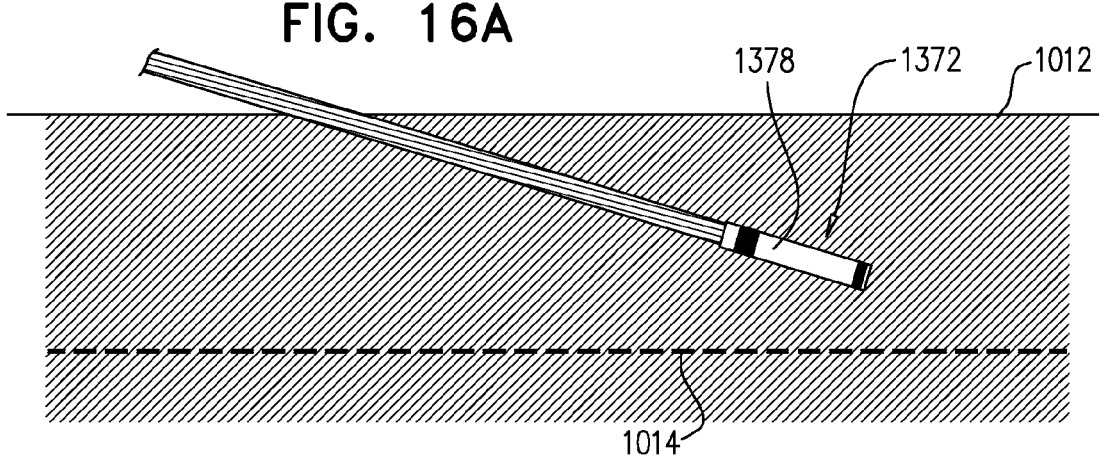
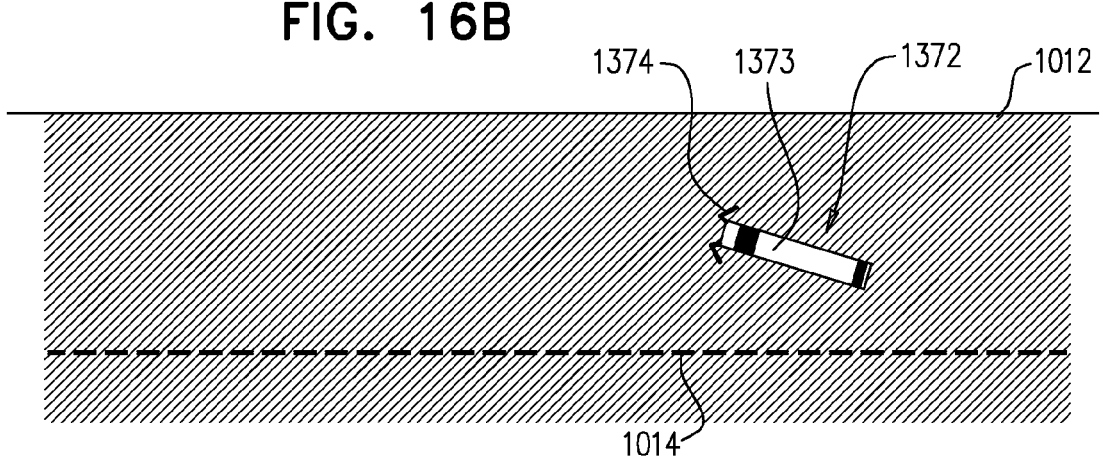

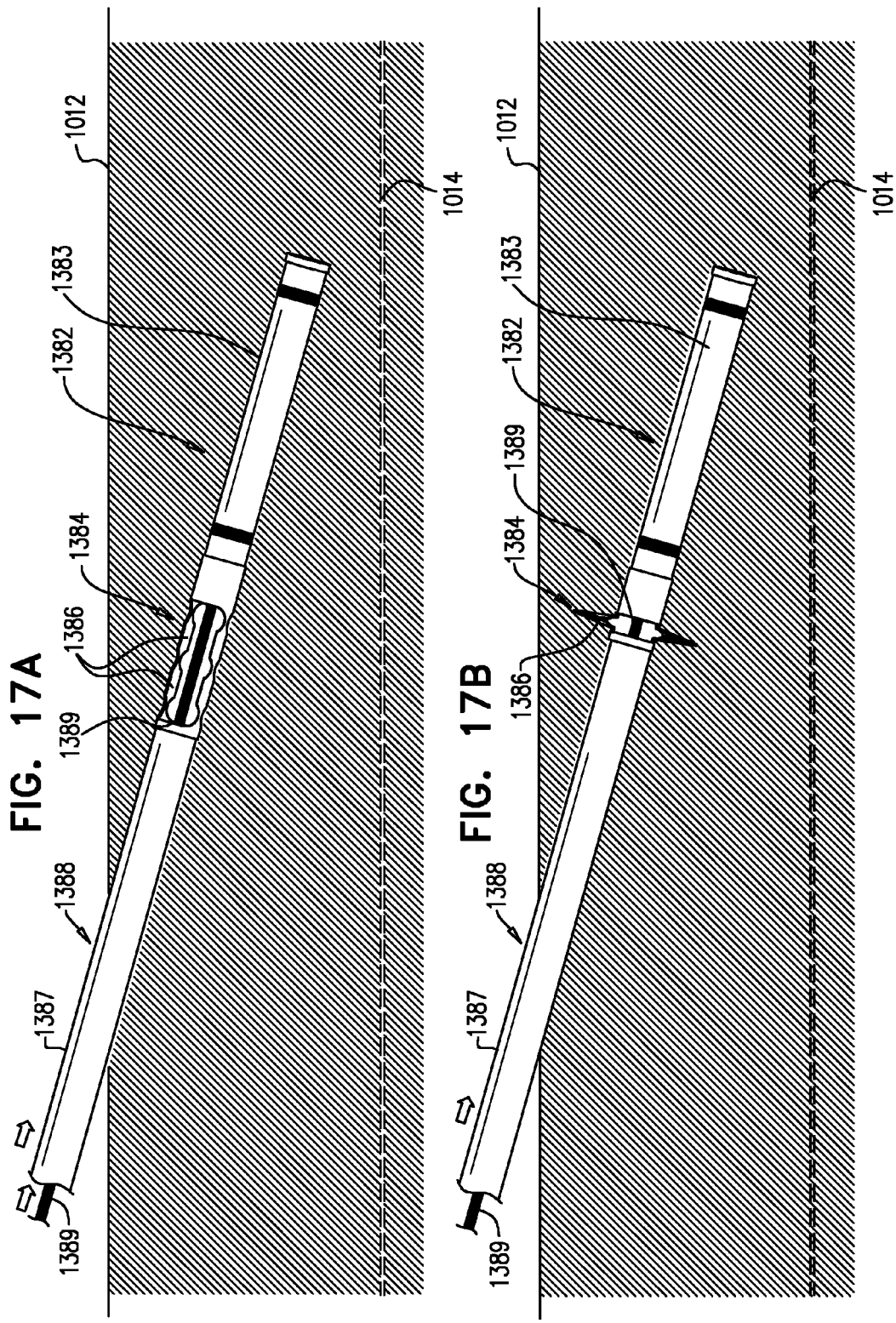

ANCHORS AND IMPLANT DEVICES

CROSS-REFERENCES TO RELATED APPLICATIONS

The present patent application is related to the following applications, filed on even date herewith:

(a) PCT Application IB2013/060607 to Gross et al., filed Dec. 3, 2013, entitled "Delivery of Implantable Neurostimulators," and which published as WO 2014/087337;

(b) A US Patent Application to Oron et al., filed on even date herewith, and entitled "Extracorporeal Implant Controllers", which received U.S. Ser. No. 14/601,626, and which published as US 2016/0206890; and (c) A US Patent Application to Plotkin et al., filed on even date herewith, and entitled "Transmitting Coils for Neurostimulation", which received Ser. No. 14/601,568, and which published as US 2016/0206889.

All of the above-mentioned applications are assigned to the assignee of the present application and incorporated herein by reference.

FIELD OF THE INVENTION

Some applications of the present invention relate in general to medical devices. More specifically, some applications of the present invention relate to percutaneous implants.

BACKGROUND

Neurological disorders affect the nerves, muscles or the brain. Many neurological disorders reduce or eliminate voluntary recruitment of muscles, which may result in loss of ability to perform motor tasks or to maintain systems that depend on muscle activity for their function. Many neurological disorders cause pain.

Neurostimulation is a clinical tool used to treat various neurological disorders. This technique involves modulation of the nervous system by electrically activating fibers in the body. Percutaneous implants exist for providing neurostimulation.

SUMMARY OF THE INVENTION

For some applications of the invention, apparatus and techniques are described for percutaneous delivery of an implant. For some applications, apparatus and techniques are provided for identifying a target site for the implantation of a percutaneously-implantable neurostimulatory implant, and/or delivering the implant to the identified target site. For some applications, the apparatus and techniques facilitate implanting the implant at a given orientation with respect to the tissue in which the implant is implanted. For some applications, the apparatus and techniques facilitate anchoring the implant to the tissue in which the implant is implanted.

For some applications, a guide is provided that is placeable on the skin of the subject, and defines at least one channel through which a needle electrode is advanceable into tissue below the skin. The needle electrode is used to identify the depth at which a desired effect is achieved, and therefore at which the implant should be implanted—i.e., the target site. A mount, also placeable on the skin, is used to guide an implant-delivery tool through the skin and to the target site, responsively to the identified target site (e.g., the depth thereof). The mount typically defines a lumen through which the implant-delivery tool is advanced, the lumen being disposed at a particular angle with respect to a skin-contacting surface of the mount.

Various options are described for the mount guiding the tool responsively to the identified target site. For some applications, the mount used is selected from a plurality of mounts, the lumen of each mount being disposed at a respective different angle with respect to the skin-contacting surface of that mount. For some applications, the angle at which the lumen is disposed is adjustable, and is adjusted responsively to the identified target site. For some applications, the mount used defines a plurality of lumens, each disposed at a respective different angle with respect to the skin-contacting surface, and based on the identified target site, the user selects a particular lumen through which to advance the implant-delivery tool.

For some applications, a receptacle, coupled to another element of the apparatus, is provided. The receptacle is shaped to receive and be coupled to an ultrasound transceiver, such that a field of view of the ultrasound transceiver includes the target site.

For some applications, a tether, coupled to the implant, is configured to temporary facilitate retrievability of the implant by pulling on the tether. After a period of the implant being disposed in the tissue of the subject, attachment of a distal portion of the tether to a proximal portion of the tether becomes weaker. For some such applications, the tether is further configured to facilitate anchoring of the implant, by the distal portion of the tether serving as an anchor.

For some applications, an implant has an anchor at a proximal half, but not at a distal half, thereby facilitating placement of the distal half close to a nerve of the subject.

For some applications, an implant has a distal electrode that has a smaller surface area than that of a proximal electrode of the implant.

For some applications, an implant is advanceable into tissue while disposed outside of any delivery tube.

There is therefore provided, in accordance with an application of the present invention, apparatus including an implant, the implant including:
  a rod-shaped housing, having a distal half and a proximal half, and configured to be injected distally into tissue of a subject;
  a cathode on the distal half of the housing;
  an anchor configured to protrude from the proximal half of the housing, no anchor being configured to protrude from the distal half of the housing;
  an anode; and
  circuitry disposed within the housing, configured to drive a current between the cathode and the anode.

In an application, the anode is disposed at a site of the housing that is between the cathode and the anchor.

In an application, the anode is disposed on the proximal half of the housing.

In an application, the anchor includes the anode.

In an application, the anode has a larger surface area than the cathode.

In an application, the apparatus further includes an antenna configured to receive wirelessly-transmitted power, and the circuitry is configured to use the received power to drive the current between the cathode and the anode.

In an application, the antenna is disposed within the housing.

In an application, the antenna is disposed between the anode and the cathode.

In an application, the antenna is disposed proximal to the anode.

In an application, the apparatus further includes a delivery tube, and:
the implant is configured to be injected distally into the tissue by being disposed, in a delivery state, within the delivery tube with the distal half of the housing disposed closer to a distal opening of the delivery tube than is the proximal half of the housing,
in the delivery state the anchor is in a restrained state thereof, and
the anchor is configured to automatically expand away from the housing upon deployment from the delivery tube.

There is further provided, in accordance with an application of the present invention, a method for use with a subject, the method including:
injecting, via a delivery tube, an implant including a rod-shaped housing into a subject such that an electrode disposed at a distal half of the housing is disposed 0.1-5 mm from of a nerve of the subject, and an anchor disposed at a proximal half of the housing is disposed 8-15 mm from the nerve of the subject; and
anchoring the anchor to tissue of the subject (i) by facilitating protrusion of the anchor from the proximal half of the housing such that it inhibits movement of the electrode with respect to the nerve, and (ii) without facilitating protrusion of any anchor from the distal half of the housing.

In an application, the electrode is a cathode, the anchor serves as an anode, and anchoring the anchor includes anchoring the anchor that serves as the anode.

In an application, injecting the implant includes exposing the electrode from a distal end of the delivery tube, and anchoring the anchor includes, subsequently to exposing the electrode from the delivery tube, exposing the anchor from the distal end of the delivery tube such that the anchor automatically expands away from the housing.

In an application, the electrode is a cathode, the implant includes an anode at a site of the housing that is between the cathode and the anchor, and the method includes exposing the anode from the distal end of the delivery tube (i) after exposing the cathode from the distal end of the delivery tube, and (ii) before exposing the anchor from the delivery tube.

In an application, the anode is disposed on the proximal half of the housing, and exposing the anode from the distal end of the delivery tube includes exposing the anode from the distal end of the delivery tube subsequently to exposing the distal half of the implant from the distal end of the delivery tube.

In an application, the implant includes an antenna configured to receive wirelessly-transmitted power, and injecting the implant includes injecting the implant that includes the antenna.

There is further provided, in accordance with an application of the present invention, a method for use with a subject, the method including:
providing an implant that includes: (i) a rod-shaped housing having a distal end and a proximal end, (ii) a cathode disposed on the housing, and having a cathode-surface area, (iii) an anode, disposed on the housing at a site that is closer to the proximal end than is the cathode, and having an anode-surface area that is greater than the cathode-surface area, and (iv) circuitry disposed within the housing, and configured to drive a current between the cathode and the anode;
percutaneously introducing the implant, distal-end first, into tissue of the subject; and
positioning the implant such that (i) when the circuitry drives the current between the cathode and the anode, the current is applied to a nerve of the subject, and (ii) the cathode is closer to the nerve than is the anode.

In an application:
the rod-shaped housing has a distal half and a proximal half,
the implant includes an anchor configured to protrude from the proximal half, and no anchor configured to protrude from the distal half, and
the method further includes, subsequently to the step of positioning, facilitating protrusion of the anchor from the proximal half.

In an application, the step of percutaneously introducing the implant includes percutaneously introducing the implant while the implant is not disposed within a delivery tube.

There is further provided, in accordance with an application of the present invention, apparatus for facilitating percutaneous delivery of an implant to a target site in a body of a subject, facilitated by at least one needle electrode, the apparatus including:
a delivery tool, having a proximal portion and a distal portion, the distal portion including an implant-storage member, the implant-storage member configured to be percutaneously advanced toward the target site, and shaped to define (a) a space that is configured to house the implant, and (b) an opening through which the implant is advanceable;
a guide shaped to define at least one channel and configured to facilitate percutaneous advancement of the needle electrode, via the channel, to the target site; and
a mount, configured:
to be placed on the skin of the subject in a predetermined position with respect to the channel, and
to be coupled to the delivery tool, the coupling of the mount to the delivery tool guiding the delivery of the implant-storage member to the target site.

In an application, the mount is configured to be placed in the given predetermined position with respect to the guide by a mating edge of the mount mating with a mating edge of the guide.

In an application, the delivery tool is configured to deliver the implant to the target site by, when the implant is disposed in the space, and the implant-storage member is disposed at the target site, withdrawing the implant-storage member proximally with respect to the target site while simultaneously holding the implant stationary with respect to the target site.

In an application, the apparatus further includes the needle electrode and an extracorporeal control unit, the extracorporeal control unit being configured to drive the needle electrode to apply a current to the tissue of the subject, so as to identify the target site.

In an application, the mount includes the guide.

In an application, the guide is configured to be placed on the skin of the subject, and the mount is configured to be placed in the given position with respect to the channel by being placed in a given predetermined position with respect to the guide.

In an application, the apparatus is for use with an ultrasound transceiver, and further includes a receptacle, and the receptacle is dimensioned:
to be coupled to a portion of the ultrasound transceiver, and
to be placed in a given predetermined position with respect to the mount such that while (i) the mount is on the skin of the subject, (ii) the receptacle is disposed in the predetermined position thereof with respect to the mount, and (iii) the receptacle is coupled to portion of the ultrasound transceiver, a field of view of the ultrasound transceiver includes the target site.

In an application, the guide is integrated with the receptacle.

In an application, the apparatus further includes a cuff, shaped to at least partly circumscribe a limb of the subject, and the receptacle is coupled to the cuff such that when the cuff is placed on and at least partly circumscribes the limb, the channel is disposed at a first circumferential position of the limb, and the receptacle is disposed at a second circumferential position of the limb that is different to the first circumferential position of the limb.

In an application, the receptacle is coupled to the cuff at a first circumferential position of the cuff, and the guide is coupled to a second circumferential position of the cuff that is different from the first circumferential position of the cuff.

In an application, the receptacle is coupled to the cuff such that the second circumferential position of the limb is 60-120 degrees from the first circumferential position of the limb.

In an application, the guide has a skin-contacting surface, placeable on the skin of the subject, and the channel is articulatable with respect to the skin-contacting surface.

In an application, the channel has a longitudinal axis, the skin-contacting surface defines a plane, and the channel is articulatable such that an angle between the longitudinal axis of the channel and the plane is adjustable.

In an application, the receptacle is couplable to the ultrasound transceiver in more than one orientation of the ultrasound transceiver with respect to the receptacle.

In an application, the receptacle is configured to facilitate rotation of the ultrasound transceiver while remaining coupled to the ultrasound transceiver.

In an application, the apparatus further includes the ultrasound transceiver, and:
the guide has a skin-contacting surface, placeable on the skin of the subject,
the channel is articulatable with respect to the skin-contacting surface, the articulation of the channel defining a channel plane,
the ultrasound transceiver is configured to perform ultrasound detection on an ultrasound plane, and
the receptacle is couplable to the ultrasound transceiver such that the ultrasound plane is coincident with the channel plane.

In an application, the apparatus further includes the ultrasound transceiver, and:
the guide has a skin-contacting surface, placeable on the skin of the subject,
the channel is articulatable with respect to the skin-contacting surface, the articulation of the channel defining a channel plane,
the ultrasound transceiver is configured to perform ultrasound detection on an ultrasound plane, and
the receptacle is couplable to the ultrasound transceiver such that the ultrasound plane intersects the channel plane.

In an application:
the guide has a first skin-contacting surface, and is shaped such that the channel is generally orthogonal to a plane defined by the skin-contacting surface, and
the mount has a second skin-contacting surface, and is shaped to define a lumen through which the implant-storage member is slidable, the lumen being disposed at less than 30 degrees with respect to the second skin-contacting surface.

In an application, the mount is configured to be coupled to the guide in the predetermined position with respect to the guide.

In an application, the mount is shaped to define a receptacle within which at least a portion of the guide is placeable.

In an application, the apparatus further includes a depth indicator, configured to indicate a depth of the needle electrode in the body of the subject.

In an application, the apparatus further includes the needle electrode.

In an application, the depth indicator includes a gauge, configured to be placed on the skin of the subject in a vicinity of the needle electrode.

In an application, the needle electrode includes markings, the depth indicator including the markings.

There is further provided, in accordance with an application of the present invention, apparatus for use with a subject, the apparatus including:
an implant configured to be percutaneously delivered to a site of tissue of the subject; and
a tether:
having a distal end coupled to the implant, and configured to remain coupled to the implant during and after percutaneous delivery of the implant,
having a proximal end, configured to remain outside the subject during and after the percutaneous delivery of the implant,
having a distal portion that includes the distal end, and is configured to promote tissue growth that adheres the distal portion to the tissue, thereby inhibiting movement of the implant with respect to the tissue, and
having a connecting portion that couples the proximal end to the distal portion, and is configured to be disposed within the subject after the percutaneous delivery of the implant, the connecting portion:
having a first state in which the connecting portion is capable of transferring sufficient tension from the proximal end to the distal portion to pull the implant out of the subject, and
being configured to weaken in response to being disposed within the subject, such that, after a duration of being disposed within the subject, tension applied to the proximal end of the tether decouples the proximal end from the distal portion of the tether, the duration being at least 1 day.

In an application, the connecting portion is configured to weaken by becoming absorbed by the tissue of the subject.

In an application, the distal portion has a coating that is configured to inhibit the promotion of tissue growth for a period of the coating being disposed within the subject, and to decrease inhibiting the promotion of tissue growth after the period, the period being at least 1 day.

In an application, the coating and the connecting portion are configured such that the duration is longer than the period.

In an application, the apparatus further includes a delivery tool that includes a tube via which the implant is percutaneously deliverable while the distal end of the tether is coupled to the implant.

In an application, at least the distal and connecting portions of the tether are slidable through at least a distal portion of the tube, such that subsequent to delivery of the implant to the site, withdrawal of the distal portion of the tube from the subject includes sliding of the distal portion of the tube proximally over the distal and connecting portions of the tether.

There is further provided, in accordance with an application of the present invention, a method for use with a subject, the method including:

providing an implant and a tether, a distal end of the tether being coupled to the implant;

percutaneously introducing an implant into tissue of the subject, such that a proximal end of the tether is disposed outside of the subject, while the distal end of the tether remains coupled to the implant;

after a duration of at least 12 hours after the step of introducing, decoupling the proximal end of the tether from the subject by pulling on the proximal end of the tether.

In an application, decoupling the proximal end of the tether from the subject includes decoupling the proximal end of the tether from the subject while leaving the distal end of the tether coupled to the implant.

In an application, a connecting portion of the tether, disposed between the distal end and the proximal end, is configured to become weaker during the duration, and the step of decoupling includes decoupling the proximal end of the tether from the distal end of the tether by pulling on the proximal end of the tether.

In an application, providing the tether includes providing a tether that is capable, immediately after the step of percutaneously introducing the implant, of transferring sufficient tension from the proximal end to the distal portion to pull the implant out of the subject.

There is further provided, in accordance with an application of the present invention, a method for use with a subject, the method including:

forming a percutaneous tunnel into tissue of the subject by advancing a hole-making tool into the tissue;

subsequently, removing the hole-making tool from the tissue;

providing an implant having a rod-shaped housing; and subsequently, advancing an implant having a rod-shaped housing through at least part of the tunnel while the housing is disposed outside of any delivery tube.

In an application:

the implant has a proximal end and a distal end, includes at least one anchor, and has a delivery state in which the anchor protrudes proximally from the proximal end of the implant, the step of advancing the implant includes advancing the implant distal-end first, by pushing the implant using a delivery tool, and the method further includes, subsequently to the step of advancing, anchoring the anchor to the tissue using the delivery tool.

In an application:

pushing the implant using the delivery tool includes pushing the implant using a delivery tool while the anchor is disposed within the delivery tool, and anchoring the anchor to the tissue includes anchoring the anchor to the tissue by releasing the anchor from the delivery tool.

In an application:

pushing the implant using the delivery tool includes pushing the implant using a first implant-engaging portion, and anchoring the anchor to the tissue includes anchoring the anchor to the tissue by changing a shape of the anchor by applying a force to the anchor using the second implant-engaging portion, while providing a reference force to the housing using the first implant-engaging portion.

In an application, applying the force to the anchor includes applying a distally-directed force to the anchor, and applying the reference force to the housing includes applying a proximally-directed force to the housing.

The present invention will be more fully understood from the following detailed description of applications thereof, taken together with the drawings, in which:

BRIEF DESCRIPTION OF THE DRAWINGS

FIGS. 1A-H, which are schematic illustrations of a system for facilitating percutaneous delivery of an implant to a target site in the body of a subject, in accordance with some applications of the invention;

FIGS. 2A-E and 3 are schematic illustrations of a system for facilitating percutaneous delivery of an implant to a target site in the body of a subject, in accordance with some applications of the invention;

FIGS. 4A-G and 5 are schematic illustrations of a system for facilitating percutaneous delivery of an implant to a target site, in accordance with some applications of the invention;

FIGS. 6A-B are schematic illustrations of ultrasound-facilitated techniques, in accordance with some applications of the invention;

FIGS. 7-9 are schematic illustrations of systems for facilitating percutaneous delivery of an implant to a target site in the body of a subject, in accordance with some applications of the invention;

FIGS. 10A-F are schematic illustrations of a system, and techniques for use therewith, for implanting an implant in tissue of a subject, in accordance with some applications of the invention;

FIG. 13 is a schematic illustration of a mount, which comprises a plurality of cradles and/or a plurality of lumens, in accordance with some applications of the invention;

FIGS. 14A-B are schematic illustrations of an electrode-guide system, comprising a guide assembly and an electrode assembly, in accordance with some applications of the invention; and FIGS. 15A-C, 16A-B, and 17A-D are schematic illustrations of techniques for percutaneously implanting an implant in tissue of a subject, in accordance with some applications of the invention.

DETAILED DESCRIPTION OF EMBODIMENTS

Figure 1A:
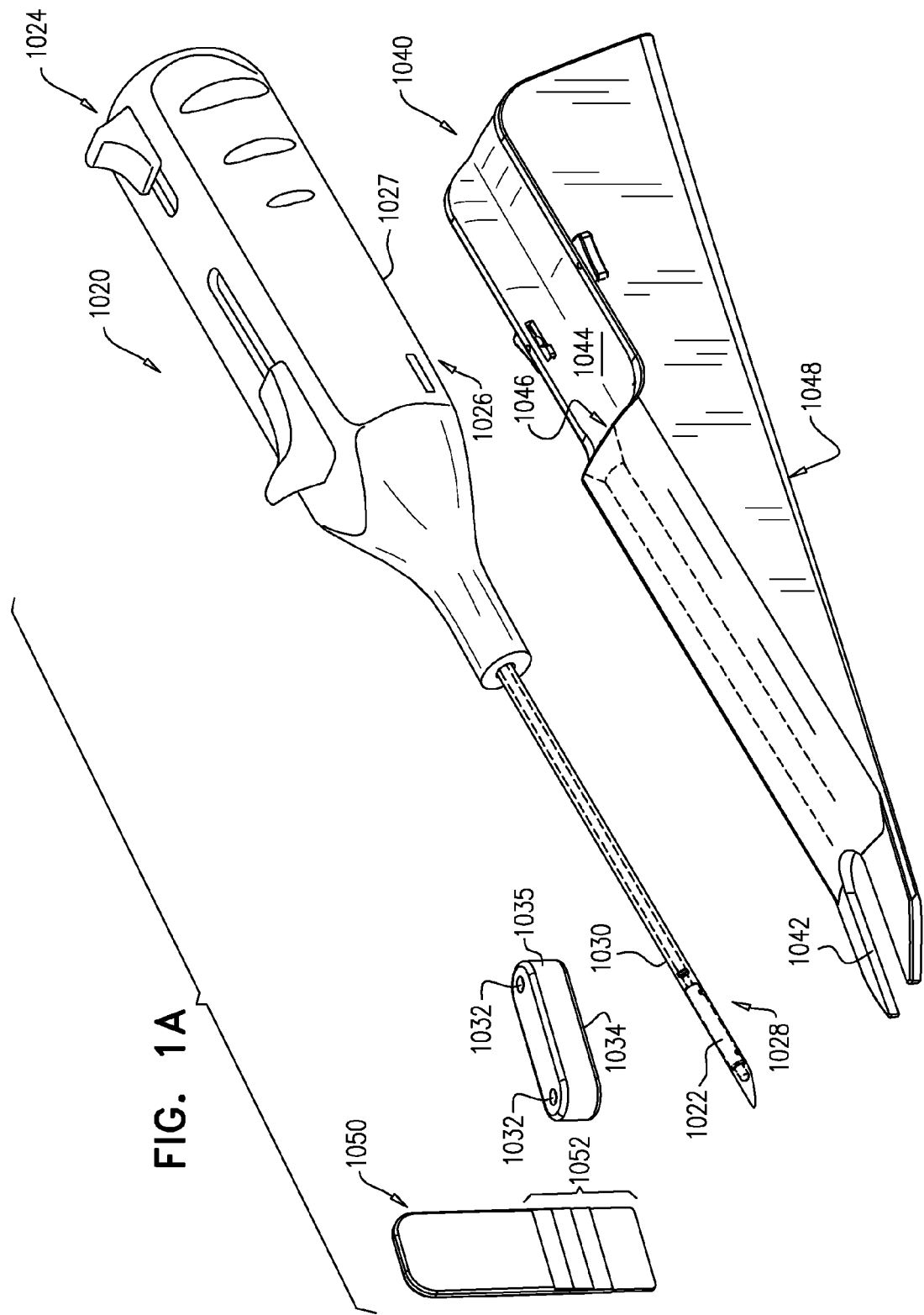

Reference is made to FIGS. 1A-H, which are schematic illustrations of a system 1020, for facilitating percutaneous delivery of an implant 1022 to a target site in the body of a subject, in accordance with some applications of the invention. FIG. 1A shows the components of system 1020.

System 1020 comprises a delivery tool 1024, having a proximal portion 1026 and a distal portion 1028, the distal portion comprising an implant-storage member 1030, configured to be percutaneously advanced toward the target site, and shaped to define a space that is configured to house the implant, and an opening through which the implant is advanceable. Typically, proximal portion 1026 comprises a handle 1027.

For some applications, implant 1022 and/or implant-storage member 1030 comprises an identically-named element described in PCT Application IB2013/060607 to Gross et al., filed Dec. 3, 2013, entitled "Delivery of Implantable Neurostimulators," and which published as WO 2014/087337, which is incorporated herein by reference.

Typically, implant 1022 comprises at least one electrode (e.g., two electrodes; e.g., as shown for implants 1182, 1202, 1362, and/or 1372), and is configured to apply a current (e.g., a treatment current) to the subject (e.g., to tissue in which the implant is implanted, and/or to a nerve within that tissue).

System 1020 further comprises a guide 1034, shaped to define one or more channels 1032 that are configured to facilitate advancement of one or more respective needle electrodes (i.e., percutaneous electrodes), via a respective channel, through the skin of the subject, and to the target site. It is to be noted that throughout the present application, including the specification and the claims, the term "needle electrode" refers to an electrode that is configured to be placed through the skin of the subject (i.e., transcutaneously) while being coupled to extracorporeal apparatus, e.g., as shown in FIG. 1B, and that is typically placed temporarily. The term "needle electrode" is used so as to distinguish such an electrode from other electrodes described in the present application, such as an electrode that is a component of a percutaneously-implanted implant.

System 1020 further comprises a mount 1040, configured to be placed on the skin of the subject in a predetermined position with respect to channels 1032, and to be coupled to the delivery tool so as to facilitate delivery of the implant-storage member (and thereby the implant) to the target site (e.g., the site to which the needle electrodes are advanced via channels 1032). Typically, mount 1040 is configured to be placed in a predetermined position with respect to guide 1034 (e.g., to be coupled to guide 1034 in the predetermined position) by the mount and guide defining respective mating edges that are shaped to mate with each other. For example, and as shown in FIGS. 1A-H, mount 1040 may be shaped to define a receptacle 1042 within which at least a portion of guide 1034 is placeable, typically with a snug fit. For some applications, mount 1040 comprises and/or is integral with guide 1034, and/or itself defines channels 1032.

Mount 1040 is further configured to be coupled to delivery tool 1024, such that the delivery tool (e.g., implant-storage member 1030 thereof) is placed in a given position with respect to channels 1032. For example, mount 1040 may be shaped to define a cradle 1044, configured to receive handle 1027 of delivery tool 1024, and/or a lumen 1046, configured to receive distal portion 1028 of the delivery tool. Cradle 1044 and lumen 1046 are disposed at a given angular disposition alpha_1 with respect to a skin-facing side (e.g., a skin-contacting surface 1048) of mount 1040. Typically, angle alpha_1 is less than 30 degrees and/or greater than 10 degrees (e.g., between 10 and 30 degrees).

System 1020 typically further comprises a depth indicator 1050, such as a gauge 1052 (e.g., a plurality of graduated markings), configured to indicate a depth of insertion of the needle electrodes, as described in more detail hereinbelow.

FIGS. 1B-H show system 1020 being used to facilitate implantation of implant 1022, in accordance with some applications of the invention. It is to be noted that system 1020 is shown being used to facilitate implantation of implant 1022 in a leg of the subject in a vicinity of a tibial nerve 1014 of the subject, by way of illustration, and not by way of limitation. Guide 1034 (e.g., a skin-contacting surface thereof) is placed on the skin of the subject, and needle electrodes 1060 are advanced, through channels 1032 of guide 1034, through the skin of the subject, and into a tissue of the subject (FIG. 1B). Electrodes 1060 are driven (e.g., by an extracorporeal control unit 1062) to apply (e.g., to the tissue of the subject) a current that is similar (e.g., identical) to a current that implant 1022 is configured to apply. Guide 1034 and electrodes 1060 may be repositioned multiple times until a target site is identified, such as a site at which the current has a maximal effect on a detected physiological parameter of the subject.

In addition to repositioning of guide 1034 at different sites on the skin of the subject, electrodes 1060 may be repositioned at different depths within the tissue of the subject. For some applications, the depth of the target site (e.g., the depth at which the electrodes provide maximal effect) is measured using depth indicator 1050. For example, gauge 1052 may be placed next to electrodes 1060, and the depth measured by observing the position of a part of the electrodes (e.g., a proximal end of the electrodes) with respect to graduated markings on the gauge (FIG. 1C). Alternatively or additionally, electrodes 1060 may comprise gradated markings to indicate a depth of the electrodes within the tissue.

Subsequently, mount 1040 is placed on the skin of the subject, in the given position with respect to guide 1034, e.g., by placing at least a portion of guide 1034 within receptacle 1042 (FIG. 1D). For some applications, system 1020 comprises a plurality of mounts 1040, each mount being configured to hold delivery tool 1024 at a different angular disposition with respect to the skin of the subject, such as by each respective cradle 1044 and/or lumen 1046 having a different angular disposition with respect to skin-contacting surface 1048 of the mount. Alternatively, mount 1040 (e.g., cradle 1044 and/or lumen 1046 thereof) may be adjustable so as to change angle alpha_1, and/or may define a plurality of lumens 1046, each with a respective angle alpha_1. An operating physician selects one of the plurality of mounts, selects one of the plurality of lumens, or adjusts the adjustable mount, according to the determined depth of the target site. For some applications, gauge 1052 is color-coded, and each of the plurality of mounts 1040 (or the plurality of lumens 1046) is colored respectively, to facilitate correct selection by the operating physician.

Mount 1040 is secured to the skin (e.g., using adhesive tape 1058), and delivery tool 1024 is coupled to the mount, such as by (1) sliding the distal portion of the delivery tool, comprising implant-storage member 1030, through the lumen of the mount and into the tissue of the subject, and (2) coupling handle 1027 of the delivery tool to the cradle of the mount (FIG. 1E). Positioning of member 1030 (and thereby implant 1022) at the target site is thereby facilitated by (i) the positioning of mount 1040 with respect to guide 1034, and (ii) the coupling of the delivery tool to the mount (and, optionally, the selection of the mount, the selection of the lumen of the mount, and/or the adjustment of the mount).

Implant 1022 is subsequently deployed by withdrawing implant-storage member 1030 proximally while the implant is held still with respect to the tissue, thereby leaving the implant exposed at the target site (FIG. 1F). For some applications, tool 1024 comprises a delivery manipulator 1064, which holds implant 1022 in place in this manner. For such applications, the delivery manipulator is subsequently decoupled from implant 1022 (FIG. 1G). System 1020 is subsequently removed from the subject, leaving implant 1022 at the target site (FIG. 1H).

Although two needle electrodes 1060 are shown, for some applications only one needle electrode is used, e.g., with a return electrode placed on the skin. Similarly, for other systems described herein that show one needle electrode being used, for some applications two needle electrodes are used instead. It is hypothesized that for some applications the use of two needle electrodes advantageously represents the two electrodes of the implant, thereby providing more accurate guidance for the subsequent positioning of the implant.

Reference is now made to FIGS. 2A-E and 3, which are schematic illustrations of a system 1120, for facilitating percutaneous delivery of implant 1022 to a target site 1015 in the body of a subject, in accordance with some applications of the invention. System 1120 is typically identical to system 1020 described hereinabove, mutatis mutandis, except where noted. Compared to system 1020, system 1120 further comprises a receptacle 1124 that is dimensioned to be coupled to a portion of an ultrasound transceiver 1126 (e.g., a commercially-available ultrasound transceiver, or a purpose-made ultrasound transceiver), such as by receiving the portion of the ultrasound transceiver. Receptacle 1124 is integrated with and/or defined by a guide 1134, which replaces guide 1034 of system 1020. Receptacle 1124 is configured (e.g., dimensioned) such that while (i) mount 1040 is on the skin of the subject, (ii) the receptacle is disposed in a predetermined position with respect to the mount (e.g., by guide 1134 being disposed in a predetermined position with respect to the mount), and (iii) the receptacle is coupled to portion of the ultrasound transceiver, a field of view of the ultrasound transceiver includes the target site.

Figure 3:
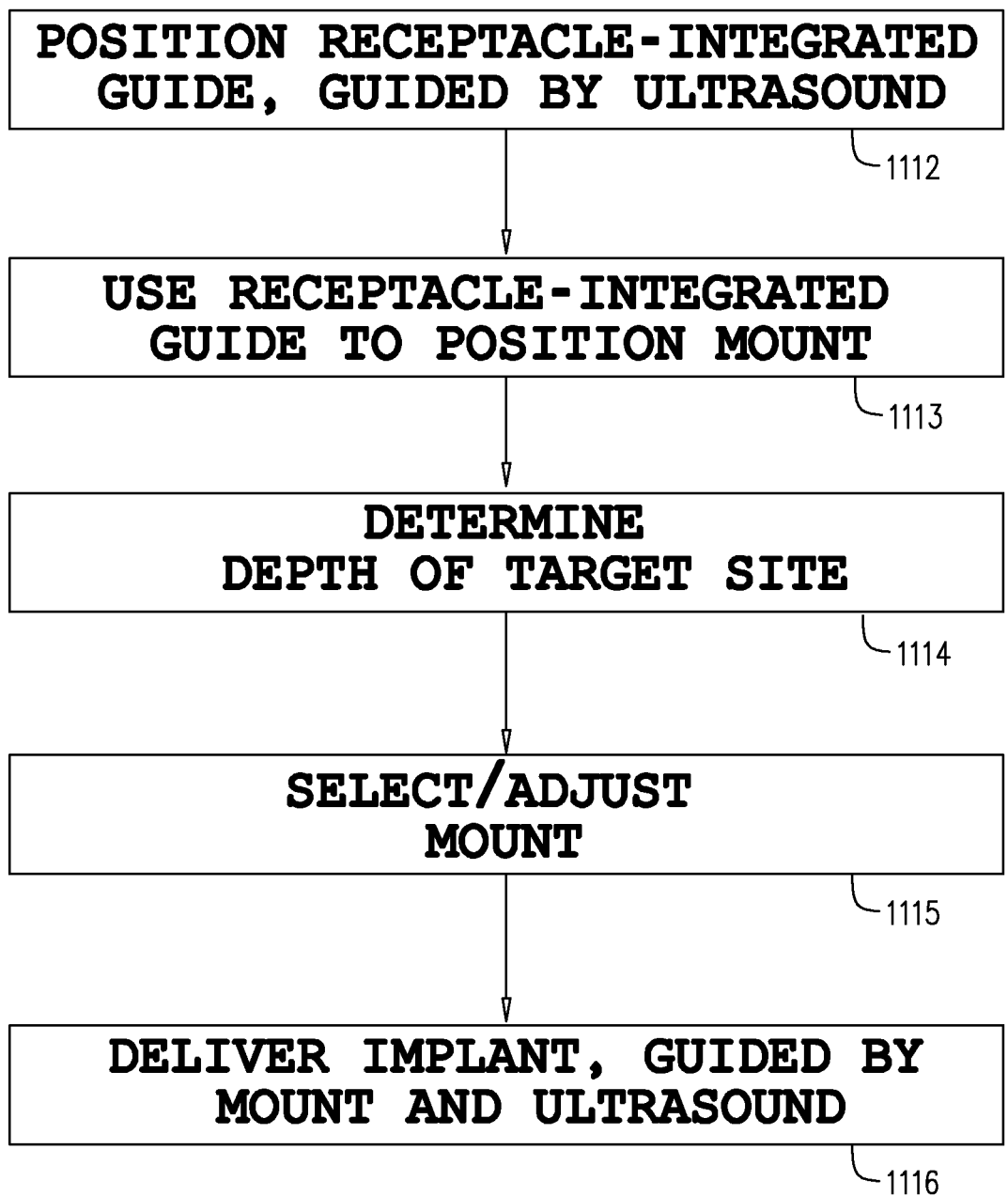
Figure 4C:
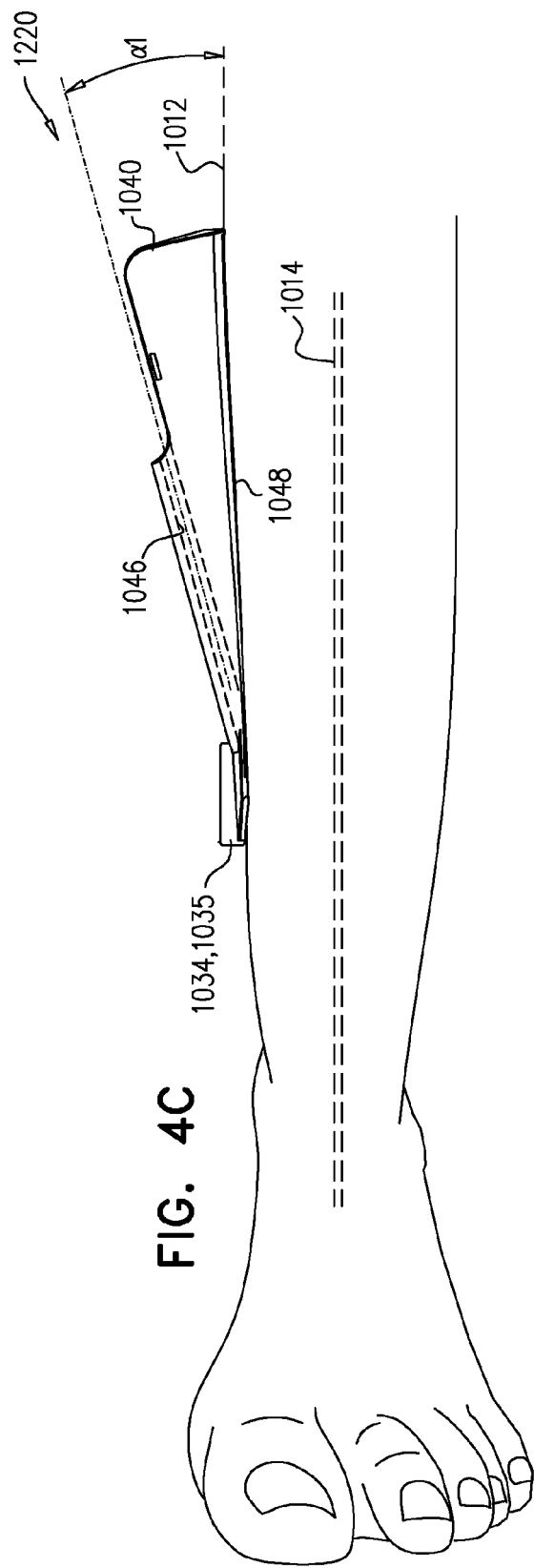
Figure 4D:
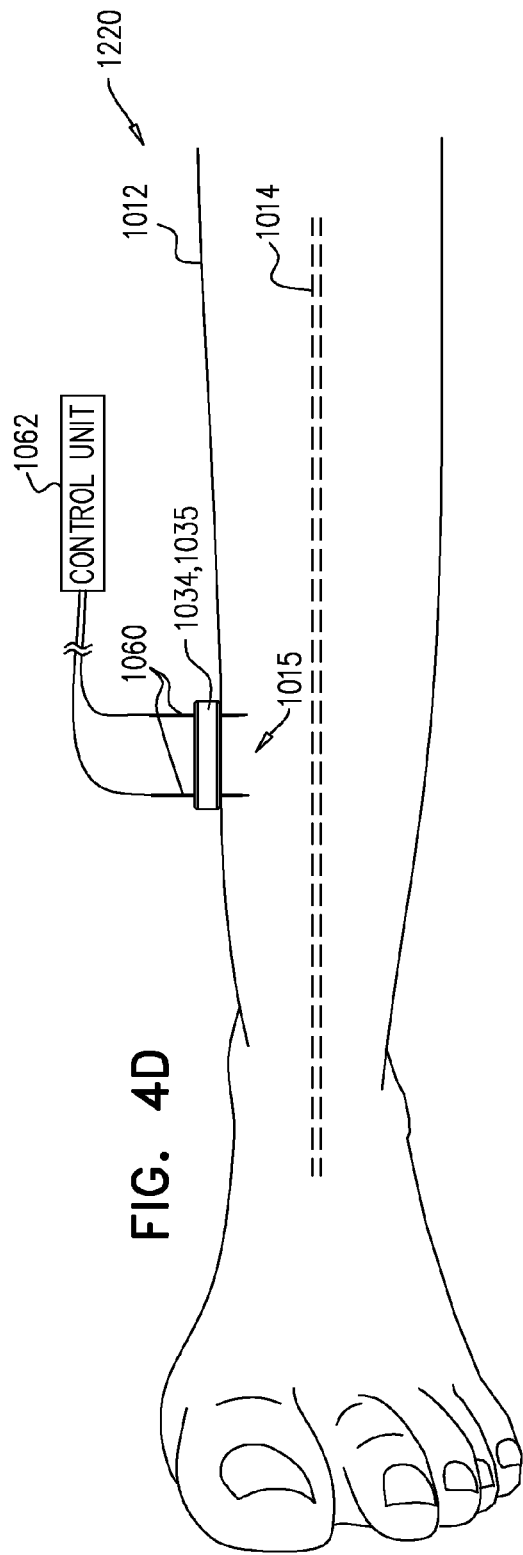

FIGS. 2A-E show system 1120 being used to facilitate implantation of implant 1022, and FIG. 3 is a flow chart showing at least some steps of this use. It is to be noted that system 1120 is shown being used to facilitate implantation of implant 1022 in the leg in a vicinity of tibial nerve 1014, by way of illustration, and not by way of limitation.

FIG. 2A shows guide 1134 having been placed on the skin of the subject, in a similar way to guide 1034 of system 1020 (step 1112 of FIG. 3). However, placement of guide 1134 is facilitated by ultrasound imaging, using ultrasound transceiver 1126, e.g., as described in more detail hereinbelow, such as with reference to FIGS. 6A-9. For example, the ultrasound imaging may facilitate placement of guide 1134 (e.g., channels 1032 defined by the guide) directly over nerve 1014, and/or alignment of an axis of guide 1134 (e.g., a longitudinal axis of the guide and/or an axis between channels 1032) with nerve 1014. FIG. 2B shows electrodes 1060 having been advanced through channels 1032 into tissue, and being driven to apply current to the tissue, e.g., as described hereinabove with reference to FIG. 1B (step 1113 of FIG. 3).

The steps shown in FIGS. 2C-D, for (i) measuring the depth of the target site (step 1114 of FIG. 3), and (ii) selecting/adjusting mount 1040 (step 1115 of FIG. 3), are typically identical to those described with reference to FIGS. 1C-D. As shown in FIG. 2E, delivery tool 1024 is coupled to mount 1040 (e.g., as described hereinabove) so as to deliver implant 1022 to the target site (step 1116 of FIG. 3). In addition to the facilitation of implant delivery provided by features of system 1120 that are identical to those of system 1020, system 1120 provides further facilitation of implant delivery using ultrasound imaging. As shown in FIG. 2E, ultrasound transceiver 1126, coupled to receptacle 1124, typically facilitates implant delivery, e.g., as described in more detail hereinbelow. As shown, transceiver 1126 may be removed during the steps shown in FIGS. 2B-D. Alternatively, transceiver 1126 may remain coupled to receptacle throughout the procedure.

Reference is now made to FIGS. 4A-G and 5, which are schematic illustrations of a system 1220, for facilitating percutaneous delivery of implant 1022 to target site 1015, in accordance with some applications of the invention. System 1220 is typically identical to system 1120 described hereinabove, mutatis mutandis, except where noted. Whereas system 1120 comprises receptacle 1124 that is integrated with and/or defined by the guide 1134, system 1220 comprises guide 1034 (described with reference to system 1020 of FIGS. 1A-H) and a receptacle 1224 that is distinct from the guide.

Using system 1220 (FIGS. 4A-5) to deliver implant 1022 typically involves more steps than using system 1120 (FIGS. 2A-3). However, it is hypothesized that system 1220 advantageously facilitates the use of electrodes 1060 to identify target site 1015 in the absence of a receptacle for an ultrasound receiver, thereby increasing ease of handling.

FIG. 4A shows a transducer-receiving unit 1234, comprising receptacle 1224, having been placed on the skin of the subject, in a similar way to that described hereinabove for guide 1034 and guide 1134 (step 1241 of FIG. 5). Unlike guide 1134, transducer-receiving unit 1234 typically does not define channels for electrodes 1060. Ultrasound transceiver 1126 is used to facilitate placement of unit 1234, as described for guide 1134, mutatis mutandis. Subsequently, mount 1040 is placed on the skin in a predetermined position with respect to unit 1234, e.g., by the mount and unit 1234 defining respective mating edges that are shaped to mate with each other (FIG. 4B) (step 1242 of FIG. 5). For example, and as described with respect to guide 1034 and guide 1134, a receptacle 1042 defined by mount 1040 may be shaped to receive (e.g., snugly) a portion of unit 1234. Subsequently, unit 1234 is replaced with guide 1034 while retaining mount 1040 in place, thereby positioning the guide in a predetermined position with respect to the mount (step 1243 of FIG. 5), as well as in a predetermined position with respect to the previous position of unit 1234.

Guide 1034 is then used to guide electrodes 1060 for identification of target site 1015 (e.g., the depth thereof), as described hereinabove (FIGS. 4D-E) (step 1244 of FIG. 5). Typically, and as shown, mount 1040 is removed from the skin during these steps, and then replaced (FIG. 4F). Moreover, it is typically at this stage that mount 1040 is selected and/or adjusted (as described hereinabove) (step 1245 of FIG. 5). After target site 1015 has been identified, guide 1034 is replaced with unit 1234, guided by mount 1040 (step 1246 of FIG. 5), and the mount is subsequently used to facilitate implantation of implant 1022, typically guided by ultrasound, as described hereinabove (FIG. 4G) (step 1247 of FIG. 5).

Reference is made to FIGS. 6A-B, which are schematic illustrations of ultrasound-facilitated techniques, in accordance with some applications of the invention. As described hereinabove, ultrasound may be used to facilitate the techniques described with reference to FIGS. 2A-5. Ultrasound transceiver 1126 is in communication with a control unit 1151, which comprises a processor 1153 and a display 1152. Control unit 1151 is configured to receive an ultrasound signal from transceiver 1126, and to display on display 1152 an output that is indicative of the signal. Transceiver 1126 and control unit 1151 together define an ultrasound system 1150.

FIG. 6A shows ultrasound being used to facilitate placement of guide 1134, e.g., described with reference to FIG. 2A and step 1112 of FIG. 3. Typically, control unit 1151 displays one or more display guides 1154 on display 1152, which schematically indicate an alignment of guide 1134.

For some applications one or more guides 1156, which schematically indicate a position of channels 1032 defined by guide 1134. The coupling of transceiver 1126 to receptacle 1124 fixes a juxtaposition between the transceiver and guide 1134, and thereby facilitates the display of the alignment of the guide (and the position of the channels), e.g., without these elements being actually detected by system 1150. System 1150 detects nerve 1014, which is also displayed on display 1152 (labeled 1014').

For some applications, control unit 1151 (e.g., processor 1153) is configured to display a standard ultrasound image on display 1152, and to appropriately juxtapose (e.g., overlay) guides 1154 and/or 1156 with respect to the ultrasound image. For some applications, processor 1153 is configured to recognize a component of the ultrasound signal that is indicative of nerve 1014, and to schematically display the nerve on display 1152. For example, nerve 1014 may be "cartoonified", e.g., by displaying the nerve in a particular color, and/or by reducing the complexity of the displayed nerve compared to information received in the signal from transceiver 1126. For example, and as shown, nerve 1014 may be displayed as a simple line (which may or may not be straight, depending on the anatomy of the subject). Alternatively or additionally, a visual indicator, such as an alphanumeric indicator, may be used to label the nerve and/or to indicate the position and/or alignment. Alternatively or additionally, an audible signal may be used.

Frame 1 of FIG. 6A shows nerve 1014 being schematically displayed on display 1152, while not translationally or rotationally aligned with guides 1154 or 1156. Frame 2 shows nerve 1014 having become rotationally aligned with the guides (e.g., due to rotation of guide 1034 on the skin), but not yet translationally aligned with the guides. Frame 3 shows nerve 1014 having become also translationally aligned with the guides, e.g., after translationally sliding guide 1134 over the skin.

FIG. 6B shows ultrasound being used to facilitate advancement of delivery of implant-storage member 1030 of delivery tool 1024 and implant 1022, e.g., described with reference to FIG. 2E and step 1116 of FIG. 3. For some applications control unit 1151 is switched into a different mode (e.g., displaying different guides, and/or showing/hiding nerve 1014) in order to facilitate this delivery. During facilitation of delivery, control unit 1151 displays one or more guides 1164 on display 1152, which schematically indicate target site 1015.

Frame 1 of FIG. 6B shows the distal end of tool 1024 (displayed as 1024') entering target site 1015. Frame 2 shows the distal end of the tool reaching a distal end of the target site; in this position implant-storage member 1030, and implant 1022 therewithin, are disposed at the target site. Frame 3 shows implant 1022 (displayed as 1022') implanted at the target site; tool 1024 having been withdrawn.

Similarly to as described with reference to FIG. 6A, for some applications, control unit 1151 (e.g., processor 1153) is configured to display a standard ultrasound image on display 1152, and to appropriately juxtapose (e.g., overlay) guides 1164 with respect to the ultrasound image. For some applications, processor 1153 is configured to recognize a component of the ultrasound signal that is indicative of tool 1024, and to schematically display the tool on display 1152. For example, tool 1024 may be "cartoonified", e.g., by displaying the tool in a particular color, and/or by reducing the complexity of the displayed nerve compared to information received in the signal from transceiver 1126. For example, and as shown, tool 1024 may be displayed as a simple line. Implant 1022 may also be displayed in this manner.

Although receptacle 1124 is shown as being on the opposite site of the target site to mount 1040, it is to be noted that the scope of the invention includes other positions of receptacle 1124, thereby providing other views of the target site. The same is true for other ultrasound-transducer receptacles described herein.

Figure 8:
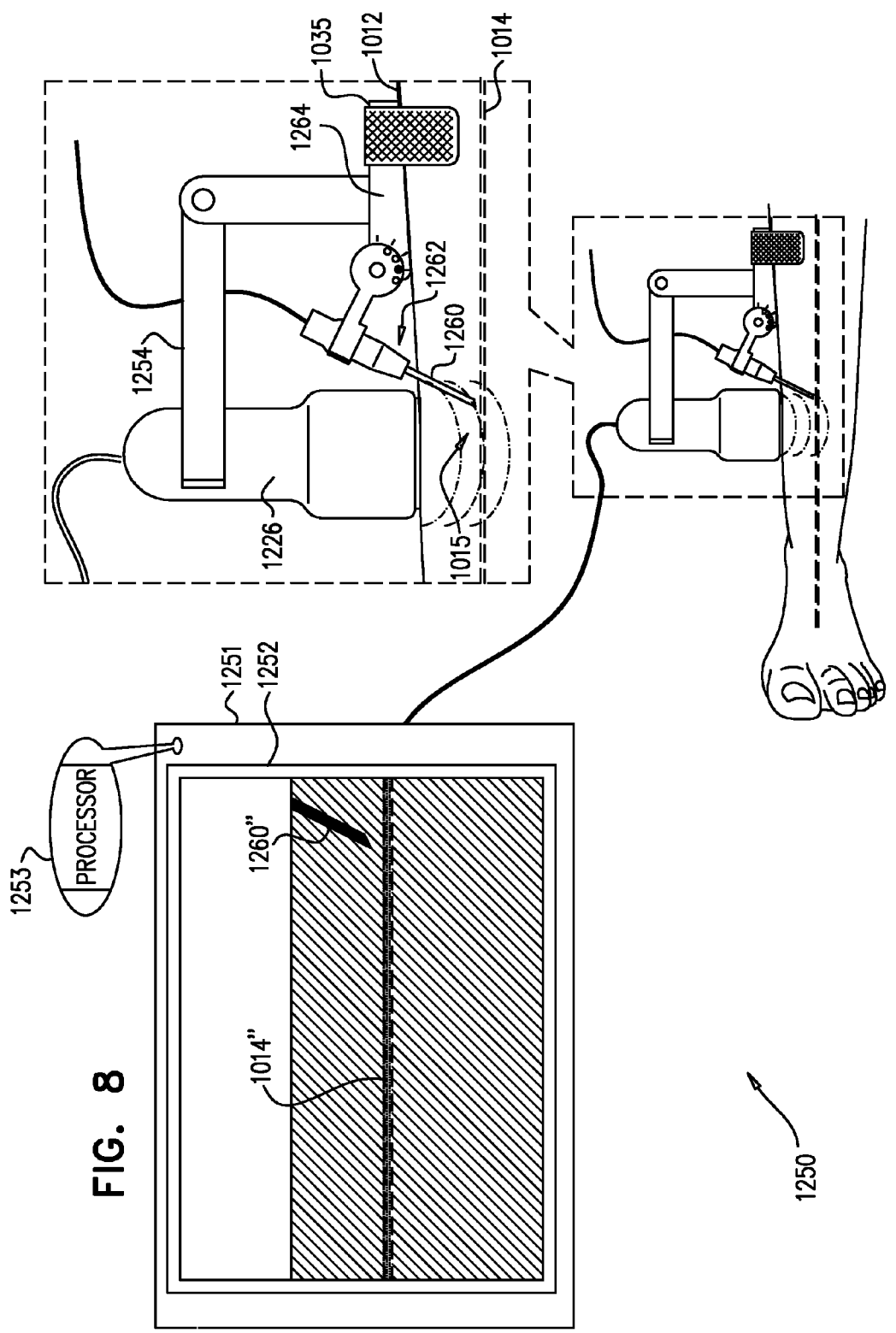

Reference is made to FIGS. 7-9, which are schematic illustrations of systems for facilitating percutaneous delivery of implant 1022 to a target site in the body of a subject, in accordance with some applications of the invention. For some applications, FIGS. 7-9 show respective independent applications of the invention. For some applications, and as described hereinbelow, FIGS. 7-8 show different states of elements in an application of the invention.

FIGS. 7-8 show a system 1250, comprising a guide 1264, which serves the same function as guide 1134 of system 1120, mutatis mutandis, except where noted. Guide 1264 defines a channel 1262 via which a needle electrode 1260 is advanceable into the subject (e.g., toward the target site). Guide 1264 has a skin-contacting surface, placeable on skin 1012 of the subject, and channel 1262 is articulatable (e.g., at an articulating coupling 1266) with respect to the skin-contacting surface. The skin-contacting surface defines a skin-contacting plane, and channel 1262 is articulatable such that an attack angle between the skin-contacting plane and a longitudinal axis of the channel is adjustable. That is, the articulation of channel 1262 defines a channel plane (i.e., a plane on which the channel is articulatable), and the channel plane intersects the skin-contacting plane. For some applications, and as shown, guide 1264 comprises an indicator 1268, typically at coupling 1266, that indicates the attack angle between the skin-contacting plane and the longitudinal axis of the channel.

The depth of needle electrode 1260 in the tissue of the subject is adjustable by adjusting the attack angle, and/or by adjusting the distance through channel 1262 that the electrode is advanced. Similarly, the selection and/or adjustment of mount 1040 may be performed responsively to the attack angle, the advancement distance of electrode 1260, or a combination of these factors.

System 1250 comprises a receptacle 1254, integrated with and/or coupled to guide 1264, and configured to be coupled to an ultrasound transceiver 1226 (e.g., a commercially-available ultrasound transceiver, or a purpose-made ultrasound transceiver). Typically, ultrasound transceiver 1226 is couplable to receptacle 1254 in more than one orientation of the transceiver with respect to the receptacle. For some applications, receptacle 1254 facilitates rotation of transceiver 1226 while remaining coupled to the transceiver. FIG. 7 shows transceiver 1226 in a first rotational orientation with respect to receptacle 1254, and FIG. 8 shows the transceiver in a second rotational orientation with respect to the receptacle.

For some applications, and as shown, transceiver 1226 is configured to perform ultrasound detection on an ultrasound plane (e.g., the transceiver is a 2D transceiver), e.g., such that a resulting image on display 1252 represents a cross-section through the tissue of the subject. This is represented in FIGS. 7-8 as ultrasound waves being shown as wider in FIG. 8 than in FIG. 7. In the first rotational orientation of transceiver 1226 with respect to receptacle 1254, the ultrasound plane intersects the channel plane (e.g., is generally orthogonal to the channel plane) (FIG. 7). Therefore, in the first rotational orientation, the image displayed on display 1252 typically displays electrode 1260 (as element 1260") in transverse cross-section (e.g., as a dot). In the second rotational orientation of transceiver 1226 with respect to receptacle 1254, the ultrasound plane is coincident with the channel plane (or is parallel and close to the channel plane) (FIG. 8). Therefore, in the second rotational orientation, the image displayed on display 1252 typically displays electrode 1260 (as element 1260") in longitudinal cross-section (e.g., as a line).

Typically, guide 1264 is placed on skin 1012 such that the channel plane is generally aligned with a longitudinal axis of nerve 1014 (e.g., by aligning the channel plane with a distal-proximal axis of the leg). In such an orientation of guide 1264 with respect to nerve 1014, (a) when transceiver 1226 is in the first rotational orientation, the image displayed on display 1252 typically displays nerve 1014 (as element 1014") in transverse cross-section; and (b) when transceiver 1226 is in the second rotational orientation, the image displayed on display 1252 typically displays nerve 1014 (as element 1014") in longitudinal cross-section.

It is hypothesized that the ability to change the viewing angle displayed by display 1252 advantageously facilitates accurate positioning of guide 1264 and electrode 1260 with respect to nerve 1014. For example, it is hypothesized that the transverse cross-sectional view shown in FIG. 7 facilitates identification of, and positioning of the guide with respect to, nerve 1014, whereas the view shown in FIG. 8 facilitates positioning of electrode 1260.

For some applications, the following procedure is followed:

(1) The apparatus is placed generally as shown in FIG. 7, but without electrode 1260 having been advanced into the tissue of the subject.

(2) Responsively to the position of displayed nerve 1014" on display 1252, the apparatus is repositioned. Typically, the purpose of this step is to obtain a particular lateral position of displayed nerve 1014" on display 1252, e.g., such as the displayed nerve being horizontally central, and/or aligned with one or more display guides (e.g., as described hereinabove, mutatis mutandis). This is typically performed by sliding guide 1264 laterally over the skin (e.g., partly around the circumference of the leg).

(3) Subsequently, transceiver 1226 is rotated (e.g., 90 degrees) such that the apparatus appears as shown in FIG. 8. Due to the positioning obtained in step (2), once the transceiver is rotated, nerve 1014 is coincident with the ultrasound plane, and displayed nerve 1014" thereby appears as a line. It is to be noted that the positioning achieved in step (2) facilitates the detection and displaying of nerve 1014 in step (3): Once the positioning in step (2) has been achieved, the subsequent rotation of transceiver 1226 results in nerve 1014 being coincident with the ultrasound plane, rather than being parallel but displaced with respect to the ultrasound plane (and thereby invisible to the transceiver and absent from the image displayed by display 1252).

(4) Needle electrode 1260 is advanced into the tissue of the subject toward nerve 1014, while being observed on display 1252.

(5) Electrode 1260 is used to apply current to nerve 1014, so as to measure the depth of the target site, as described for other systems hereinabove, mutatis mutandis. For system 1250 the depth may be measured based on the attack angle and/or the advancement position of electrode 1260.

(6) A mount 1040 is selected and/or adjusted, according to the measured depth, is placed in the predetermined position with respect to guide 1264 (e.g., by mating respective mating surfaces of the mount and the guide), and implant 1022 is implanted using tool 1024, guided by mount 1040, as described hereinabove, mutatis mutandis.

FIG. 9 shows a system 1280 comprising a guide 1294, which serves the same function as guide 1134 of system 1120, mutatis mutandis, except where noted. Guide 1264 defines a channel 1292 via which a needle electrode 1280 is advanceable into the subject (e.g., toward the target site). System 1280 comprises a receptacle 1284, integrated with and/or coupled to guide 1294, and configured to be coupled to ultrasound transceiver 1226.

For some applications, and as shown, transceiver 1226 is configured to perform ultrasound detection on an ultrasound plane (e.g., the transceiver is a 2D transceiver), such that a resulting image on display 1252 represents a cross-section through the tissue of the subject (e.g., as described hereinabove with respect to FIGS. 7-8, mutatis mutandis). Whereas in system 1250 the needle electrode typically contacts skin 1012 at generally the same circumferential position on the leg of the subject as does the ultrasound transceiver, in system 1280, the needle electrode contacts the skin at a differential circumferential position on the leg than does the ultrasound transceiver. For example, and as shown, electrode 1290 may contact the skin at a circumferential position that is 60-90 degrees (e.g., about 90 degrees) offset from the circumferential position at which transceiver 1226 contacts the skin. This arrangement provides a different ultrasound image to that of FIGS. 7 and 8. Rather than displayed nerve 1014" and displayed electrode 1260" being either both in transverse cross-section or both in longitudinal cross-section, in system 1280 the nerve is displayed in transverse cross-section and the electrode is displayed in longitudinal cross-section. For some applications, guide 1294 comprises a cuff 1286 that is shaped to at least partly circumscribe the leg, and receptacle 1284 and channel 1292 are coupled to the cuff at respective different circumferential positions.

As for other systems described herein, the depth of the target site is identified using needle electrode 1290, and selection and/or adjustment of mount 1040 is performed responsively to the identified depth.

As is shown in the figures, guides 1264 and 1294 are typically both more complex than guide 1034 (which isn't integrated with a transducer receptacle) and guide 1134 (which does comprise a transducer receptacle). Nevertheless, each of these guides has a mount-engaging portion 1035 that defines the surface that mates with the respective mating surface mount 1040. Similarly, transducer-receiving unit 1234 also has a mount-engaging portion 1235, which may be shaped similarly to mount-engaging portion 1035 of guide 1034. For some applications, most or all of the guide is the mount-engaging portion (e.g., as shown for guide 1034).

Reference is made to FIGS. 10A-F, which are schematic illustrations of a system 1180, and techniques for use therewith, for implanting an implant 1182 in tissue of a subject, in accordance with some applications of the invention. System 1180 comprises a tether 1184, and typically also comprises a delivery tube 1187 (e.g., a needle).

A distal end 1186 of tether 1184 is coupled to implant 1182, and is configured to remain coupled to the implant during and after percutaneous delivery of the implant. A proximal end 1188 of tether 1184 is configured to remain outside the subject during and after the percutaneous delivery of the implant. A distal portion 1190 of tether 1184 includes distal end 1186, and is configured to promote tissue growth (e.g., fibrosis) so as to cause adherence of tissue to the distal portion of the tether, thereby inhibiting movement of implant 1182 with respect to the tissue. A proximal portion 1185 of tether 1184 includes proximal end 1188.

A connecting portion 1192 of tether 1184 couples proximal portion 1185 (and thereby proximal end 1188) to distal portion 1190, and is configured to be disposed within the subject after the percutaneous delivery of the implant. Connecting portion 1192 has a first state in which it is capable of transferring sufficient tension from the proximal end to the distal portion to pull the implant out of the subject (if the proximal end is pulled sufficiently strongly). Connecting portion 1192 is configured to weaken in response to being disposed within the subject, such that, after a duration of being disposed within the subject, tension applied to the proximal end of the tether decouples proximal portion 1185 (and thereby proximal end 1188) from distal portion 1190. Typically, this duration is greater than 1 day and/or less than 2 months, e.g., between 1 day and 2 months, e.g., between 1 week and 2 months, e.g., as between 2 weeks and 2 months, such as 2-4 weeks.

For some applications, connecting portion 1192 is configured to weaken by becoming absorbed by the tissue of the subject.

For some applications, distal portion 1190 is configured to promote the tissue growth by promoting a sterile inflammatory reaction (e.g., by comprising an inflammatory factor), or by comprising a growth factor. For some applications, distal portion 1190 comprises a fabric that promotes tissue growth, such as a Polyethylene terephthalate (PET) fabric (e.g., Dacron™). For some applications, distal portion 1190 has a coating 1194 that is configured to inhibit the promotion of tissue growth for a period of the coating being disposed within the subject, and to subsequently decrease (e.g., stop) inhibiting the promotion of tissue growth. Typically this period is at least 12 hours and/or less than 2 weeks, e.g., between 12 hours and two weeks, e.g., between 12 hours and 1 week (e.g., between 12 hours and 5 days, such as 1-3 days); between 1 day and 2 weeks (e.g., 1-10 days, e.g., 2-7 days, such as 3-5 days); and/or between 2 days and 2 weeks (e.g., between 3 days and 2 weeks, e.g., 5-12 days, such as 7-10 days. For some applications the duration described hereinabove in which connecting portion 1192 becomes weakened is longer (e.g., at least 1 day longer) than the period in which coating 1194 stops inhibiting the promotion of tissue growth. Thus, until the time at which implant 1182 becomes anchored by distal portion 1190, it is possible to retrieve the implant by pulling on proximal end 1188. For some applications coating 1194 comprises an inhibitor of inflammation.

Figure 10A:
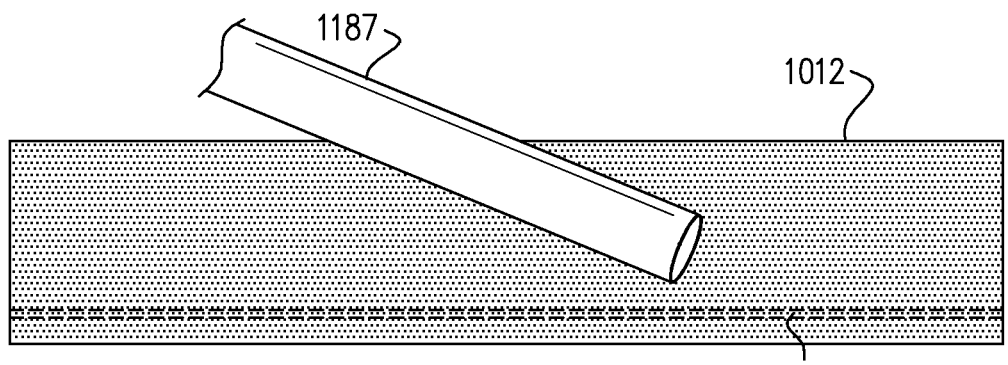
Figure 10B:
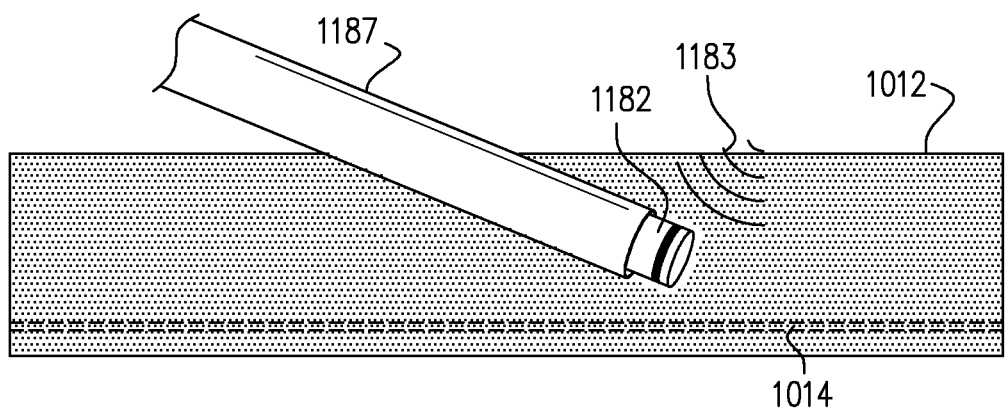

FIG. 10A shows delivery tube 1187 having been percutaneously advanced into tissue of the subject. FIG. 10B shows partial withdrawal of tube 1187, exposing implant 1182 and distal end 1186 of tether 1184. At this stage, for some applications implant 1182 is wirelessly powered to apply its treatment via one or more of its electrodes, e.g., to test its position (shown as wireless power 1183). For some such applications, only one electrode of the implant is exposed at this stage, and another electrode serves as a return electrode. For some such applications, tube 1187 serves as the return electrode. FIG. 10C shows tube 1187 having been completely withdrawn from the subject, such that distal portion 1190 (including distal end 1186) and connecting portion 1192 are disposed within the tissue of the subject, and proximal end 1188 is disposed outside of the subject. It is to be noted that when tube 1187 is withdrawn, at least a distal portion of the tube is slid over progressively proximal portions of tether 1184 (e.g., over distal portion 1190 and then over connecting portion 1192). Typically, proximal end 1188 is secured to skin 1012 of the subject, e.g., using adhesive tape 1058.

Schematically, FIG. 10C shows coating 1194 on distal portion 1190, and 7D does not show the coating. This change in the schematic illustration of distal portion 1190 may represent absorption of coating 1194 by the tissue, exhaustion of a tissue growth-inhibiting drug within the coating, or another way in which the coating may decrease (e.g., stop) its inhibition of tissue growth. FIG. 10D shows a zone 1196 of the resulting tissue growth, facilitated by the characteristic(s) of distal portion 1190 that promote the tissue growth.

FIG. 10E shows subsequent weakening of connecting portion 1192, schematically shown as disappearance of the connecting portion. FIG. 10F shows subsequent removal of proximal portion 1185 from the subject, leaving behind implant 1182 anchored by portion 1190 of tether 1184.

It is to be noted that the techniques described with reference to FIGS. 10A-F may be used in combination with those described elsewhere herein. For example, tether 1184 may be used to facilitate retrieval and/or anchoring of implant 1022 and/or 1202, mutatis mutandis.

Reference is made to FIGS. 11A-C and 12A-C, which are schematic illustrations of an implant 1202, and techniques for implantation thereof, in accordance with some applications of the invention. Implant 1202 is configured to electrically stimulate nerve 1014 of a subject. Implant 1202 comprises a rod-shaped housing 1204, a cathode 1206 on a distal half 1214 of the housing, an anchor 1210 configured to protrude from a proximal half 1216 of the housing, an anode 1208, and circuitry 1212 disposed within the housing. Circuitry 1212 is configured to drive a current between cathode 1206 and anode 1208 while implant 1202 is disposed in tissue of a subject. Implant 1202 does not have an anchor that is configured to protrude from the distal half of housing 1204. The terms "proximal" and "distal" refer to the orientation of implant 1202 for implantation; distal half 1214 enters the body of the subject and/or exits the distal end of a delivery tube before proximal half 1216 does so. Typically, anode 1208 is disposed on the proximal half of housing 1204. Typically, implant 1202 comprises an antenna 1218, configured to receive wirelessly-transmitted power by which circuitry 1212 is powered, and which the circuitry uses to drive between cathode 1206 and anode 1208. Antenna 1218 is typically (but not necessarily) disposed within housing 1204.

Figure 11A:
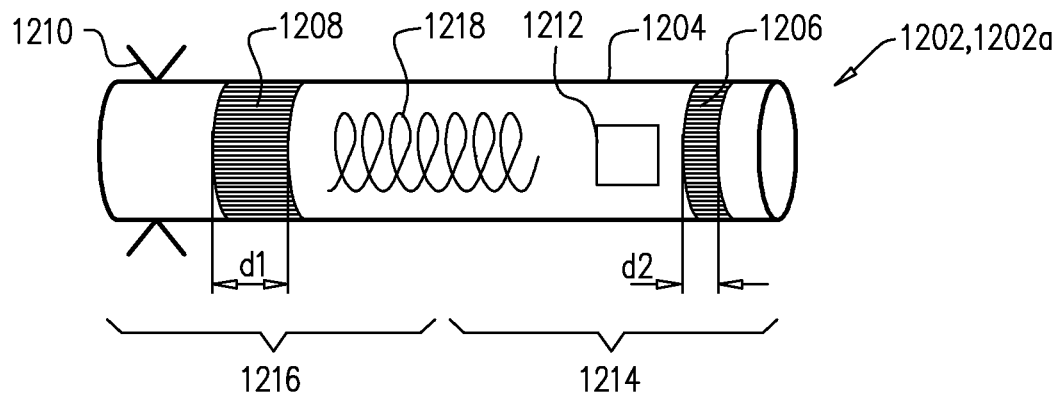
FIGS. 11A-C and 12A-C are schematic illustrations of an implant, and techniques for implantation thereof, in accordance with some applications of the invention.
Figure 11B:
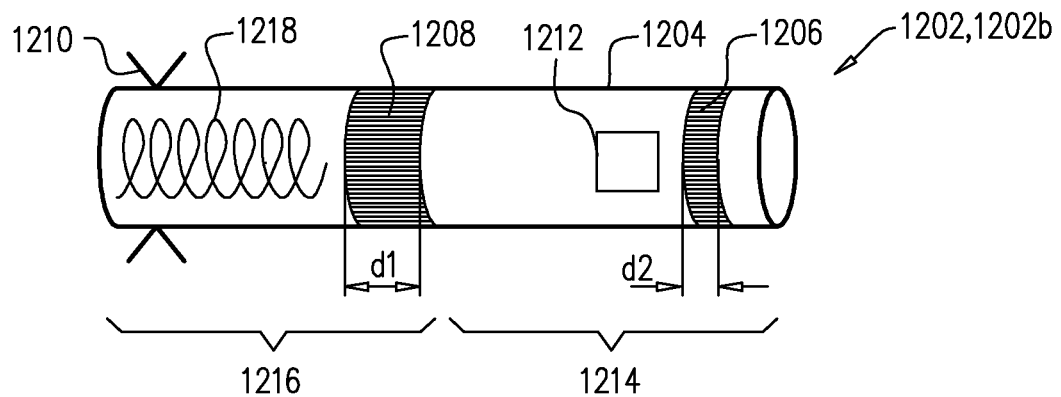
Figure 11C:
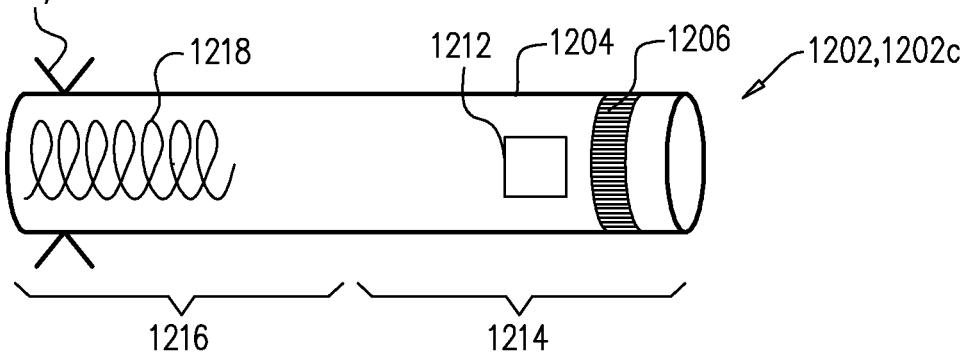

FIGS. 11A-C shows respective embodiments of implant 1202, in accordance with some applications of the invention. FIG. 11A shows an implant embodiment 1202a, FIG. 11B shows an implant embodiment 1202b, and FIG. 11C shows an implant embodiment 1202c.

For some applications, anode 1208 is disposed at a site of housing 1204 that is between cathode 1206 and anchor 1210, e.g., as shown in embodiments 1202a and 1202b of FIGS. 11A and 11B. For some applications, anchor 1210 comprises and/or serves as anode 1208 (e.g., anchor 1210 and anode 1208 are integrated), e.g., as shown in embodiment 1202c of FIG. 11C. For some applications, anode 1208 has a larger surface area than does cathode 1206, e.g., as indicated by dimensions d1 and d2 in FIGS. 11A and 11B. It is hypothesized that, for some applications, the larger surface area of anode 1208 facilitates stimulation of nerve 1014 while anode 1208 is disposed further from nerve 1014 than is cathode 1206, e.g., as described with reference to FIGS. 12A-C. For example, the relatively large surface area of anode 1208 may reduce impedance and/or reduce a likelihood of electrode deterioration due to high current density. It is hypothesized that, for some applications, the relatively small surface area of cathode 1206 increases the likelihood of successfully inducing action potentials in nerve 1014. For some applications, cathode 1206 is roughened so as to increase its effective surface area despite its otherwise smaller size.

Alternatively, anode 1208 may have a smaller surface area than does cathode 1206, e.g., so as to reduce a return flow path for the applied current.

For some applications antenna 1218 is disposed between cathode 1206 and anode 1208 e.g., as shown in embodiment 1202a of FIG. 11A. For some applications antenna 1218 is disposed proximal to the anode (i.e., disposed further from cathode 1206 than is anode 1208), e.g., as shown in embodiment 1202b of FIG. 11B.

Figure 12A:
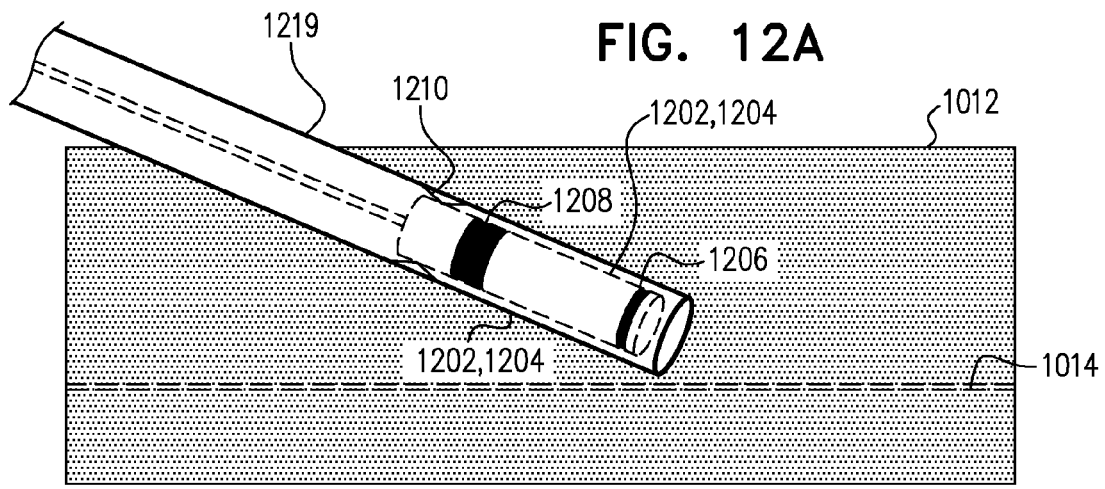
Figure 12B:
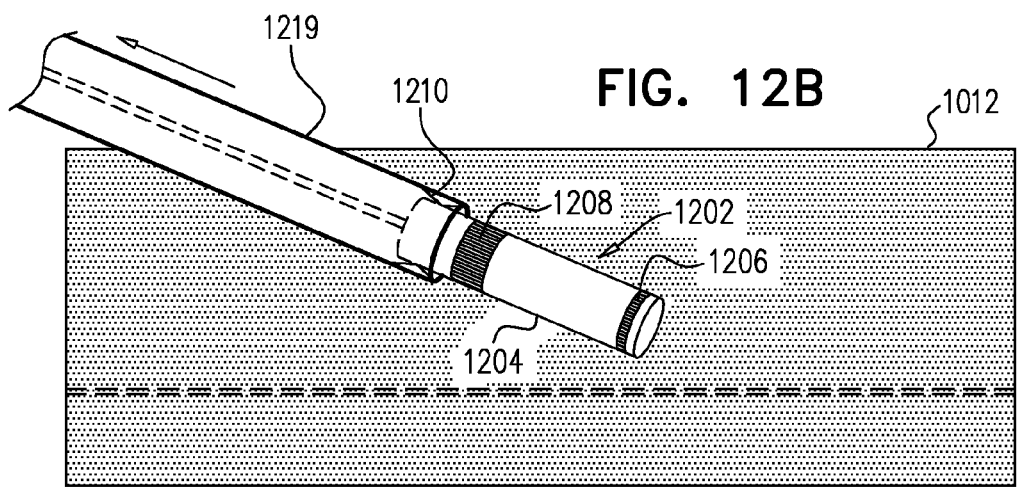
Figure 12C:
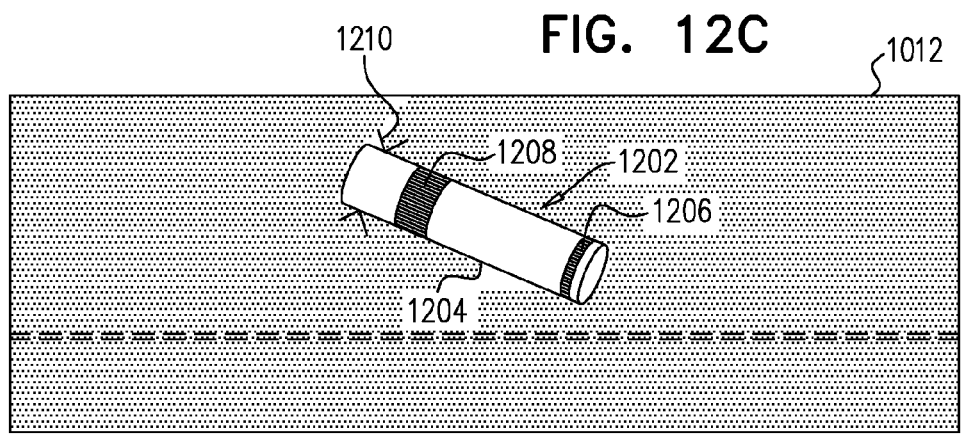

Implant 1202 is configured to be injected via a delivery tube (e.g., a needle) 1219 distally (i.e., distal-half first) into tissue of the subject being treated, as shown in FIGS. 12A-C. Typically, implant 1202 is implanted such that cathode 1206 is disposed closer to nerve 1014 than is anchor 1210 (and therefore closer to nerve 1014 than is any anchor of the implant). This is possible because no anchor protrudes from the distal half of implant 1202. It is hypothesized that this facilitates placement of cathode 1206 close to nerve 1014 while reducing a likelihood of an anchor of the implant damaging the nerve.

For some applications, the positions of the cathode and anode are reversed, e.g., such that reference numeral 1206 refers to the anode of the implant, and reference numeral 1208 refers to the cathode of the implant. For some applications, circuitry 1212 is capable of switching the direction of the current applied by the electrodes, thereby switching each of elements 1206 and 1208 between being an anode and a cathode.

As shown in FIGS. 12A-C, while implant 1202 is disposed within delivery tube 1219 anchor 1210 is in a delivery (e.g., compressed) state, and the anchor automatically expands away from housing 1204 upon deployment from the distal end of the delivery tube.

As shown in FIG. 12B, for applications in which anode 1208 is disposed at a site of housing 1204 that is between cathode 1206 and anchor 1210 (e.g., as shown in embodiments 1202a and 1202b of FIGS. 11A and 11B), both the cathode and the anode are exposed from delivery tube 1219 before the anchor is exposed. In the state shown in FIG. 12B, it is typically possible to wirelessly power implant 1202 in order to test its position with respect to the surrounding tissue (e.g., with respect to nerve 1014). Because anchor 1210 has not yet been deployed, if the position is measured to be suboptimal, it is possible to withdrawn implant 1202 into tube 1219 and reposition the implant before finally anchoring it to the tissue.

It is to be noted that implant 1202 and the techniques described with reference to FIGS. 10A-12C may be used in combination with those described elsewhere herein. For example, implant 1202 may be used in place of another implant described herein, mutatis mutandis, and/or delivery tube 1219 may comprise implant-storage member 1030 of tool 1024. Similarly, tether 1184 may be used to facilitate retrieval and/or anchoring of any of the implants described herein.

Reference is made to FIG. 13, which is a schematic illustration of a mount 1340, which comprises a plurality of cradles 1344 and/or a plurality of lumens 1346, in accordance with some applications of the invention. Similarly to the other mounts described herein, mount 1340 defines a mating edge that is shaped to mate with a mating edge of a guide, such as one or more of the guides described herein.

For example, and as shown, mount 1340 may be shaped to define a receptacle 1342 within which at least a portion of a guide is placeable, typically with a snug fit. For some applications, mount 1340 comprises and/or is integral with the guide, and/or itself defines channels for needle electrodes. Each lumen 1346 of mount 1340 is disposed at a different angle with respect to a skin-contacting surface 1348 of the mount (e.g., each angle corresponding to a respective angle alpha_1 shown for other mounts, mutatis mutandis).

Mount 1340 may be used, mutatis mutandis, in place of other mounts described herein, for facilitating delivery of an implant. For applications in which mount 1340 is used, the step of selecting and/or adjusting a mount responsively to the measured depth of the target site is replaced by (1) selecting a cradle 1344 from the plurality of cradles, and/or a lumen 1346 from the plurality of lumens, and (2) sliding the distal portion of the delivery tool through the selected lumen, and/or coupling the handle of the delivery tool to the selected cradle.

Reference is made to FIGS. 14A-B, which are schematic illustrations of an electrode-guide system 1330, comprising a guide assembly 1326 and an electrode assembly 1328, in accordance with some applications of the invention. Guide assembly 1326 comprises (1) a guide 1334 that is shaped to define at least one channel 1332, and (2) a depth indicator 1350, such as a gauge 1352 (e.g., a plurality of graduated markings). Electrode assembly 1328 comprises at least one needle electrode 1360, and a holder 1354.

For some applications, system 1330 is used in combination with other apparatus and techniques described herein, mutatis mutandis. For example, guide 1334 may be used in place of other guides described herein, and needle electrode 1360 may be used in place of other needle electrodes described herein. System 1330 further facilitates the techniques described hereinabove, by providing coupling and guidance between elements of the system. For example, whereas depth indicator 1050 is shown hereinabove as a discrete element, depth indicator 1350 is coupled to guide 1334. Similarly, electrode 1360 is coupled, via holder 1354, to guide assembly 1326 (e.g., to depth indicator 1350 thereof), such that the electrode is slidable with respect to the depth indicator. For example, a groove 1351 may be defined by indicator 1350, and a flange 1353 may be defined by holder 1354 (or vice versa), and disposition of the flange in the groove slidably couples electrode assembly 1328 to guide assembly 1326. For some applications, system 1330 is provided pre-assembled. For some applications, a user couples electrode assembly 1328 to guide assembly 1326. System 1330 is used to measure the depth of the target site as described hereinabove, mutatis mutandis.

For some applications, system 1330 comprises a ratcheting mechanism 1358 (e.g., a bidirectional ratcheting mechanism) that promotes needle electrode 1360 being in one of a plurality of discrete positions with respect to guide 1334, rather than being advanceable in a continuum of positions. For example, and as shown, mechanism 1358 may comprise a detent 1357 defined by holder 1354, and a plurality of notches 1359 defined by guide assembly 1326 (or vice versa).

Figure 15A:
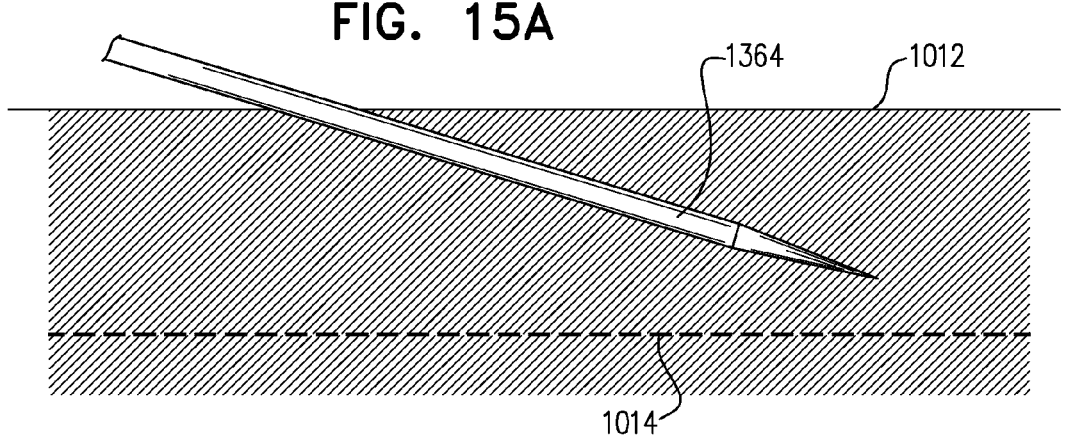
Figure 15B:
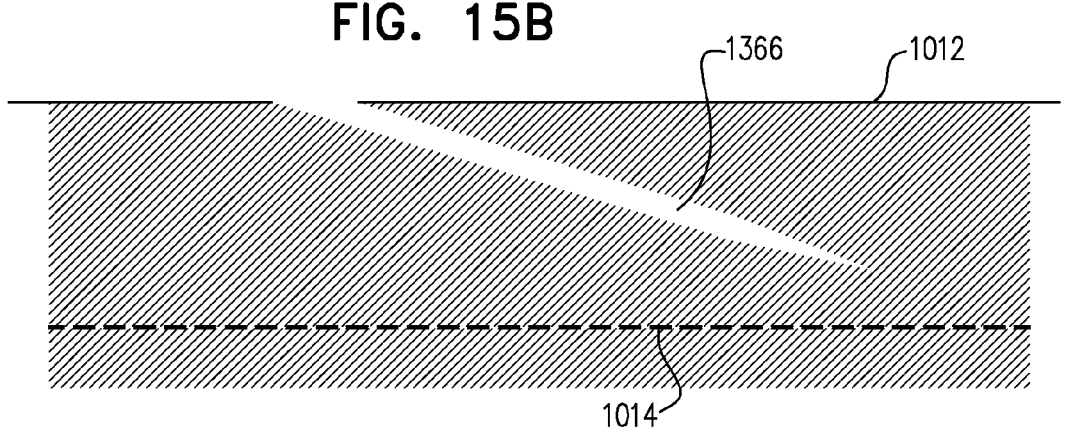
Figure 15C:
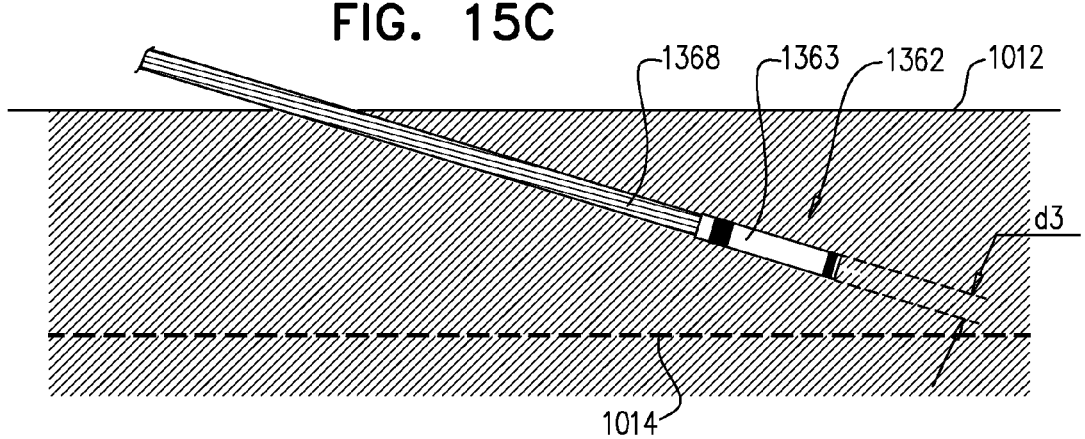

Reference is made to FIGS. 15A-C, 16A-B, and 17A-D, which are schematic illustrations of techniques for percutaneously implanting an implant in tissue of a subject, in accordance with some applications of the invention. FIGS. 15A-C show a generalization of the technique. A puncturing tool 1364 (e.g., a trocar) is percutaneously advanced into the tissue (FIG. 15A). Puncturing tool 1364 is then removed, leaving a tunnel 1366 in the tissue (FIG. 15B). Subsequently, an implant 1362 is advanced to the target site via tunnel 1366, while the implant (e.g., a housing 1363 thereof) is disposed outside of any delivery tube. Thereby, while implant 1362 is being advanced through tunnel 1366, the implant (e.g., housing 1363) is typically in contact with tissue disposed laterally from the tunnel.

The advancement of implant 1362 while its housing is disposed outside of any delivery tube is facilitated by the preceding formation of tunnel 1366, and enables the implant to have a diameter d3 greater than possible when a delivery tube is used: In a particular case in which a particular maximum total diameter exists for elements introduced into the tissue (e.g., due to anatomical constraints and/or pain threshold), when using a delivery tube part of that maximum diameter is consumed by the thickness of the walls of the delivery tube, and width of the implant must therefore be smaller than the particular maximum diameter. In the absence of the delivery tube, the diameter of the implant can thereby be increased up to the maximum diameter. This advantageously facilitates the inclusion of more and/or larger components in the implant.

FIGS. 16A-B show anchoring of an implant 1372, in accordance with some applications of the invention. For some applications, implant 1372 corresponds to and/or is identical to implant 1362, described hereinabove, and is advanced, using a delivery tool 1378, while a housing 1373 of the implant is disposed outside of any delivery tube (FIG. 16A). This typically precludes the use of expandable anchors that are held against the housing by a delivery tube during delivery (such as those described with reference to FIGS. 11A-12C). Implant 1372 comprises one or more anchors 1374, which extend from a proximal end of housing 1373, and are disposed within delivery tool 1378 during delivery. Subsequently to delivery, anchors 1374 are anchored to the tissue using delivery tool 1378, e.g., by withdrawing the tool proximally and allowing the anchors to automatically expand and/or move away from housing 1373 (FIG. 16B).

17A-D show anchoring of an implant 1382, in accordance with some applications of the invention. For some applications, implant 1382 corresponds to and/or is identical to implant 1362, described hereinabove, and is advanced, using a delivery tool 1388, while a housing 1383 of the implant is disposed outside of any delivery tube (FIG. 17A). As described for implant 1372, this typically precludes the use of expandable anchors that are held against the housing by a delivery tube during delivery (such as those described with reference to FIGS. 11A-12C). Implant 1382 comprises at least one anchor 1384, which extends from a proximal end of housing 1383, and comprises a plurality of articulated limbs 1386.

Delivery tool 1388 comprises a first implant-engaging portion 1389 (e.g., a rod) and a second implant-engaging portion 1387 (e.g., a tube, through which the rod is disposed). Anchor 1384 is anchored to the tissue by changing a shape of the anchor (e.g., deforming the anchor) by applying a force to the anchor using portion 1387, while providing a reference force to housing 1383 using portion 1389, e.g., so as to inhibit movement of housing 1383 in response to the force applied to the anchor (FIG. 17B). For example, and as shown, portion 1387 may be used to apply a distally-directed force to anchor 1384, while portion 1389 is used to apply a proximally-directed force to the housing. In response to the applied force, limbs 1386 articulate with respect to each other and/or with respect to housing 1383, in a manner that anchors anchor 1384 to the tissue, e.g., by protruding radially outward, as shown. For some applications, anchor 1384 functions similarly to a drywall fastener, such as a "molly bolt."

Figure 17C:
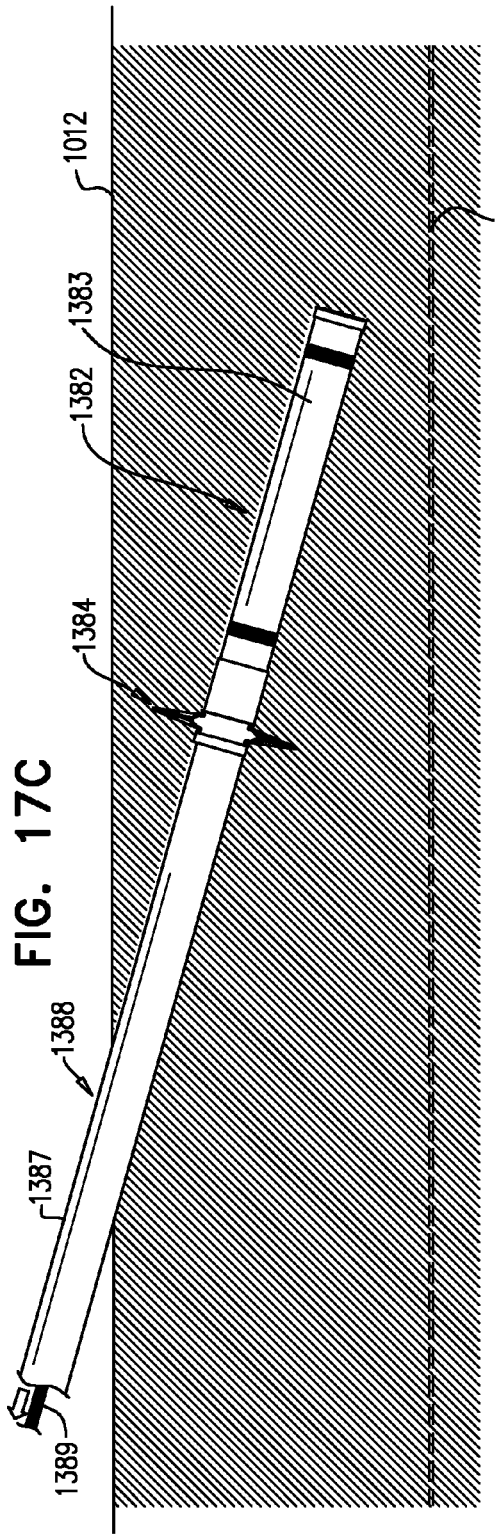
Figure 17D:
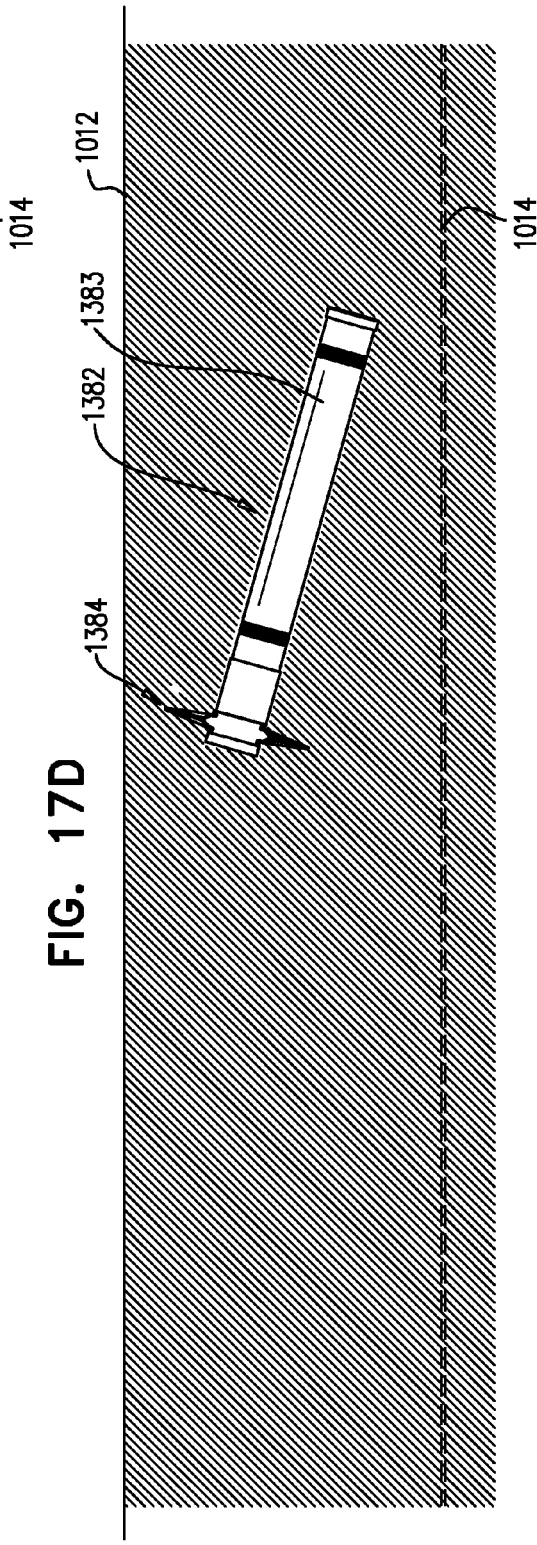

Subsequently to the anchoring, portion 1389 is decoupled from housing 1383, such as by unscrewing, or by another suitable technique, typically while a reference force is provided by portion 1387 (FIG. 17C). Tool 1388 is then removed from the tissue (FIG. 17D).

For some applications, the advancement of a puncturing tool, a delivery tool and an implant into the tissue of the subject described with reference to FIGS. 15A-17D is performed in combination with other techniques described herein, such as by advancing the element(s) via a lumen defined by a mount described herein. The delivery tools described with reference to FIGS. 15A-17D may be used in place of another delivery tool described herein, and/or the implants described with reference to FIGS. 15A-17D may be used in place of another implant described herein.

Reference is again made to FIGS. 1A-17D. It is to be noted that, although the implants described herein are typically shown as being introduced via the medial side of the leg, for some applications the implants are introduced via the lateral side of the leg.

For some applications, the apparatus and techniques described herein may be used in combination with one or more of those described in the following references, all of which are incorporated herein by reference:

U.S. Pat. No. 8,788,045 to Gross et al., filed Jun. 8, 2010, and entitled "Tibial Nerve Stimulation";

U.S. Pat. No. 8,755,893 to Gross et al., filed Mar. 14, 2013, and entitled "Tibial Nerve Stimulation";

PCT Patent Application Publication WO 2013/111137 to Gross et al., filed Jan. 24, 2013, and entitled "Wireless Neurostimulators";

PCT Patent Application Publication WO 2014/087337 to Gross et al., filed Dec. 3, 2013, and entitled "Delivery of Implantable Neurostimulators";

A US Patent Application to Oron et al., filed on even date herewith, and entitled "Extracorporeal Implant Controllers", which received U.S. Ser. No. 14/601,626, and which published as US 2016/0206890; and A US Patent Application to Plotkin et al., filed on even date herewith, and entitled "Transmitting Coils for Neurostimulation", which received Ser. No. 14/601,568, and which published as US 2016/0206889.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an implant, the implant comprising:
    a rod-shaped housing, having a distal half and a proximal half, and configured to be injected distally into tissue of a subject;
    a first electrode, configured to function as a cathode on the distal half of the housing;
    an anchor configured to protrude from the proximal half of the housing, no anchor being configured to protrude from the distal half of the housing;
    a second electrode, configured to function as an anode, and disposed at a site of the housing that is distal to the anchor and proximal from the cathode; and circuitry disposed within the housing, configured to configure the first electrode to function as the cathode, to configure the second electrode to function as the anode, and to drive a current between the cathode and the anode, wherein the anchor comprises a tether that has:
- a distal end coupled to the housing, and configured to remain coupled to the housing during and after injection of the housing,
- a proximal end, configured to remain outside the subject during and after the injection of the housing, and
- a distal portion that comprises the distal end, and is configured to promote tissue growth that adheres the distal portion to the tissue, thereby inhibiting movement of the housing with respect to the tissue.

2. The apparatus according to claim 1, wherein the anode is disposed on the proximal half of the housing.

3. The apparatus according to claim 1, wherein the anode has a larger surface area than the cathode.

4. The apparatus according to claim 1, further comprising an antenna configured to receive wirelessly-transmitted power, wherein the circuitry is configured to use the received power to drive the current between the cathode and the anode.

5. The apparatus according to claim 4, wherein the antenna is disposed within the housing.

6. The apparatus according to claim 4, wherein the antenna is disposed between the anode and the cathode.

7. The apparatus according to claim 4, wherein the antenna is disposed proximal to the anode.

8. The apparatus according to claim 7, further comprising a delivery tube, wherein:
the implant is configured to be injected distally into the tissue by being disposed, in a delivery state, within the delivery tube with the distal half of the housing disposed closer to a distal opening of the delivery tube than is the proximal half of the housing,
in the delivery state the anchor is in a restrained state thereof, and
the anchor is configured to automatically expand away from the housing upon deployment from the delivery tube.

9. The apparatus according to claim 1, wherein the tether has a connecting portion that couples the proximal end to the distal portion, and is configured to be disposed within the subject after the injection of the housing, the connecting portion:
having a first state in which the connecting portion is capable of transferring sufficient tension from the proximal end to the distal portion to pull the housing out of the subject, and
being configured to weaken in response to being disposed within the subject, such that, after a duration of being disposed within the subject, tension applied to the proximal end of the tether decouples the proximal end from the distal portion of the tether, the duration being at least 1 day.

10. The apparatus according to claim 9, wherein the connecting portion is configured to weaken by becoming absorbed by the tissue of the subject.

11. The apparatus according to claim 9, wherein the distal portion has a coating that is configured to inhibit the promotion of tissue growth for a period of the coating being disposed within the subject, and to decrease inhibiting the promotion of tissue growth after the period, the period being at least 1 day.

12. The apparatus according to claim 11, wherein the coating and the connecting portion are configured such that the duration is longer than the period.

13. The apparatus according to claim 1, further comprising a delivery tool that comprises a tube via which the housing is injectable while the distal end of the tether is coupled to the housing.

14. A method, comprising:
injecting, distally into tissue of a subject, a rod-shaped housing of an implant, wherein:
the rod-shaped housing has a distal half and a proximal half,
the implant comprises:
a first electrode, configured to function as a cathode on the distal half of the housing;
an anchor configured to protrude from the proximal half of the housing, no anchor being configured to protrude from the distal half of the housing;
a second electrode, configured to function as an anode, and disposed at a site of the housing that is distal to the anchor and proximal from the cathode; and
circuitry disposed within the housing, configured to configure the first electrode to function as the cathode, to configure the second electrode to function as the anode, and to drive a current between the cathode and the anode,
wherein:
the anchor comprises a tether that has:
a distal end coupled to the housing,
a proximal end, and
a distal portion that comprises the distal end,
injecting the housing comprises:
injecting the housing while (i) the distal end of the tether remains coupled to the housing, and (ii) the proximal end of the tether remains disposed outside of the subject, and
leaving (i) the distal end of the tether coupled to the housing, and (ii) the proximal end of the tether outside of the subject, and
the distal portion of the tether is configured to promote tissue growth that adheres the distal portion to the tissue, thereby inhibiting movement of the housing with respect to the tissue.

* * * * *

UNITED STATES PATENT AND TRADEMARK OFFICE
CERTIFICATE OF CORRECTION

| | | |
|---|---|---|
| PATENT NO. | : 10,004,896 B2 | |
| APPLICATION NO. | : 14/601604 | |
| DATED | : June 26, 2018 | |
| INVENTOR(S) | : Gur Oron et al. | |

It is certified that error appears in the above-identified patent and that said Letters Patent is hereby corrected as shown below:

On the Title Page

Under Inventors, please correct the first inventor from "Guri Oron" to --Gur Oron--

Signed and Sealed this
Fourth Day of October, 2022

Katherine Kelly Vidal
*Director of the United States Patent and Trademark Office*